US006537540B1

(12) United States Patent
Burstein et al.

(10) Patent No.: US 6,537,540 B1
(45) Date of Patent: Mar. 25, 2003

(54) METHODS AND COMPOSITION FOR LOWERING THE LEVEL OF TUMOR NECROSIS FACTOR (TNF) IN TNF-ASSOCIATED DISORDERS

(75) Inventors: Haim Burstein, Redmond, WA (US); Anthony M. Stepan, Seattle, WA (US)

(73) Assignee: Targeted Genetics Corporation, Seattle, WA (US)

( * ) Notice: Subject to any disclaimer, the term of this patent is extended or adjusted under 35 U.S.C. 154(b) by 0 days.

(21) Appl. No.: 09/579,845

(22) Filed: May 26, 2000

Related U.S. Application Data

(60) Provisional application No. 60/150,688, filed on May 28, 1999.

(51) Int. Cl.[7] ......................... A61K 48/00; C12N 15/86

(52) U.S. Cl. ................... 424/93.2; 435/320.1; 435/456; 514/44

(58) Field of Search ........................... 424/93.2; 514/44, 514/2; 435/320.1, 456

(56) References Cited

U.S. PATENT DOCUMENTS

| | | | | |
|---|---|---|---|---|
| 5,173,414 A | | 12/1992 | Lebowski et al. | 435/91.4 |
| 5,350,683 A | | 9/1994 | Sims et al. | 435/69.1 |
| 5,395,760 A | | 3/1995 | Smith et al. | 435/365 |
| 5,399,346 A | | 3/1995 | Anderson et al. | 424/93.21 |
| 5,478,745 A | | 12/1995 | Samulski et al. | 435/320.1 |
| 5,587,308 A | | 12/1996 | Carter et al. | 435/371 |
| 5,605,690 A | | 2/1997 | Jacobs et al. | 424/134.1 |
| 5,633,145 A | | 5/1997 | Feldmann et al. | 435/69.1 |
| 5,658,776 A | | 8/1997 | Flotte et al. | 435/457 |
| 5,658,785 A | | 8/1997 | Johnson | 435/367 |
| 5,766,585 A | | 6/1998 | Evans et al. | 424/93.21 |
| 5,780,447 A | | 7/1998 | Nienhuis | 514/44 |
| 5,786,211 A | | 7/1998 | Johnson | 435/320.1 |
| 5,792,751 A | | 8/1998 | Ledley et al. | 514/44 |
| 5,837,484 A | | 11/1998 | Trempe et al. | 435/69.1 |
| 5,843,725 A | | 12/1998 | Sledziewski et al. | 435/69.7 |
| 5,843,742 A | | 12/1998 | Natsoulis et al. | 435/465 |
| 5,846,528 A | | 12/1998 | Podsakoff et al. | 424/93.2 |
| 5,858,351 A | | 1/1999 | Podsakoff et al. | 424/93.2 |
| 5,858,355 A | | 1/1999 | Glorioso et al. | 424/93.21 |
| 5,858,775 A | | 1/1999 | Johnson | 435/320.1 |
| 6,018,026 A | | 1/2000 | Sledziewski et al. | 530/350 |
| 6,159,464 A | * | 12/2000 | Glorioso et al. | 424/93.2 |
| 6,291,212 B1 | | 9/2001 | Sledziewski et al. | 435/691 |
| 6,291,646 B1 | | 9/2001 | Sledziewski et al. | 530/350 |
| 6,300,099 B1 | | 10/2001 | Sledziewski et al. | 435/69.1 |
| 6,306,820 B1 | * | 10/2001 | Bendele et al. | 514/2 |
| 6,323,323 B1 | | 11/2001 | Sledziewski et al. | 530/387.3 |

FOREIGN PATENT DOCUMENTS

| | | |
|---|---|---|
| WO | WO 92/11359 | 7/1992 |
| WO | WO 94/06476 A1 | 3/1994 |
| WO | WO 94/20517 | 9/1994 |
| WO | WO 95/13365 | 5/1995 |
| WO | WO 95/16353 | 6/1995 |
| WO | WO 96/17947 | 6/1996 |
| WO | WO 97/17458 | 5/1997 |
| WO | WO 97/32990 | 9/1997 |
| WO | WO 98/27204 | 6/1998 |
| WO | WO 98/27207 | 6/1998 |
| WO | WO 98/37901 A1 | 9/1998 |
| WO | WO 99/11764 | 3/1999 |
| WO | WO 99/20773 | 4/1999 |
| WO | WO 99/20779 | 4/1999 |
| WO | WO 00/14205 | 3/2000 |

OTHER PUBLICATIONS

Zhang et al; Arthritis & Rhevmatigm 41 (9 Suppl.): 1998, S96.*

Robbins et al; Gene Therapy for Rheumatoid Arthritis, 1998, Springer Semin Immunopathol 20: 197–209.*

Dinant, H.J. and Dijkmans, B.A.C. (Apr., 1999). "New Therapeutic Targets for Rheumatoid Arthritis," *Pharmacy World and Science* 21(2):49–59.

Hallek, M. and Wendtner, C. (1996). "Recombinant Adeno–Associated Virus (rAAV) Vectors for Somatic Gene Therapy: Recent Advances and Potential Clinical Applications," *Cytokines and Molecular Therapy* 2:69–79.

"Enbrel Injections Difficult for Some Patients" at <http://dailynews.yahoo.com/h/nm/20000516/hl/arthritis_drugs_1.html> (Visited on May 16, 2000).

"Important Drug Warning" at <http://www.fda.gov/medwatch/safety/1999/enbrel.htm> (Visited on May 22, 2000).

"New Warning For Arthritis Drug, Enbrel" at <http://www-.fda.gov/bbs/topics/ANSWERS/ANS00954.html> (Visited on May 22, 2000).

"Product Information" at <http://www.enbrel.com/patient/html/patpi.htm> (Visited on May 17, 2000).

"Proven Tolerability" at <http://www.enbrel.com/patient/html/patsafety.htm> (Visited on May 17, 2000).

Ahmadzadeh, N. et al. (1990). "The effect of recombinant tumor necrosis factor–α on superoxide and metalloproteinase production by synovial cells and chondrocytes," *Clin. Exp. Rheumatol.* 8:387–391.

Atkinson, E.M. et al. (1998). "A high–throughput hybridization method for titer determination of viruses and gene therapy vectors," *Nucleic Acid Res.* 26(11):2821–2823.

Bader, T. and Nettesheim, P. (1996). "Tumor necrosis factor–α modulates the expression of its p60 receptor and several cytokines in rat tracheal epithelial cells," *J. Immunol.* 157(7):3089–3096.

(List continued on next page.)

*Primary Examiner*—Scott D. Priebe
(74) *Attorney, Agent, or Firm*—Morrison&Foerster LLP

(57) ABSTRACT

The present invention provides recombinant adeno-associated virus (rAAV) vectors encoding a tumor necrosis factor (TNF) antagonist and methods using these vectors to reduce levels of TNF in a mammal. The invention also provides methods of using these rAAV vectors in palliating TNF-associated disorders.

16 Claims, 26 Drawing Sheets

OTHER PUBLICATIONS

Baert, F.J. et al. (1999). Tumor necrosis factor–$\alpha$ antibody (infliximab) therapy profoundly down–regulates the inflammation in Crohn's ileocolitis, *Gastroenterology* 116(1):22–28.

Barr, D. et al. (1995). "Strain related variations in adenovirally mediated transgene expression from mouse hepatocytes in vivo: comparisons between immunocompetent and immunodeficient inbred strains," *Gene Therapy* 2:151–155.

Berns, K.I. (1990). "Parvoviridae and their replication," Chapter 62 in *Virology.* Raven Press, NY, pp. 1743–1763.

Blacklow, N.R. (1988). "Adeno–associated viruses of humans," Chapter 11 in *Parvoviruses and Human Disease.* Pattison, J.R., ed, FL, pp. 165–174.

Bresnihan, B. et al. (1996). "Treatment with recombinant human interleukin–1 receptor antagonist (rhIL–1ra) in rheumatoid arthritis (RA): Results of a randomized double–blind, placebo–controlled multicenter trial," *Arthritis & Rheum.* 39(9):S73, Abstract #282.

Brüggemann, M. (1988). "Evolution of the rat immunoglobulin gamma heavy–chain gene family," *Gene* 74:473–482.

Byrnes, A.P. et al. (1995). "Adenovirus gene transfer causes inflammation in the brain," *Neuroscience* 66(4):1015–1024.

Campion, G.V. et al. (1996). "Dose–range and dose–frequency study of recombinant human interleukin–1 receptor antagonist in patients with rheumatoid arthritis," *Arthritis Rheum.* 39(7):1092–1101.

Camussi, G. and Lupia, E. (1998). "The future role of anti–tumor necrosis factor (TNF) products in the treatment of rheumatoid arthritis," *Drugs* 55(5):613–620.

Carter, B.J. et al. (1989). "AAV DNA replication, integration, and genetics," Chapter 11 in *Handbook of Parvoviruses Vol. I.* pp. 169–226.

Carter, B.J. (1992). "Adeno–associated virus vectors," *Current Opinion in Biotechnology* 3:533–539.

Ceconi, C. et al. (1998). "Tumor necrosis factor in congestive heart failure: A mechanism of disease for the new millenium?," *Prog. Cardiovasc. Dis.* 41(1):25–30.

Clark, K.R. et al. (1995). "Cell lines for the production of recombinant adeno–associated virus," *Hum. Gene Ther.* 6:1329–1341.

Clark, K.R. et al. (1996). "A stable cell line carrying adenovirus–inducible rep and cap genes allows for infectivity titration of adeno–associated virus vectors," *Gene Therapy* 3:1124–1132.

Cormack, B.P. et al. (1996). "FACS–optimized mutants of the green fluorescent protein (GFP)," *Gene* 173:33–38.

Cromartie, W.J. et al. (1977). "Arthritis in rats after systemic injection of streptococcal cells or cell walls," *J. Exp. Med.* 146:1585–1602.

Database Genbank Accesion No. M28670, 'Evolution of the rat immunoglobulin gamma heavy–chain gene family,' Jan. 14, 1995, "NCBI Sequence Viewer" at <http://www.ncbi.nlm.nih.gov/entrez/query.fcgi?CMD=Display&DB=Nucleotide> (Visited on Sep. 14, 2000).

Database Genbank, Accesion No. M32315, 'A receptor for tumor necrosis factor defines an unusual family of cellular and viral proteins,' Jan. 7, 1995, "NCBI Sequence Viewer" at <http://www.ncbi.nlm.nih.gov/entrez/query.fcgi?CMD=Display&DB=Nucleotide> (Visited on Sep. 14, 2000).

Database Genbank, Accesion No. M59378, 'Molecular cloning and expression of the type 1 and type 2 murine receptors for tumor necrosis factor,' Apr. 27, 1993, "NCBI Sequence Viewer" at <http://www.ncbi.nlm.gov/entrez/query.fcgi?CMD=Display&DB=Nucleotide> Visited on Sep. 14, 2000).

Database Genbank, Accesion No. U74649, 'Complete nucleotide sequence and expression of the human interleukin–1 receptor type II in human gingival fibroblasts,' Jan. 5, 1999, "NCBI Sequence Viewer" at <http://www.ncbi.nlm.nih.gov/entrez/query.fcgi?CMD=Display&DB=Nucleotide> (Visited on Sep. 14, 2000).

Elliott, M.J. et al. (1993). "Treatment of rheumatoid arthritis with chimeric monoclonal antibodies to tumor necrosis factor $\alpha$," *Arthritis & Rheum.* 36(12):1681–1690.

Elliott, M.J. et al. (1994). "Randomized double–blind comparison of chimeric monoclonal antibody to tumour necrosis factor $\alpha$(cA2) versus placebo in rheumatoid arthritis," *Lancet* 344:1105–1110.

Engleman, H. et al. (1989). "A tumor necrosis factor–binding protein purified to homogeneity from human urine protects cells from tumor necrosis factor toxicity," *J. Biol. Chem.* 264(20):11974–11980.

Evans, R.C. et al. (1997). "Treatment of ulcerative colitis with an engineered human anti–TNF$\alpha$ antibody CDP571," *Ailment. Pharmacol. Ther.* 11:1031–1035.

Feldmann, M. et al. (1997). "Anti–tumor necrosis factor–$\alpha$ therapy of rheumatoid arthritis," *Adv. Immunol.* 64:283–350.

Firestein, G.S. et al. (1997). "Anticytokine therapy in rheumatoid arthritis," *N. Eng. J. Med.* 337(3):195–197.

Flotte, T.R. et al. (1992). "Gene Expression from adeno–associated virus vectors in airway epithelial cells," *Am. J. Respir. Cell. Mol. Biol.* 7:349–356.

Flotte, T.R. et al. (1993). "Stable in vivo expression of the cystic fibrosis transmembrane conductance regulator with an adeno–associated virus vector," Proc. *Natl. Acad. Sci. USA* 90:10613–10617.

Flotte, T.R. et al. (1995). "An improved system for packaging recombinant adeno–associated virus vectors capable of in vivo transduction," *Gene Ther.* 2:29–37.

Frohman, M.A. et al. (1988). "Rapid production of full–length cDNAs from rare transcripts: Amplification using a single gene–specific oligonucleotide primer," *Proc. Natl. Acad. Sci. USA* 85:8998–9002.

Gearing, A.J.H. et al. (1987). "A simple sensitive bioassay for interleukin–1 which is unresponsive to $10^3$ U/ml of interleukin–2," *J. Immunol. Methods* 99:7–11.

Ghivizzani, S.C. et al. (1998). "Direct adenovirus–mediated gene transfer of interleukin 1 and tumor necrosis factor $\alpha$ soluble receptors to rabbit knees with experimental arthritis has local and distal anti–arthritic effects," *Proc. Natl. Acad. Sci. USA* 95:4613–4618.

Harris, E.D. (1990). "Rheumatoid Arthritis," *N. Engl. J. Med.* 323(14)994–996.

Heim, R. et al. (1995). "Improved green fluorescence," *Nature* 373:663–664.

Hermonat, P.L. and Muzyczka, N. (1984). "Use of adeno–associated virus as a mammalian DNA cloning vector: Transduction of neomycin resistance into mammalian tissue culture cells," *Proc. Natl. Acad. Sci. USA* 81:6466–6470.

Husby, G. and Williams, R.C. (1988). "Synovial localization of tumor necrosis factor in patients with rheumatoid arthritis," *J. Autoimmun.* 1:363–371.

Issekutz, A.C. et al. (1994). "The role of tumour necrosis factor–alpha and IL–1 in polymorphonuclear leucocyte and T lymphocyte recruitment to joint inflammation in adjuvant arthritis," *Clin. Exp. Immunol.* 97:26–32.

Joosten, L.A.B. et al. (1996). "Anticytokine treatment of established type II collagen–induced arthritis in DBA/1 mice," *Arthritis Rheum.* 39(5):797–809.

Kang, R. et al. (1997). "Gene therapy for arthritis: principles and clinical practice," *Biochemical Society Transactions* 25:533–537.

Kaplitt, M.G. et al. (1994). "Long term gene expression and phenotypic correction using adeno–associated virus vectors in mammalian brain," *Nat. Genet.* 8:148–154.

Kavanaugh, A.F. (1998). "Anti–tumor necrosis factor–α monoclonal antibody therapy for rheumatoid arthritis," *Rheum. Dis. Clin. North Am.* 24(3):593–614.

Kessler, P.D. et al. (1996). "Gene delivery to skeletal muscle results in sustained expression and systemic delivery of a therapeutic protein," *Proc. Natl. Acad. Sci. USA* 93:14082–14087.

Khabar, K.S.A. et al. (1995). "WEHI–13VAR: A stable and sensitive variant of WEHI 164 clone 13 fibrosarcoma for tumor necrosis factor bioassay," *Immunol. Lett.* 46:107–110.

Koeberl, D.D. et al. (1997). "Persistent expression of human clotting factor IX from mouse liver after intravenous injection of adeno–associated virus vectors," *Proc. Natl. Acad. Sci. USA* 94:1426–1431.

Kuiper, S. et al. (1998). "Different roles of tumour necrosis factor α and interleukin 1 in murine streptococcal cell wall arthritis," *Cytokine* 10(9):690–702.

Le, C.H. et al. (1997). "Suppression of collagen–induced arthritis through adenovirus–mediated transfer of a modified tumor necrosis factor α receptor gene," *Arthritis Rheum.* 40(9):1662–1669.

Lebkowski, J. S. et al. (1998). "Adeno–associated virus: a vector system for efficient introduction and integration of DNA into a variety of mammalian cell types," *Mol. Cell. Biol.* 8(10):3988–3996.

Lechman, E.R. et al. (1999). "Direct adenoviral gene transfer of viral IL–10 to rabbit knees with experimental arthritis ameliorates disease in both injected and contralateral control knees," *J.Immunology* 163(4):2202–2208.

Lewthwaite, J. et al. (1995). "Role of TNFα in the induction of antigen induced arthritis in the rabbit and the anti–arthritic effect of species specific TNFα neutralizing monoclonal antibodies," *Ann. Rheum. Dis.* 54:366–374.

Loetscher, H. et al. (1990). "Molecular cloning and expression of the human 55kd tumor necrosis factor receptor," *Cell* 61:351–359.

Lovell, D.J. (1998). "Safety and efficacy of tumor necrosis factor receptor p75 FC fusion protein (TNFR:FC) in polyarticular course juvenile rheumatoid arthritis," Am. College of Rheumatology meeting, Nov. 9, 1998, abstract 584.

Lynch, C.M. et al. (1997). "Adeno–associated virus vectors for vascular gene delivery," *Circ. Res.* 80(4):497–505.

MacNaul, K.L. et al. (1992). "Differential effects of IL–1 and TNF alpha on the expression of stromelysin, collagenase and their natural inhibitor, TIMP, in rheumatoid human synovial fibroblasts," *Matrix Suppl.* 1:198–199.

Maini, R.N. et al. (1998). "Therapeutic efficacy of multiple intravenous infusions of anti–tumor necrosis factor α monoclonal antibody combined with low–dose weekly methotrexate in rheumatoid arthritis," *Arthritis Rheum.* 41(9):1552–1563.

McCoy, R.D. et al. (1995). "Pulmonary inflammation induced by incomplete or inactivated adenoviral particles," *Human Gene Therapy* 6:1553–1560.

McLaughlin, S.K. et al. (1988). "Adeno–associated virus general transduction vectors: Analysis of proviral structures," *J. Virol.* 62(6):1963–1973.

Miagkov, A.V. et al. (1998). "NF–κB activation provides the potential link between inflammation and hyperplasia in the arthritic joint," *Proc. Natl. Acad. Sci. USA* 95:13859–13864.

Mohler, K.M. et al. (1993). "Soluble tumor necrosis factor (TNF) receptors are effective therapeutic agents in lethal endotoxemia and function simultaneously as both TNF carriers and TNF antagonists," *J. Immunol.* 151(3):1548–1561.

Moreland, L.W. et al. (1997). "Treatment of rheumatoid arthritis with a recombinant human tumor necrosis factor receptor (p75)–Fc fusion proteins," *N. Eng. J. Med.* 337(3):141–147.

Moser, R. et al. (1989). "Interleukin 1 and tumor necrosis factor stimulate human vascular endothelial cells to promote transendothelial neutrophil passage," *J. Clin. Invest.* 83(2):444–455.

Müller–Ladner, U. et al. (1997). "Human IL–1Ra gene transfer into human synovial fibroblasts is chondroprotective," *J. Immunol.* 158:3492–3498.

Muzyczka, N. (1992). "Use of adeno–associated virus as a general transduction vector for mammalian cells," *Curr. Top. Microbiol. Immunol.* 158:97–129.

Nawroth, P.P. et al. (1986). "Tumor necrosis factor/cachectin interacts with endothelial cell receptors to induce release of interleukin 1," *J. Exp. Med.* 163:1363–1375.

Pelletier, J. et al. (1997). "In vivo suppression of early experimental osteoarthritis by interleukin–1 receptor antagonist using gene therapy," *Arthritis Rheum.* 40(6):1012–1019.

Piguet, P.F. et al. (1992). "Evolution of collagen arthritis in mice is arrested by treatment with anti–tumour necrosis factor (TNF) antibody or a recombinant soluble TNF receptor," *Immunology* 77:510–514.

Potter, H. et al. (1984). "Enhanced–dependent expression of human κ immunoglobulin genes introduced into mouse pre–B lymphocytes by electroporation," *Proc. Natl. Acad. Sci. USA* 81(22):7161–7165.

Robbins, P.D. et al. (1997). "Gene transfer to joints," *Drug News & Perspect.* 10(5):283–292.

Rose, J.A. (1974). "Parvovirus reproduction," Chapter 1 in *Comprehensive Virology* 3:1–61.

Roux–Lombard, P. et al. (1993). "Soluble tumor necrosis factor receptors in human inflammatory synovial fluids," *Arthritis Rheum.* 36(4):485–489.

Rutgeerts, P. (1998). "Medical therapy of inflammatory bowel disease," *Digestion* 59:453–469.

Samulski, R.J. et al. (1989). "Helper–free stocks of recombinant adeno–associated viruses: Normal integration does not require viral gene expression," *J. Virol.* 63(9):3822–3828.

Schiff, M. (1997). "Emerging treatments for rheumatoid arthritis," *Am. J. Med.* 102(1A):11S–15S.

Schimmer, R. C. et al. (1997). "Streptococcal cell wall–induced arthritis," *J. Immunol.* 159(8):4103–4108.

Shingu, M. et al. (1993). "The effects of cytokines on metalloproteinase inhibitors (TIMP) and collagenase production by human chondrocytes and TIMP production by synovial cells and endothelia cells," *Clin. Exp. Immunol.* 94:145–149.

Smith, C.A. et al. (1990). "A receptor for tumor necrosis factor defines an unusual family of cellular and viral proteins," *Science* 248(4958): 1019–1023.

Snyder, R.O. et al. (1997). "Persistent and therapeutic concentrations of human factor IX in mice after hepatic gene transfer of recombinant AAV vectors," *Nat. Genet.* 16:270–276.

Song, X. et al. (1998). "Plasmid DNA encoding transforming growth factor–β1 suppresses chronic disease in a streptococcal cell wall–induced arthritis model," *J. Clin. Invest.* 101(12):2615–2621.

Takashiba, S. et al. (1993). "Cloning and characterization of human TNFα promoter region," *Gene* 131:307–308.

Tamayose, K. et al. (1996). "A new strategy for large–scale preparation of high–titer recombinant adeno–associated virus vectors by using packaging cell lines and sulfonated cellulose column chromatography," *Hum. Gene Ther.* 7:507–513.

Tetta, C. et al. (1990). "Tumor necrosis factor in serum and synovial fluid of patients with active and severe rheumatoid arthritis," *Ann. Rheum. Dis.* 49:665–667.

Thorbecke,G.J. et al. (1992). "Involvement of endogenous tumor necrosis factor α and transforming growth factor β during induction of collagen type II arthritis in mice," *Proc. Natl. Acad. Sci. USA* 89:7375–7379.

Tratschin, J. et al. (1984). "A human parvovirus, adeno–associated virus, as a eucaryotic vector: Transient expression and encapsidation of the procaryotic gene for chloramphenicol acetyltransferase," *Mol. Cell. Biol.* 4(10):2072–2081.

Tratschin, J. et al. (1985). "Adeno–associated virus vector for high–frequency integration, expression, and rescue of genes in mammalian cells," *Mol. Cell. Biol.* 5(11):3251–3260.

Varley, A.W. and Munford, R.S. (1998). "Physiologically responsive gene therapy," *Mol. Med. Today* 4:445–451.

Whalen, J.D. et al. (1999). "Adenoviral transfer of the viral IL–10 gene periarticularly to mouse paws suppresses development of collagen–induced arthritis in both injected and uninjected paws," *J Immunol.* 162:3625–3632.

Williams, R.O. et al. (1992). "Anti–tumor necrosis factor ameliorates joint disease in murine collagen–induced arthritis," *Proc. Natl. Acad. Sci. USA,* 89:9784–9788.

Wooley, P.H. et al. (1993). "Influence of a recombinant human soluble tumor necrosis factor receptor FC fusion protein on type II collagen–induced arthritis in mice," *J. Immunol.* 151(11):6602–6607.

Xiao, X. et al. (1996). "Efficient long–term gene transfer into muscle tissue of immunocompetent mice by adeno–associated virus vector," *J. Virol.* 70(11):8098–8108.

Yakobson, B.et al. (1987). "Replication of adeno–associated virus in synchronized cells without the addition of a helper virus," *J. Virol.* 61(4):972–981.

Zolutukhin, S. et al. (1999). "Recombinant adeno–associated virus purification using novel methods improves infectious titer and yield," *Gene therapy* 6:973–985.

* cited by examiner

AlaArgGlnAlaAlaTrpArgGluGlyAlaGlyLeuArgGlyArgGlu
GlyAlaArgAlaGlyGlyAsnArgThrProProAlaSerMetAlaPro
ValAlaValTrpAlaAlaLeuAlaValGlyLeuGluLeuTrpAlaAla
AlaHisAlaLeuProAlaGlnValAlaPheThrProTyrAlaProGlu
ProGlySerThrCysArgLeuArgGluTyrTyrAspGlnThrAlaGln
MetCysCysSerLysCysSerProGlyGlnHisAlaLysValPheCys
ThrLysThrSerAspThrValCysAspSerCysGluAspSerThrTyr
ThrGlnLeuTrpAsnTrpValProGluCysLeuSerCysGlySerArg
CysSerSerAspGlnValGluThrGlnAlaCysThrArgGluGlnAsn
ArgIleCysThrCysArgProGlyTrpTyrCysAlaLeuSerLysGln
GluGlyCysArgLeuCysAlaProLeuArgLysCysArgProGlyPhe
GlyValAlaArgProGlyThrGluThrSerAspValValCysLysPro
CysAlaProGlyThrPheSerAsnThrThrSerSerThrAspIleCys
ArgProHisGlnIleCysAsnValValAlaIleProGlyAsnAlaSer
MetAspAlaValCysThrSerThrSerProThrArgSerMetAlaPro
GlyAlaValHisLeuProGlnProValSerThrArgSerGlnHisThr
GlnProThrProGluProSerThrAlaProSerThrSerPheLeuLeu
ProMetGlyProSerProProAlaGluGlySerThrGlyAspGluPro
LysSerCysAspLysThrHisThrCysProProCysProAlaProGlu
LeuLeuGlyGlyProSerValPheLeuPheProProLysProLysAsp
ThrLeuMetIleSerArgThrProGluValThrCysValValValAsp
ValSerHisGluAspProGluValLysPheAsnTrpTyrValAspGly
ValGluValHisAsnAlaLysThrLysProArgGluGluGlnTyrAsn
SerThrTyrArgValValSerValLeuThrValLeuHisGlnAspTrp
LeuAsnGlyLysAspTyrLysCysLysValSerAsnLysAlaLeuPro
AlaProMetGlnLysThrIleSerLysAlaLysGlyGlnProArgGlu
ProGlnValTyrThrLeuProProSerArgAspGluLeuThrLysAsn
GlnValSerLeuThrCysLeuValLysGlyPheTyrProArgHisIle
AlaValGluTrpGluSerAsnGlyGlnProGluAsnAsnTyrLysThr
ThrProProValLeuAspSerAspGlySerPhePheLeuTyrSerLys
LeuThrValAspLysSerArgTrpGlnGlnGlyAsnValPheSerCys
SerValMetHisGluAlaLeuHisAsnHisTyrThrGlnLysSerLeu
SerLeuSerProGlyLys

Fig. 1

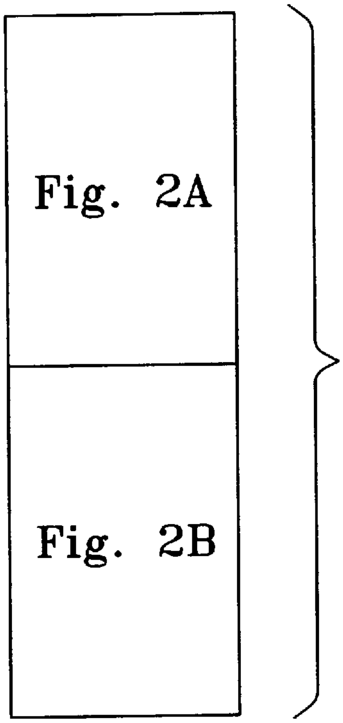

```
GCGAGGCAGGCAGCCTGGAGAGAAGGCGCTGGGCTGCGAGGGCGCGAG  48
AlaArgGlnAlaAlaTrpArgGluGlyAlaGlyLeuArgGlyArgGlu
GGCGCGAGGGCAGGGGGCAACCGGACCCCGCCCGCATCCATGGCGCCC  96
GlyAlaArgAlaGlyGlyAsnArgThrProProAlaSerMetAlaPro
GTCGCCGTCTGGGCCGCGCTGGCCGTCGGACTGGAGCTCTGGGCTGCG  144
ValAlaValTrpAlaAlaLeuAlaValGlyLeuGluLeuTrpAlaAla
GCGCACGCCTTGCCCGCCCAGGTGGCATTTACACCCTACGCCCCGGAG  192
AlaHisAlaLeuProAlaGlnValAlaPheThrProTyrAlaProGlu
CCCGGGAGCACATGCCGGCTCAGAGAATACTATGACCAGACAGCTCAG  240
ProGlySerThrCysArgLeuArgGluTyrTyrAspGlnThrAlaGln
ATGTGCTGCAGCAAATGCTCGCCGGGCCAACATGCAAAAGTCTTCTGT  288
MetCysCysSerLysCysSerProGlyGlnHisAlaLysValPheCys
ACCAAGACCTCGGACACCGTGTGTGACTCCTGTGAGGACAGCACATAC  336
ThrLysThrSerAspThrValCysAspSerCysGluAspSerThrTyr
ACCCAGCTCTGGAACTGGGTTCCCGAGTGCTTGAGCTGTGGCTCCCGC  384
ThrGlnLeuTrpAsnTrpValProGluCysLeuSerCysGlySerArg
TGTAGCTCTGACCAGGTGGAAACTCAAGCCTGCACTCGGGAACAGAAC  432
CysSerSerAspGlnValGluThrGlnAlaCysThrArgGluGlnAsn
CGCATCTGCACCTGCAGGCCCGGCTGGTACTGCGCGCTGAGCAAGCAG  480
ArgIleCysThrCysArgProGlyTrpTyrCysAlaLeuSerLysGln
GAGGGGTGCCGGCTGTGCGCGCCGCTGCGCAAGTGCCGCCCGGGCTTC  528
GluGlyCysArgLeuCysAlaProLeuArgLysCysArgProGlyPhe
GGCGTGGCCAGACCAGGAACTGAAACATCAGACGTGGTGTGCAAGCCC  576
GlyValAlaArgProGlyThrGluThrSerAspValValCysLysPro
```

TGTGCCCCGGGGACGTTCTCCAACACGACTTCATCCACGGATATTTGC 624
CysAlaProGlyThrPheSerAsnThrThrSerSerThrAspIleCys
AGGCCCCACCAGATCTGTAACGTGGTGGCCATCCCTGGGAATGCAAGC 672
ArgProHisGlnIleCysAsnValValAlaIleProGlyAsnAlaSer
ATGGATGCAGTCTGCACGTCCACGTCCCCCACCCGGAGTATGGCCCCA 720
MetAspAlaValCysThrSerThrSerProThrArgSerMetAlaPro
GGGGCAGTACACTTACCCCAGCCAGTGTCCACACGATCCCAACACACG 768
GlyAlaValHisLeuProGlnProValSerThrArgSerGlnHisThr
CAGCCAACTCCAGAACCCAGCACTGCTCCAAGCACCTCCTTCCTGCTC 816
GlnProThrProGluProSerThrAlaProSerThrSerPheLeuLeu
CCAATGGGCCCCAGCCCCCCAGCTGAAGGGAGCACTGGCGACGAGCCC 864
ProMetGlyProSerProProAlaGluGlySerThrGlyAspGluPro
AAATCTTGTGACAAAACTCACACATGCCCACCGTGCCCAGCACCTGAA 912
LysSerCysAspLysThrHisThrCysProProCysProAlaProGlu
CTCCTGGGGGGACCGTCAGTCTTCCTCTTCCCCCCAAAACCCAAGGAC 960
LeuLeuGLyGlyProSerValPheLeuPheProProLysProLysAsp
ACCCTCATGATCTCCCGGACCCCTGAGGTCACATGCGTGGTGGTGGAC 1008
ThrLeuMetIleSerArgThrProGluValThrCysValValValAsp
GTGAGCCACGAAGACCCTGAGGTCAAGTTCAACTGGTACGTGGACGGC 1056
ValSerHisGluAspProGluValLysPheAsnTrpTyrValAspGLy
GTGGAGGTGCATAATGCCAAGACAAAGCCGCGGGAGGAGCAGTACAAC 1104
ValGluValHisAsnAlaLysThrLysProArgGluGluGlnTyrAsn
AGCACGTACCGGGTGGTCAGCGTCCTCACCGTCCTGCACCAGGACTGG 1152
SerThrTyrArgValValSerValLeuThrValLeuHisGlnAspTrp
CTGAATGGCAAGGACTACAAGTGCAAGGTCTCCAACAAAGCCCTCCCA 1200
LeuAsnGlyLysAspTyrLysCysLysValSerAsnLysAlaLeuPro
GCCCCCATGCAGAAAACCATCTCCAAAGCCAAAGGGCAGCCCCGAGAA 1248
AlaProMetGlnLysThrIleSerLysAlaLysGlyGlnProArgGlu
CCACAGGTGTACACCCTGCCCCCATCCCGGGATGAGCTGACCAAGAAC 1296
ProGlnValTyrThrLeuProProSerArgAspGluLeuThrLysAsn
CAGGTCAGCCTGACCTGCCTGGTCAAAGGCTTCTATCCCAGGCACATC 1344
GlnValSerLeuThrCysLeuValLysGlyPheTyrProArgHisIle
GCCGTGGAGTGGGAGAGCAATGGGCAGCCGGAGAACAACTACAAGACC 1392
AlaValGluTrpGluSerAsnGlyGlnProGluAsnAsnTyrLysThr
ACGCCTCCCGTGCTGGACTCCGACGGCTCCTTCTTCCTCTACAGCAAG 1440
ThrProProValLeuAspSerAspGlySerPhePheLeuTyrSerLys
CTCACCGTGGACAAGAGCAGGTGGCAGCAGGGGAACGTCTTCTCATGC 1488
LeuThrValAspLysSerArgTrpGlnGlnGlyAsnValPheSerCys
TCCGTGATGCATGAGGCTCTGCACAACCACTACACGCAGAAGAGCCTC 1536
SerValMetHisGluAlaLeuHisAsnHisTyrThrGlnLysSerLeu
TCCCTGTCTCCGGGTAAATGA 1557
SerLeuSerProGlyLys

Polypeptide sequence

```
MLRLYVLVMGVSAFTLQPAAHTGAARSCRFRGRHYKREFRLEGE
PVALRCPQVPYWLWASVSPRINLTWHKNDSARTVPGEEETRMWAQDGALWLLPALQED
SGTYVCTTRNASYCDKMSIEFRVFENTDAFLPFISYPQILTLSTSGVLVCPDLSEFTR
DKTDVKXQWYRDSLLLDKDNEKFLSVRGTTHLLVHDVAQEDAGYYRCVLTFAHEGQQY
NITRSIELRIKKKKEETIPVIISPLKTISASLGSRLTIPCKVFLGTGTPLTTMLWWTA
NDTHIESAYPGGRVTEGPRQEYSENNENYIEVPLIFDPVTREDLHMDFKCVVHNTLSF
QTLRTTVKEASSTFSWGIVLAPLSLAFLVLGGIWMHRRCKHRTGKADGLTVLWPHHQD
FQSYPK
```

Polynucleotide sequence

```
cgggatcccg tgtcctctgg aagttgtcag gagcaatgtt gcgcttgtac gtgttggtaa   61
tgggagtttc tgccttcacc cttcagcctg cggcacacac aggggctgcc agaagctgcc  121
ggtttcgtgg gaggcattac aagcgggagt tcaggctgga aggggagcct gtagccctga  181
ggtgcccca ggtgccctac tggttgtggg cctctgtcag cccccgcatc aacctgacat   241
ggcataaaaa tgactctgct aggacggtcc caggagaaga agagacacgg atgtgggccc  301
aggacggtgc tctgtggctt ctgccagcct tgcaggagga ctctggcacc tacgtctgca  361
ctactagaaa tgcttcttac tgtgacaaaa tgtccattga gttcagagtc tttgagaata  421
cagatgcttt cctgccgttc atctcatacc cgcaaatttt aaccttgtca acctctgggg  481
tattagtatg ccctgacctg agtgaattca cccgtgacaa aactgacgtg aagattcaat  541
ggtacaggga ttctcttctt ttggataaag acaatgagaa atttctaagt gtgaggggga  601
ccactcactt actcgtacac gatgtggccc aggaagatgc tggctattac cgctgtgtcc  661
tgacatttgc ccatgaaggc cagcaataca acatcactag gagtattgag ctacgcatca  721
agaaaaaaaa agaagagacc attcctgtga tcatttcccc cctcaagacc atatcagctt  781
ctctggggtc aagactgaca atcccgtgta aggtgtttct gggaaccggc acacccttaa  841
ccaccatgct gtggtggacg gccaatgaca cccacataga gagcgcctac ccgggaggcc  901
gcgtgaccga ggggccacgc caggaatatt cagaaaataa tgagaactac attgaagtgc  961
cattgatttt tgatcctgtc acaagagagg atttgcacat ggattttaaa tgtgttgtcc 1021
ataataccct gagttttcag acactacgca ccacagtcaa ggaagcctcc tccacgttct 1081
cctggggcat tgtgctggcc ccactttcac tggccttctt ggttttgggg ggaatatgga 1141
tgcacagacg gtgcaaacac agaactggaa aagcagatgg tctgactgtg ctatggcctc 1201
atcatcaaga ctttcaatcc tatcccaagt gaaataaatg gaatgaaata attcaaacac 1261
aaaa
```

ATGGCGCCCGCCGCCCTCTGGGTCGCGCTGGTCGTCGAACTGCAGCTGTGGGCCACCGGG
Metalaproalaalaleutrpvalalaleuvalvalgluleuglnleutrpalathrgly CACACAGTGCCCGCCAAGGTTGTCTTGACACCCTACAAGCCAGAACCTGGGAACCAGTGC
histhrvalproalalysvalvalleuthrprotyrlysprogluproglyasnglncys CAGATCTCACAGGAGTACTATGACAAGAAGGCTCAGATGTGCTGTGCTAAGTGTCCCCCT
glnileserglnglutyrtyrasplyslysalaglnmetcyscysalalyscyspropro GGCCAGTATGCAAAACACTTCTGCAACAAGACTTCAGACACCGTGTGTGCGGACTGTGCG
glyglntyralalyshisphecysasnlysthrserasp thrvalcysalaaspcysala GCAGGCATGTTTACCCAGGTCTGGAACCATCTGCATACATGCCTGAGCTGCAGTTCTTCC
alaglymetphethrglnvaltrpasnhisleuhisthrcysleusercysserserser TGTAGTGATGACCAGGTGGAGACCCACAACTGCACTAAAAAACAGAACCGAGTGTGTGCT
cysseraspaspglnvalgluthrhisasncysthrlyslysglnasnargvalcysala TGCAACGCTGACAGTTACTGTGCCTTGAAATTGCATTCTGGGAACTGTCGACAGTGCATG
cysasnalaaspsertyrcysalaleulysleuhisserglyasncysargglncysmet AAGCTGAGCAAGTGTGGCCCTGGCTTCGGAGTGGCCCGTTCAAGAACCTCAAATGGAAAC
lysleuserlyscysglyproglypheglyvalalaargserargthrserasnglyasn GTGATATGCAGTGCCTGTGCCCCAGGGACGTTCTCTGACACCACATCATCCACAGATGTG
valilecysseralacysalaproglythrpheseraspthrthrserserthraspval TGCAGGCCCCACGGCATTTGTAGCATCCTGGCTATTCCTGGAAATGCAAGCACGGATGCA
cysargprohisglyilecysserileleualaileproglyasnalaserthraspala GTCTGTGCATCCGAGTCCCCAACTCCAAGCGCTGTTCCAAGGACAATCTACGTATCTCAG
valcysalasergluserprothrproseralavalproargthriletyrvalsergln CCAGAGCCCACAAGATCCCAGCCCATGGATCAAGAGCCAGGGCCTAGCCAAACTCCACAC
progluprothrargserglnprometaspglngluproglyproserglnthrprohis ATCCCTGTGTCCTTGGGTTCAACCCCCATCATTGAACCAAGCATCACGGGTGGG
ileprovalserleuglyserthrproileilegluproserilethrglygly

Fig. 4

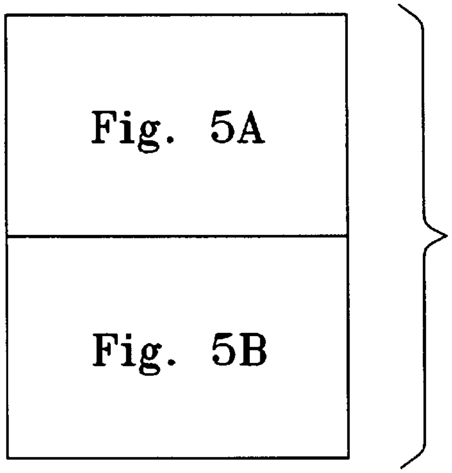

ClustalW Formatted Protein Aligment of TNFR ECDs

```
                          10        20        30
p80 ratTNFR ECD  MAPAALWVALVVELQLWATGHTVPAKVVLT
 p80 mTNFR ECD   MAPAALWVALVFELQLWATGHTVPAQVVLT
p75 huTNFR ECD   MAPVAVWAALAVGLELWAAAHALPAQVAFT

                          40        50        60
p80 ratTNFR ECD  PYKPXPGNQCQISQEYYDKXAQMCCAKCPP
 p80 mTNFR ECD   PYKPEPGYECQISQEYYDRKAQMCCAKCPP
p75 huTNFR ECD   PYAPEPGSTCRL-REYYDQTAQMCCSKCSP

                          70        80        90
p80 ratTNFR ECD  GQYAKHFCNKTSDTVCADCAAXMFTQVWNH
 p80 mTNFR ECD   GQYVKHFCNKTSDTVCADCEASMYTQVWNQ
p75 huTNFR ECD   GQHAKVFCTKTSDTVCDSCEDSTYTQLWNW
```

```
                    100                    110                    120
p80 ratTNFR ECD   L H T C L S C C S S C S D D Q V E X H N C T K K X N R V C G
p80 mTNFR   ECD   F R T C L S C C S S C T T D Q V E I R A C T K Q Q N R V C A
p75 huTNFR  ECD   V P E C L S C G E S R C S S D Q V E T Q A C T R E Q N R T C T

                    130                    140                    150
p80 ratTNFR ECD   C K A D S Y X A L K L H X G N C R Q C M K L S K I G P G F G
p80 mTNFR   ECD   C E A G R Y C A L K T H S G S C R Q C M R L S K C G P G F G
p75 huTNFR  ECD   C R P G W Y C A L S K Q E G - C R L C A P L R K C R P G F G

                    160                    170                    180
p80 ratTNFR ECD   V A R S R T S N G K V I C S A C A P G T F S D T T S S T D V
p80 mTNFR   ECD   V A S R A P N G N V L C K A C A P G T F S D T T S S T D V
p75 huTNFR  ECD   V A R P G T E T S D V V C K P C A P G T F S N T T S S T D

                    190                    200                    210
p80 ratTNFR ECD   C R P H G C S I L A R G N A S T D A V C A S E S P T P S
p80 mTNFR   ECD   C R P H R C S I L A I P G N A S T D A V C A P E S P T L S
p75 huTNFR  ECD   C R P H Q C N V V A I P G N A S M D A V C T S T P T R S

                    220                    230                    240
p80 ratTNFR ECD   A V P R T L Y V F Q P E P T R S Q P M D Q E P G X S Q T P -
p80 mTNFR   ECD   A N P R T L Y V S Q P E P T R S Q P L D Q E P G P S Q T P -
p75 huTNFR  ECD   M A P G A V H L P Q P V S T R S Q H T Q P T E P S T A P S

                    250                    260
p80 ratTNFR ECD   - H I P V S L G S T P I E P S L T G G
p80 mTNFR   ECD   - S I T S L G S T P I E Q S T K G G
p75 huTNFR  ECD   T S F L L P M G P S P P A E G S T G D
```

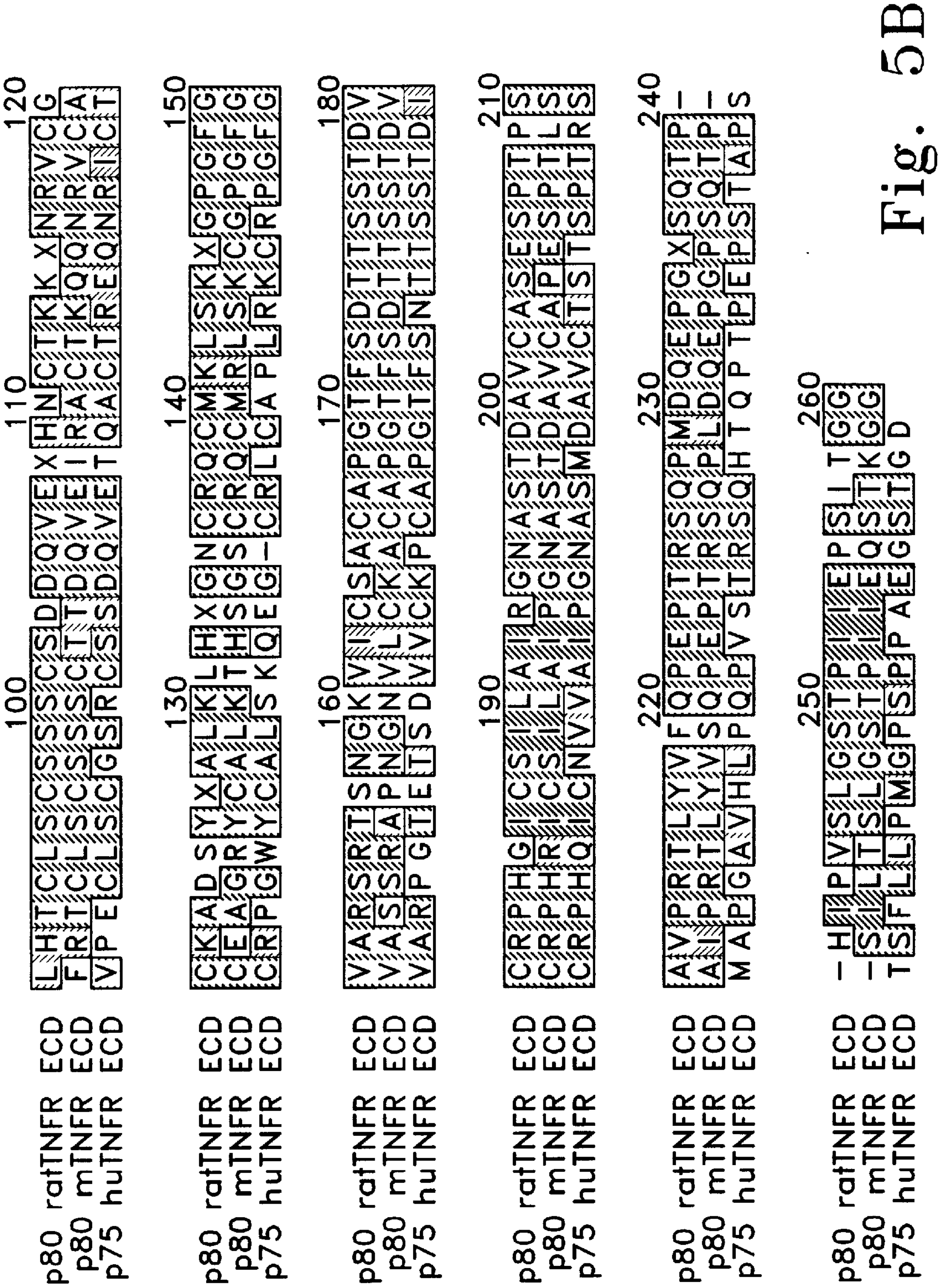

Fig. 5B

GTACCCAGAAACTGTGGAGGTGATTGCAAGCCTTGTATATGTACAGGCTCAGAAGTATCA
valproargasncysglyglyaspcyslysprocysilecysthrglysergluvalser TCTGTCTTCATCTTCCCCCCAAAGCCCAAAGATGTGCTCACCATCACTCTGACTCCTAAG
servalpheilepheproprolysprolysaspvalleuthrilethrleuthrprolys GTCACGTGTGTTGTGGTAGACATTAGCCAGGACGATCCCGAGGTCCATTTCAGCTGGTTT
valthrcysvalvalvalaspileserglnaspaspprogluvalhisphesertrpphe GTAGATGACGTGGAAGTCCACACAGCTCAGACTCGACCACCAGAGGAGCAGTTCAACAGC
valaspaspvalgluvalhisthralaglnthrargproprogluglunpheasnser ACTTTCCGCTCAGTCAGTGAACTCCCCATCCTGCACCAGGACTGGCTCAATGGCAGGACG
thrpheargservalsergluleuproileleuhisglnasptrpleuasnglyargthr TTCAGATGCAAGGTCACCAGTGCAGCTTTCCCATCCCCCATCGAGAAAACCATCTCCAAA
pheargcyslysvalthrseralaalapheproserproileglulysthrileserlys CCCGAAGGCAGAACACAAGTTCCGCATGTATACACCATGTCACCTACCAAGGAAGAGATG
progluglyargthrglnvalprohisvaltyrthrmetserprothrlysgluglumet ACCCAGAATGAAGTCAGTATCACCTGCATGGTAAAAGGCTTCTATCCCCCAGACATTTAT
thrglnasngluvalserilethrcysmetvallysglyphetyrproproaspiletyr GTGGAGTGGCAGATGAACGGGCAGCCACAGGAAAACTACAAGAACACTCCACCTACGATG
valglutrpglnmetasnglyglnproglngluasntyrlysasnthrproprothrmet GACACAGATGGGAGTTACTTCCTCTACAGCAAGCTCAATGTGAAGAAGGAAAAATGGCAG
aspthraspglysertyrpheleutyrserlysleuasnvallyslysglulystrpgln CAGGGAAACACGTTCACGTGTTCTGTGCTGCATGAAGGCCTGCACAACCACCATACTGAG
glnglyasnthrphethrcysservalleuhisgluglyleuhisasnhishisthrglu AAGAGTCTCTCCCACTCTCCGGGTAAATGA
lysserleuserhisserproglylys***

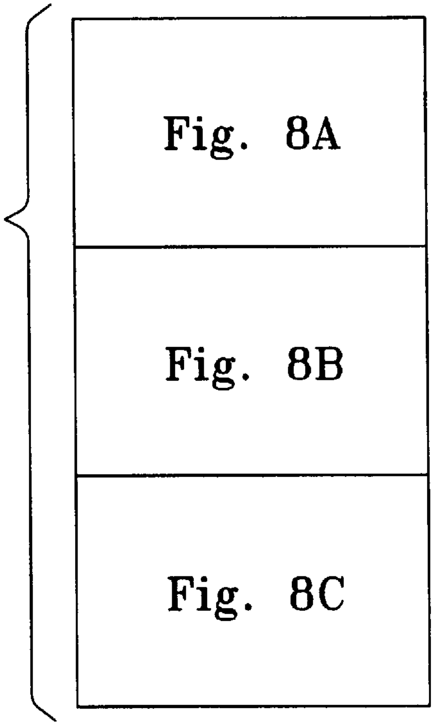

Fig. 8A

```
ATGGCGCCCGCCGCCCTCTGGGTCGCGCTGGTCGTCGAACTGCAGCTGTGGGCCACCGGG
Metalaproalaalaleutrpvalalaleuvalvalgluleuglnleutrpalathrgly

CACACAGTGCCCGCCAAGGTTGTCTTGACACCCTACAAGCCAGAACCTGGGAACCAGTGC
histhrvalproalalysvalvalleuthrprotyrlysprogluproglyasnglncys

CAGATCTCACAGGAGTACTATGACAAGAAGGCTCAGATGTGCTGTGCTAAGTGTCCCCCT
glnileserglnglutyrtyrasplyslysalaglnmetcyscysalalyscyspropro

GGCCAGTATGCAAAACACTTCTGCAACAAGACTTCAGACACCGTGTGTGCGGACTGTGCG
glyglntyralalyshisphecysasnlysthrseraspthrvalcysalaaspcysala

GCAGGCATGTTTACCCAGGTCTGGAACCATCTGCATACATGCCTGAGCTGCAGTTCTTCC
alaglymetphethrglnvaltrpasnhisleuhisthrcysleusercysserserser

TGTAGTGATGACCAGGTGGAGACCCACAACTGCACTAAAAACAGAACCGAGTGTGTGCT
cysseraspaspglnvalgluthrhisasncysthrlyslysglnasnargvalcysala
```

```
TGCAACGCTGACAGTTACTGTGCCTTGAAATTGCATTCTGGGAACTGTCGACAGTGCATG
cysasnalaaspsertyrcysalaleulysleuhisserglyasncysargglncysmet

AAGCTGAGCAAGTGTGGCCCTGGCTTCGGAGTGGCCCGTTCAAGAACCTCAAATGGAAAC
lysleuserlyscysglyproglypheglyvalalaargserargthrserasnglyasn

GTGATATGCAGTGCCTGTGCCCCAGGGACGTTCTCTGACACCACATCATCCACAGATGTG
valilecysseralacysalaproglythrpheseraspthrthrserserthraspval

TGCAGGCCCCACGGCATTTGTAGCATCCTGGCTATTCCTGGAAATGCAAGCACGGATGCA
cysargprohisglyilecysserileleualaileproglyasnalaserthraspala

GTCTGTGCATCCGAGTCCCCAACTCCAAGCGCTGTTCCAAGGACAATCTACGTATCTCAG
valcysalaserglusserprothrproseralavalproargthriletyrvalsergln

CCAGAGCCCACAAGATCCCAGCCCATGGATCAAGAGCCAGGGCCTAGCCAAACTCCACAC
progluprothrargserglnprometaspglngluproglyproserglnthrprohis

ATCCCTGTGTCCTTGGGTTCAACCCCCATCATTGAACCAAGCATCACGGGTGGGGTACCC
ileprovalserleuglyserthrproileilegluproserilethrglyglyvalpro

AGAAACTGTGGAGGTGATTGCAAGCCTTGTATATGTACAGGCTCAGAAGTATCATCTGTC
argasncysglyglyaspcyslysprocysilecysthrglysergluvalserserval

TTCATCTTCCCCCCAAAGCCCAAAGATGTGCTCACCATCACTCTGACTCCTAAGGTCACG
pheilepheproprolysprolysaspvalleuthrilethrleuthrprolysvalthr

TGTGTTGTGGTAGACATTAGCCAGGACGATCCCGAGGTCCATTTCAGCTGGTTTGTAGAT
cysvalvalvalaspileserglnaspaspprogluvalhisphesertrpphevalasp
```

Fig. 8B

GACGTGGAAGTCCACACAGCTCAGACTCGACCACCAGAGGAGCAGTTCAACAGCACTTTC
aspvalgluvalhisthralaglnthrargproprogluglnpheasnserthrphe CGCTCAGTCAGTGAACTCCCCATCCTGCACCAGGACTGGCTCAATGGCAGGACGTTCAGA
argservalsergluleuproileleuhisglnasptrpleuasnglyargthrphearg TGCAAGGTCACCAGTGCAGCTTTCCCATCCCCCATCGAGAAAACCATCTCCAAACCCGAA
cyslysvalthrseralaalapheproserproileglulysthrileserlysproglu GGCAGAACACAAGTTCCGCATGTATACACCATGTCACCTACCAAGGAAGAGATGACCCAG
glyargthrglnvalprohisvaltyrthrmetserprothrlysglugluметthrgln AATGAAGTCAGTATCACCTGCATGGTAAAAGGCTTCTATCCCCCAGACATTTATGTGGAG
asngluvalserilethrcysmetvallysglyphetyrproproaspiletyrvalglu TGGCAGATGAACGGGCAGCCACAGGAAAACTACAAGAACACTCCACCTACGATGGACACA
trpglnmetasnglyglnproglngluasntyrlysasnthrproprothrmetaspthr GATGGGAGTTACTTCCTCTACAGCAAGCTCAATGTGAAGAAGGAAAAATGGCAGCAGGGA
aspglysertyrpheleutyrserlysleuasnvallyslysglulystrpglnglngly AACACGTTCACGTGTTCTGTGCTGCATGAAGGCCTGCACAACCACCATACTGAGAAGAGT
asnthrphethrcysservalleuhisglyleuhisasnhishisthrglulysser CTCTCCCACTCTCCGGGTAAATGA
leuserhisserproglylys***

Fig. 8C

LOCALIZATION OF β-GAL WITHIN
JOINT TISSUES 4 DAYS AFTER i.a. rAAV

β-GAL STAINING IN ARTHRITIC JOINT 4 DAYS AFTER i.a. rAAV

β-GAL STAINING IN ARTHRITIC JOINT
4 DAYS AFTER i.a. PBS

Negative control: SCW treated rat, i.a. PBS (day 10), joint collected at day 14.

Note: this rat was injected i.a. with PBS in this joint (shown), and i.a. with rAAV-LacZ at the contralateral joint (not shown).

SEQUENCE LISTING

```
<160> NUMBER OF SEQ ID NOS: 20

<210> SEQ ID NO 1
<211> LENGTH: 518
<212> TYPE: PRT
<213> ORGANISM: Homo sapien

<400> SEQUENCE: 1

Ala Arg Gln Ala Ala Trp Arg Glu Gly Ala Gly Leu Arg Gly Arg Glu
 1               5                  10                  15

Gly Ala Arg Ala Gly Gly Asn Arg Thr Pro Pro Ala Ser Met Ala Pro
            20                  25                  30

Val Ala Val Trp Ala Ala Leu Ala Val Gly Leu Glu Leu Trp Ala Ala
        35                  40                  45

Ala His Ala Leu Pro Ala Gln Val Ala Phe Thr Pro Tyr Ala Pro Glu
    50                  55                  60

Pro Gly Ser Thr Cys Arg Leu Arg Glu Tyr Tyr Asp Gln Thr Ala Gln
```

-continued

```
65                  70                  75                  80

Met Cys Cys Ser Lys Cys Ser Pro Gly Gln His Ala Lys Val Phe Cys
                85                  90                  95

Thr Lys Thr Ser Asp Thr Val Cys Asp Ser Cys Glu Asp Ser Thr Tyr
            100                 105                 110

Thr Gln Leu Trp Asn Trp Val Pro Glu Cys Leu Ser Cys Gly Ser Arg
        115                 120                 125

Cys Ser Ser Asp Gln Val Glu Thr Gln Ala Cys Thr Arg Glu Gln Asn
    130                 135                 140

Arg Ile Cys Thr Cys Arg Pro Gly Trp Tyr Cys Ala Leu Ser Lys Gln
145                 150                 155                 160

Glu Gly Cys Arg Leu Cys Ala Pro Leu Arg Lys Cys Arg Pro Gly Phe
                165                 170                 175

Gly Val Ala Arg Pro Gly Thr Glu Thr Ser Asp Val Val Cys Lys Pro
            180                 185                 190

Cys Ala Pro Gly Thr Phe Ser Asn Thr Thr Ser Ser Thr Asp Ile Cys
        195                 200                 205

Arg Pro His Gln Ile Cys Asn Val Val Ala Ile Pro Gly Asn Ala Ser
    210                 215                 220

Met Asp Ala Val Cys Thr Ser Thr Ser Pro Thr Arg Ser Met Ala Pro
225                 230                 235                 240

Gly Ala Val His Leu Pro Gln Pro Val Ser Thr Arg Ser Gln His Thr
                245                 250                 255

Gln Pro Thr Pro Glu Pro Ser Thr Ala Pro Ser Thr Ser Phe Leu Leu
            260                 265                 270

Pro Met Gly Pro Ser Pro Pro Ala Glu Gly Ser Thr Gly Asp Glu Pro
        275                 280                 285

Lys Ser Cys Asp Lys Thr His Thr Cys Pro Pro Cys Pro Ala Pro Glu
    290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
            340                 345                 350

Val Glu Val His Asn Ala Lys Thr Lys Pro Arg Glu Glu Gln Tyr Asn
        355                 360                 365

Ser Thr Tyr Arg Val Val Ser Val Leu Thr Val Leu His Gln Asp Trp
    370                 375                 380

Leu Asn Gly Lys Asp Tyr Lys Cys Lys Val Ser Asn Lys Ala Leu Pro
385                 390                 395                 400

Ala Pro Met Gln Lys Thr Ile Ser Lys Ala Lys Gly Gln Pro Arg Glu
                405                 410                 415

Pro Gln Val Tyr Thr Leu Pro Pro Ser Arg Asp Glu Leu Thr Lys Asn
            420                 425                 430

Gln Val Ser Leu Thr Cys Leu Val Lys Gly Phe Tyr Pro Arg His Ile
        435                 440                 445

Ala Val Glu Trp Glu Ser Asn Gly Gln Pro Glu Asn Asn Tyr Lys Thr
    450                 455                 460

Thr Pro Pro Val Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495
```

-continued

```
Ser Val Met His Glu Ala Leu His Asn His Tyr Thr Gln Lys Ser Leu
            500                 505                 510

Ser Leu Ser Pro Gly Lys
        515


<210> SEQ ID NO 2
<211> LENGTH: 1557
<212> TYPE: DNA
<213> ORGANISM: Homo sapien
<220> FEATURE:
<221> NAME/KEY: CDS
<222> LOCATION: (1)...(1554)

<400> SEQUENCE: 2

gcg agg cag gca gcc tgg aga gaa ggc gct ggg ctg cga ggg cgc gag       48
Ala Arg Gln Ala Ala Trp Arg Glu Gly Ala Gly Leu Arg Gly Arg Glu
 1               5                  10                  15

ggc gcg agg gca ggg ggc aac cgg acc ccg ccc gca tcc atg gcg ccc       96
Gly Ala Arg Ala Gly Gly Asn Arg Thr Pro Pro Ala Ser Met Ala Pro
             20                  25                  30

gtc gcc gtc tgg gcc gcg ctg gcc gtc gga ctg gag ctc tgg gct gcg      144
Val Ala Val Trp Ala Ala Leu Ala Val Gly Leu Glu Leu Trp Ala Ala
         35                  40                  45

gcg cac gcc ttg ccc gcc cag gtg gca ttt aca ccc tac gcc ccg gag      192
Ala His Ala Leu Pro Ala Gln Val Ala Phe Thr Pro Tyr Ala Pro Glu
     50                  55                  60

ccc ggg agc aca tgc cgg ctc aga gaa tac tat gac cag aca gct cag      240
Pro Gly Ser Thr Cys Arg Leu Arg Glu Tyr Tyr Asp Gln Thr Ala Gln
 65                  70                  75                  80

atg tgc tgc agc aaa tgc tcg ccg ggc caa cat gca aaa gtc ttc tgt      288
Met Cys Cys Ser Lys Cys Ser Pro Gly Gln His Ala Lys Val Phe Cys
                 85                  90                  95

acc aag acc tcg gac acc gtg tgt gac tcc tgt gag gac agc aca tac      336
Thr Lys Thr Ser Asp Thr Val Cys Asp Ser Cys Glu Asp Ser Thr Tyr
            100                 105                 110

acc cag ctc tgg aac tgg gtt ccc gag tgc ttg agc tgt ggc tcc cgc      384
Thr Gln Leu Trp Asn Trp Val Pro Glu Cys Leu Ser Cys Gly Ser Arg
        115                 120                 125

tgt agc tct gac cag gtg gaa act caa gcc tgc act cgg gaa cag aac      432
Cys Ser Ser Asp Gln Val Glu Thr Gln Ala Cys Thr Arg Glu Gln Asn
    130                 135                 140

cgc atc tgc acc tgc agg ccc ggc tgg tac tgc gcg ctg agc aag cag      480
Arg Ile Cys Thr Cys Arg Pro Gly Trp Tyr Cys Ala Leu Ser Lys Gln
145                 150                 155                 160

gag ggg tgc cgg ctg tgc gcg ccg ctg cgc aag tgc cgc ccg ggc ttc      528
Glu Gly Cys Arg Leu Cys Ala Pro Leu Arg Lys Cys Arg Pro Gly Phe
                165                 170                 175

ggc gtg gcc aga cca gga act gaa aca tca gac gtg gtg tgc aag ccc      576
Gly Val Ala Arg Pro Gly Thr Glu Thr Ser Asp Val Val Cys Lys Pro
            180                 185                 190

tgt gcc ccg ggg acg ttc tcc aac acg act tca tcc acg gat att tgc      624
Cys Ala Pro Gly Thr Phe Ser Asn Thr Thr Ser Ser Thr Asp Ile Cys
        195                 200                 205

agg ccc cac cag atc tgt aac gtg gtg gcc atc cct ggg aat gca agc      672
Arg Pro His Gln Ile Cys Asn Val Val Ala Ile Pro Gly Asn Ala Ser
    210                 215                 220

atg gat gca gtc tgc acg tcc acg tcc ccc acc cgg agt atg gcc cca      720
Met Asp Ala Val Cys Thr Ser Thr Ser Pro Thr Arg Ser Met Ala Pro
225                 230                 235                 240

ggg gca gta cac tta ccc cag cca gtg tcc aca cga tcc caa cac acg      768
```

-continued

```
Gly Ala Val His Leu Pro Gln Pro Val Ser Thr Arg Ser Gln His Thr
                245                 250                 255

cag cca act cca gaa ccc agc act gct cca agc acc tcc ttc ctg ctc      816
Gln Pro Thr Pro Glu Pro Ser Thr Ala Pro Ser Thr Ser Phe Leu Leu
            260                 265                 270

cca atg ggc ccc agc ccc cca gct gaa ggg agc act ggc gac gag ccc      864
Pro Met Gly Pro Ser Pro Pro Ala Glu Gly Ser Thr Gly Asp Glu Pro
        275                 280                 285

aaa tct tgt gac aaa act cac aca tgc cca ccg tgc cca gca cct gaa      912
Lys Ser Cys Asp Lys Thr His Thr Cys Pro Pro Cys Pro Ala Pro Glu
    290                 295                 300

ctc ctg ggg gga ccg tca gtc ttc ctc ttc ccc cca aaa ccc aag gac      960
Leu Leu Gly Gly Pro Ser Val Phe Leu Phe Pro Pro Lys Pro Lys Asp
305                 310                 315                 320

acc ctc atg atc tcc cgg acc cct gag gtc aca tgc gtg gtg gtg gac     1008
Thr Leu Met Ile Ser Arg Thr Pro Glu Val Thr Cys Val Val Val Asp
                325                 330                 335

gtg agc cac gaa gac cct gag gtc aag ttc aac tgg tac gtg gac ggc     1056
Val Ser His Glu Asp Pro Glu Val Lys Phe Asn Trp Tyr Val Asp Gly
            340                 345                 350

gtg gag gtg cat aat gcc aag aca aag ccg cgg gag gag cag tac aac     1104
Val Glu Val His Asn Ala Lys Thr Lys Pro Arg Glu Glu Gln Tyr Asn
        355                 360                 365

agc acg tac cgg gtg gtc agc gtc ctc acc gtc ctg cac cag gac tgg     1152
Ser Thr Tyr Arg Val Val Ser Val Leu Thr Val Leu His Gln Asp Trp
    370                 375                 380

ctg aat ggc aag gac tac aag tgc aag gtc tcc aac aaa gcc ctc cca     1200
Leu Asn Gly Lys Asp Tyr Lys Cys Lys Val Ser Asn Lys Ala Leu Pro
385                 390                 395                 400

gcc ccc atg cag aaa acc atc tcc aaa gcc aaa ggg cag ccc cga gaa     1248
Ala Pro Met Gln Lys Thr Ile Ser Lys Ala Lys Gly Gln Pro Arg Glu
                405                 410                 415

cca cag gtg tac acc ctg ccc cca tcc cgg gat gag ctg acc aag aac     1296
Pro Gln Val Tyr Thr Leu Pro Pro Ser Arg Asp Glu Leu Thr Lys Asn
            420                 425                 430

cag gtc agc ctg acc tgc ctg gtc aaa ggc ttc tat ccc agg cac atc     1344
Gln Val Ser Leu Thr Cys Leu Val Lys Gly Phe Tyr Pro Arg His Ile
        435                 440                 445

gcc gtg gag tgg gag agc aat ggg cag ccg gag aac aac tac aag acc     1392
Ala Val Glu Trp Glu Ser Asn Gly Gln Pro Glu Asn Asn Tyr Lys Thr
    450                 455                 460

acg cct ccc gtg ctg gac tcc gac ggc tcc ttc ttc ctc tac agc aag     1440
Thr Pro Pro Val Leu Asp Ser Asp Gly Ser Phe Phe Leu Tyr Ser Lys
465                 470                 475                 480

ctc acc gtg gac aag agc agg tgg cag cag ggg aac gtc ttc tca tgc     1488
Leu Thr Val Asp Lys Ser Arg Trp Gln Gln Gly Asn Val Phe Ser Cys
                485                 490                 495

tcc gtg atg cat gag gct ctg cac aac cac tac acg cag aag agc ctc     1536
Ser Val Met His Glu Ala Leu His Asn His Tyr Thr Gln Lys Ser Leu
            500                 505                 510

tcc ctg tct ccg ggt aaa tga                                         1557
Ser Leu Ser Pro Gly Lys
        515


<210> SEQ ID NO 3
<211> LENGTH: 518
<212> TYPE: PRT
<213> ORGANISM: Homo sapien

<400> SEQUENCE: 3
```

-continued

```
Ala Arg Gln Ala Ala Trp Arg Glu Gly Ala Gly Leu Arg Gly Arg Glu
 1               5                  10                  15

Gly Ala Arg Ala Gly Gly Asn Arg Thr Pro Pro Ala Ser Met Ala Pro
            20                  25                  30

Val Ala Val Trp Ala Ala Leu Ala Val Gly Leu Glu Leu Trp Ala Ala
        35                  40                  45

Ala His Ala Leu Pro Ala Gln Val Ala Phe Thr Pro Tyr Ala Pro Glu
    50                  55                  60

Pro Gly Ser Thr Cys Arg Leu Arg Glu Tyr Tyr Asp Gln Thr Ala Gln
65                  70                  75                  80

Met Cys Cys Ser Lys Cys Ser Pro Gly Gln His Ala Lys Val Phe Cys
                85                  90                  95

Thr Lys Thr Ser Asp Thr Val Cys Asp Ser Cys Glu Asp Ser Thr Tyr
            100                 105                 110

Thr Gln Leu Trp Asn Trp Val Pro Glu Cys Leu Ser Cys Gly Ser Arg
        115                 120                 125

Cys Ser Ser Asp Gln Val Glu Thr Gln Ala Cys Thr Arg Glu Gln Asn
    130                 135                 140

Arg Ile Cys Thr Cys Arg Pro Gly Trp Tyr Cys Ala Leu Ser Lys Gln
145                 150                 155                 160

Glu Gly Cys Arg Leu Cys Ala Pro Leu Arg Lys Cys Arg Pro Gly Phe
                165                 170                 175

Gly Val Ala Arg Pro Gly Thr Glu Thr Ser Asp Val Val Cys Lys Pro
            180                 185                 190

Cys Ala Pro Gly Thr Phe Ser Asn Thr Thr Ser Ser Thr Asp Ile Cys
        195                 200                 205

Arg Pro His Gln Ile Cys Asn Val Val Ala Ile Pro Gly Asn Ala Ser
    210                 215                 220

Met Asp Ala Val Cys Thr Ser Thr Ser Pro Thr Arg Ser Met Ala Pro
225                 230                 235                 240

Gly Ala Val His Leu Pro Gln Pro Val Ser Thr Arg Ser Gln His Thr
                245                 250                 255

Gln Pro Thr Pro Glu Pro Ser Thr Ala Pro Ser Thr Ser Phe Leu Leu
            260                 265                 270

Pro Met Gly Pro Ser Pro Pro Ala Glu Gly Ser Thr Gly Asp Glu Pro
        275                 280                 285

Lys Ser Cys Asp Lys Thr His Thr Cys Pro Pro Cys Pro Ala Pro Glu
    290                 295                 300

Leu Leu Gly Gly Pro Ser Val Phe Leu Phe Pro Pro Lys Pro Lys Asp
305                 310                 315                 320

Thr Leu Met Ile Ser Arg Thr Pro Glu Val Thr Cys Val Val Val Asp
                325                 330                 335

Val Ser His Glu Asp Pro Glu Val Lys Phe Asn Trp Tyr Val Asp Gly
            340                 345                 350

Val Glu Val His Asn Ala Lys Thr Lys Pro Arg Glu Glu Gln Tyr Asn
        355                 360                 365

Ser Thr Tyr Arg Val Val Ser Val Leu Thr Val Leu His Gln Asp Trp
    370                 375                 380

Leu Asn Gly Lys Asp Tyr Lys Cys Lys Val Ser Asn Lys Ala Leu Pro
385                 390                 395                 400

Ala Pro Met Gln Lys Thr Ile Ser Lys Ala Lys Gly Gln Pro Arg Glu
                405                 410                 415

Pro Gln Val Tyr Thr Leu Pro Pro Ser Arg Asp Glu Leu Thr Lys Asn
```

-continued

```
            420                 425                 430

Gln Val Ser Leu Thr Cys Leu Val Lys Gly Phe Tyr Pro Arg His Ile
        435                 440                 445

Ala Val Glu Trp Glu Ser Asn Gly Gln Pro Glu Asn Asn Tyr Lys Thr
    450                 455                 460

Thr Pro Pro Val Leu Asp Ser Asp Gly Ser Phe Phe Leu Tyr Ser Lys
465                 470                 475                 480

Leu Thr Val Asp Lys Ser Arg Trp Gln Gln Gly Asn Val Phe Ser Cys
                485                 490                 495

Ser Val Met His Glu Ala Leu His Asn His Tyr Thr Gln Lys Ser Leu
            500                 505                 510

Ser Leu Ser Pro Gly Lys
        515


<210> SEQ ID NO 4
<211> LENGTH: 398
<212> TYPE: PRT
<213> ORGANISM: Homo sapien

<400> SEQUENCE: 4

Met Leu Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Phe Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Arg Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Gln Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270
```

-continued

Trp Trp Thr Ala Asn Asp Thr His Ile Glu Ser Ala Tyr Pro Gly Gly
275 280 285

Arg Val Thr Glu Gly Pro Arg Gln Glu Tyr Ser Glu Asn Asn Glu Asn
290 295 300

Tyr Ile Glu Val Pro Leu Ile Phe Asp Pro Val Thr Arg Glu Asp Leu
305 310 315 320

His Met Asp Phe Lys Cys Val Val His Asn Thr Leu Ser Phe Gln Thr
325 330 335

Leu Arg Thr Thr Val Lys Glu Ala Ser Ser Thr Phe Ser Trp Gly Ile
340 345 350

Val Leu Ala Pro Leu Ser Leu Ala Phe Leu Val Leu Gly Gly Ile Trp
355 360 365

Met His Arg Arg Cys Lys His Arg Thr Gly Lys Ala Asp Gly Leu Thr
370 375 380

Val Leu Trp Pro His His Gln Asp Phe Gln Ser Tyr Pro Lys
385 390 395

<210> SEQ ID NO 5
<211> LENGTH: 1264
<212> TYPE: DNA
<213> ORGANISM: Homo sapien

<400> SEQUENCE: 5
cgggatcccg tgtcctctgg aagttgtcag gagcaatgtt gcgcttgtac gtgttggtaa 60
tgggagtttc tgccttcacc cttcagcctg cggcacacac aggggctgcc agaagctgcc 120
ggtttcgtgg gaggcattac aagcgggagt tcaggctgga aggggagcct gtagccctga 180
ggtgccccca ggtgccctac tggttgtggg cctctgtcag cccccgcatc aacctgacat 240
ggcataaaaa tgactctgct aggacggtcc caggagaaga agagacacgg atgtgggccc 300
aggacggtgc tctgtggctt ctgccagcct tgcaggagga ctctggcacc tacgtctgca 360
ctactagaaa tgcttcttac tgtgacaaaa tgtccattga gttcagagtc tttgagaata 420
cagatgcttt cctgccgttc atctcatacc cgcaaatttt aaccttgtca acctctgggg 480
tattagtatg ccctgacctg agtgaattca cccgtgacaa aactgacgtg aagattcaat 540
ggtacaggga ttctcttctt ttggataaag acaatgagaa atttctaagt gtgaggggga 600
ccactcactt actcgtacac gatgtggccc aggaagatgc tggctattac cgctgtgtcc 660
tgacatttgc ccatgaaggc cagcaataca acatcactag gagtattgag ctacgcatca 720
agaaaaaaaa agaagagacc attcctgtga tcatttcccc cctcaagacc atatcagctt 780
ctctggggtc aagactgaca atcccgtgta aggtgtttct gggaaccggc acacccttaa 840
ccaccatgct gtggtggacg gccaatgaca cccacataga gagcgcctac ccgggaggcc 900
gcgtgaccga ggggccacgc caggaatatt cagaaaataa tgagaactac attgaagtgc 960
cattgatttt tgatcctgtc acaagagagg atttgcacat ggattttaaa tgtgttgtcc 1020
ataataccct gagttttcag acactacgca ccacagtcaa ggaagcctcc tccacgttct 1080
cctggggcat tgtgctggcc ccactttcac tggccttctt ggttttgggg ggaatatgga 1140
tgcacagacg gtgcaaacac agaactggaa aagcagatgg tctgactgtg ctatggcctc 1200
atcatcaaga ctttcaatcc tatcccaagt gaaataaatg gaatgaaata attcaaacac 1260
aaaa 1264

<210> SEQ ID NO 6
<211> LENGTH: 774

-continued

```
<212> TYPE: DNA
<213> ORGANISM: Rattus rattus
<220> FEATURE:
<221> NAME/KEY: CDS
<222> LOCATION: (1)...(774)

<400> SEQUENCE: 6

atg gcg ccc gcc gcc ctc tgg gtc gcg ctg gtc gtc gaa ctg cag ctg       48
Met Ala Pro Ala Ala Leu Trp Val Ala Leu Val Val Glu Leu Gln Leu
 1               5                  10                  15

tgg gcc acc ggg cac aca gtg ccc gcc aag gtt gtc ttg aca ccc tac       96
Trp Ala Thr Gly His Thr Val Pro Ala Lys Val Val Leu Thr Pro Tyr
            20                  25                  30

aag cca gaa cct ggg aac cag tgc cag atc tca cag gag tac tat gac      144
Lys Pro Glu Pro Gly Asn Gln Cys Gln Ile Ser Gln Glu Tyr Tyr Asp
        35                  40                  45

aag aag gct cag atg tgc tgt gct aag tgt ccc cct ggc cag tat gca      192
Lys Lys Ala Gln Met Cys Cys Ala Lys Cys Pro Pro Gly Gln Tyr Ala
    50                  55                  60

aaa cac ttc tgc aac aag act tca gac acc gtg tgt gcg gac tgt gcg      240
Lys His Phe Cys Asn Lys Thr Ser Asp Thr Val Cys Ala Asp Cys Ala
 65                  70                  75                  80

gca ggc atg ttt acc cag gtc tgg aac cat ctg cat aca tgc ctg agc      288
Ala Gly Met Phe Thr Gln Val Trp Asn His Leu His Thr Cys Leu Ser
                85                  90                  95

tgc agt tct tcc tgt agt gat gac cag gtg gag acc cac aac tgc act      336
Cys Ser Ser Ser Cys Ser Asp Asp Gln Val Glu Thr His Asn Cys Thr
            100                 105                 110

aaa aaa cag aac cga gtg tgt gct tgc aac gct gac agt tac tgt gcc      384
Lys Lys Gln Asn Arg Val Cys Ala Cys Asn Ala Asp Ser Tyr Cys Ala
        115                 120                 125

ttg aaa ttg cat tct ggg aac tgt cga cag tgc atg aag ctg agc aag      432
Leu Lys Leu His Ser Gly Asn Cys Arg Gln Cys Met Lys Leu Ser Lys
    130                 135                 140

tgt ggc cct ggc ttc gga gtg gcc cgt tca aga acc tca aat gga aac      480
Cys Gly Pro Gly Phe Gly Val Ala Arg Ser Arg Thr Ser Asn Gly Asn
145                 150                 155                 160

gtg ata tgc agt gcc tgt gcc cca ggg acg ttc tct gac acc aca tca      528
Val Ile Cys Ser Ala Cys Ala Pro Gly Thr Phe Ser Asp Thr Thr Ser
                165                 170                 175

tcc aca gat gtg tgc agg ccc cac ggc att tgt agc atc ctg gct att      576
Ser Thr Asp Val Cys Arg Pro His Gly Ile Cys Ser Ile Leu Ala Ile
            180                 185                 190

cct gga aat gca agc acg gat gca gtc tgt gca tcc gag tcc cca act      624
Pro Gly Asn Ala Ser Thr Asp Ala Val Cys Ala Ser Glu Ser Pro Thr
        195                 200                 205

cca agc gct gtt cca agg aca atc tac gta tct cag cca gag ccc aca      672
Pro Ser Ala Val Pro Arg Thr Ile Tyr Val Ser Gln Pro Glu Pro Thr
    210                 215                 220

aga tcc cag ccc atg gat caa gag cca ggg cct agc caa act cca cac      720
Arg Ser Gln Pro Met Asp Gln Glu Pro Gly Pro Ser Gln Thr Pro His
225                 230                 235                 240

atc cct gtg tcc ttg ggt tca acc ccc atc att gaa cca agc atc acg      768
Ile Pro Val Ser Leu Gly Ser Thr Pro Ile Ile Glu Pro Ser Ile Thr
                245                 250                 255

ggt ggg                                                              774
Gly Gly

<210> SEQ ID NO 7
<211> LENGTH: 258
<212> TYPE: PRT
```

-continued

<213> ORGANISM: Rattus rattus

<400> SEQUENCE: 7

```
Met Ala Pro Ala Ala Leu Trp Val Ala Leu Val Val Glu Leu Gln Leu
 1               5                  10                  15

Trp Ala Thr Gly His Thr Val Pro Ala Lys Val Val Leu Thr Pro Tyr
            20                  25                  30

Lys Pro Glu Pro Gly Asn Gln Cys Gln Ile Ser Gln Glu Tyr Tyr Asp
        35                  40                  45

Lys Lys Ala Gln Met Cys Cys Ala Lys Cys Pro Pro Gly Gln Tyr Ala
    50                  55                  60

Lys His Phe Cys Asn Lys Thr Ser Asp Thr Val Cys Ala Asp Cys Ala
65                  70                  75                  80

Ala Gly Met Phe Thr Gln Val Trp Asn His Leu His Thr Cys Leu Ser
                85                  90                  95

Cys Ser Ser Ser Cys Ser Asp Asp Gln Val Glu Thr His Asn Cys Thr
            100                 105                 110

Lys Lys Gln Asn Arg Val Cys Ala Cys Asn Ala Asp Ser Tyr Cys Ala
        115                 120                 125

Leu Lys Leu His Ser Gly Asn Cys Arg Gln Cys Met Lys Leu Ser Lys
    130                 135                 140

Cys Gly Pro Gly Phe Gly Val Ala Arg Ser Arg Thr Ser Asn Gly Asn
145                 150                 155                 160

Val Ile Cys Ser Ala Cys Ala Pro Gly Thr Phe Ser Asp Thr Thr Ser
                165                 170                 175

Ser Thr Asp Val Cys Arg Pro His Gly Ile Cys Ser Ile Leu Ala Ile
            180                 185                 190

Pro Gly Asn Ala Ser Thr Asp Ala Val Cys Ala Ser Glu Ser Pro Thr
        195                 200                 205

Pro Ser Ala Val Pro Arg Thr Ile Tyr Val Ser Gln Pro Glu Pro Thr
    210                 215                 220

Arg Ser Gln Pro Met Asp Gln Glu Pro Gly Pro Ser Gln Thr Pro His
225                 230                 235                 240

Ile Pro Val Ser Leu Gly Ser Thr Pro Ile Ile Glu Pro Ser Ile Thr
                245                 250                 255

Gly Gly
```

<210> SEQ ID NO 8
<211> LENGTH: 258
<212> TYPE: PRT
<213> ORGANISM: Rattus rattus
<220> FEATURE:
<221> NAME/KEY: VARIANT
<222> LOCATION: (1)...(258)
<223> OTHER INFORMATION: Xaa = Any Amino Acid

<400> SEQUENCE: 8

```
Met Ala Pro Ala Ala Leu Trp Val Ala Leu Val Val Glu Leu Gln Leu
 1               5                  10                  15

Trp Ala Thr Gly His Thr Val Pro Ala Lys Val Val Leu Thr Pro Tyr
            20                  25                  30

Lys Pro Xaa Pro Gly Asn Gln Cys Gln Ile Ser Gln Glu Tyr Tyr Asp
        35                  40                  45

Lys Xaa Ala Gln Met Cys Cys Ala Lys Cys Pro Pro Gly Gln Tyr Ala
    50                  55                  60

Lys His Phe Cys Asn Lys Thr Ser Asp Thr Val Cys Ala Asp Cys Ala
```

-continued

```
65                  70                  75                  80

Ala Xaa Met Phe Thr Gln Val Trp Asn His Leu His Thr Cys Leu Ser
                85                  90                  95

Cys Ser Ser Ser Cys Ser Asp Asp Gln Val Glu Xaa His Asn Cys Thr
            100                 105                 110

Lys Lys Xaa Asn Arg Val Cys Gly Cys Lys Ala Asp Ser Tyr Xaa Ala
        115                 120                 125

Leu Lys Leu His Xaa Gly Asn Cys Arg Gln Cys Met Lys Leu Ser Lys
    130                 135                 140

Xaa Gly Pro Gly Phe Gly Val Ala Arg Ser Arg Thr Ser Asn Gly Lys
145                 150                 155                 160

Val Ile Cys Ser Ala Cys Ala Pro Gly Thr Phe Ser Asp Thr Thr Ser
                165                 170                 175

Ser Thr Asp Val Cys Arg Pro His Gly Ile Cys Ser Ile Leu Ala Ile
            180                 185                 190

Arg Gly Asn Ala Ser Thr Asp Ala Val Cys Ala Ser Glu Ser Pro Thr
        195                 200                 205

Pro Ser Ala Val Pro Arg Thr Leu Tyr Val Phe Gln Pro Glu Pro Thr
    210                 215                 220

Arg Ser Gln Pro Met Asp Gln Glu Pro Gly Xaa Ser Gln Thr Pro His
225                 230                 235                 240

Ile Pro Val Ser Leu Gly Ser Thr Pro Ile Ile Glu Pro Ser Ile Thr
                245                 250                 255

Gly Gly


<210> SEQ ID NO 9
<211> LENGTH: 258
<212> TYPE: PRT
<213> ORGANISM: Mus musculus

<400> SEQUENCE: 9

Met Ala Pro Ala Ala Leu Trp Val Ala Leu Val Phe Glu Leu Gln Leu
 1               5                  10                  15

Trp Ala Thr Gly His Thr Val Pro Ala Gln Val Val Leu Thr Pro Tyr
            20                  25                  30

Lys Pro Glu Pro Gly Tyr Glu Cys Gln Ile Ser Gln Glu Tyr Tyr Asp
        35                  40                  45

Arg Lys Ala Gln Met Cys Cys Ala Lys Cys Pro Pro Gly Gln Tyr Val
    50                  55                  60

Lys His Phe Cys Asn Lys Thr Ser Asp Thr Val Cys Ala Asp Cys Glu
65                  70                  75                  80

Ala Ser Met Tyr Thr Gln Val Trp Asn Gln Phe Arg Thr Cys Leu Ser
                85                  90                  95

Cys Ser Ser Ser Cys Thr Thr Asp Gln Val Glu Ile Arg Ala Cys Thr
            100                 105                 110

Lys Gln Gln Asn Arg Val Cys Ala Cys Glu Ala Gly Arg Tyr Cys Ala
        115                 120                 125

Leu Lys Thr His Ser Gly Ser Cys Arg Gln Cys Met Arg Leu Ser Lys
    130                 135                 140

Cys Gly Pro Gly Phe Gly Val Ala Ser Ser Arg Ala Pro Asn Gly Asn
145                 150                 155                 160

Val Leu Cys Lys Ala Cys Ala Pro Gly Thr Phe Ser Asp Thr Thr Ser
                165                 170                 175

Ser Thr Asp Val Cys Arg Pro His Arg Ile Cys Ser Ile Leu Ala Ile
```

-continued

```
            180                 185                 190

Pro Gly Asn Ala Ser Thr Asp Ala Val Cys Ala Pro Glu Ser Pro Thr
        195                 200                 205

Leu Ser Ala Ile Pro Arg Thr Leu Tyr Val Ser Gln Pro Glu Pro Thr
    210                 215                 220

Arg Ser Gln Pro Leu Asp Gln Glu Pro Gly Pro Ser Gln Thr Pro Ser
225                 230                 235                 240

Ile Leu Thr Ser Leu Gly Ser Thr Pro Ile Ile Glu Gln Ser Thr Lys
                245                 250                 255

Gly Gly


<210> SEQ ID NO 10
<211> LENGTH: 257
<212> TYPE: PRT
<213> ORGANISM: Homo sapien

<400> SEQUENCE: 10

Met Ala Pro Val Ala Val Trp Ala Ala Leu Ala Val Gly Leu Glu Leu
 1               5                  10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp


<210> SEQ ID NO 11
<211> LENGTH: 690
<212> TYPE: DNA
<213> ORGANISM: Rattus rattus
```

-continued

```
<220> FEATURE:
<221> NAME/KEY: CDS
<222> LOCATION: (1)...(687)

<400> SEQUENCE: 11

gta ccc aga aac tgt gga ggt gat tgc aag cct tgt ata tgt aca ggc       48
Val Pro Arg Asn Cys Gly Gly Asp Cys Lys Pro Cys Ile Cys Thr Gly
 1               5                  10                  15

tca gaa gta tca tct gtc ttc atc ttc ccc cca aag ccc aaa gat gtg       96
Ser Glu Val Ser Ser Val Phe Ile Phe Pro Pro Lys Pro Lys Asp Val
            20                  25                  30

ctc acc atc act ctg act cct aag gtc acg tgt gtt gtg gta gac att      144
Leu Thr Ile Thr Leu Thr Pro Lys Val Thr Cys Val Val Val Asp Ile
        35                  40                  45

agc cag gac gat ccc gag gtc cat ttc agc tgg ttt gta gat gac gtg      192
Ser Gln Asp Asp Pro Glu Val His Phe Ser Trp Phe Val Asp Asp Val
    50                  55                  60

gaa gtc cac aca gct cag act cga cca cca gag gag cag ttc aac agc      240
Glu Val His Thr Ala Gln Thr Arg Pro Pro Glu Glu Gln Phe Asn Ser
 65                  70                  75                  80

act ttc cgc tca gtc agt gaa ctc ccc atc ctg cac cag gac tgg ctc      288
Thr Phe Arg Ser Val Ser Glu Leu Pro Ile Leu His Gln Asp Trp Leu
                85                  90                  95

aat ggc agg acg ttc aga tgc aag gtc acc agt gca gct ttc cca tcc      336
Asn Gly Arg Thr Phe Arg Cys Lys Val Thr Ser Ala Ala Phe Pro Ser
            100                 105                 110

ccc atc gag aaa acc atc tcc aaa ccc gaa ggc aga aca caa gtt ccg      384
Pro Ile Glu Lys Thr Ile Ser Lys Pro Glu Gly Arg Thr Gln Val Pro
        115                 120                 125

cat gta tac acc atg tca cct acc aag gaa gag atg acc cag aat gaa      432
His Val Tyr Thr Met Ser Pro Thr Lys Glu Glu Met Thr Gln Asn Glu
    130                 135                 140

gtc agt atc acc tgc atg gta aaa ggc ttc tat ccc cca gac att tat      480
Val Ser Ile Thr Cys Met Val Lys Gly Phe Tyr Pro Pro Asp Ile Tyr
145                 150                 155                 160

gtg gag tgg cag atg aac ggg cag cca cag gaa aac tac aag aac act      528
Val Glu Trp Gln Met Asn Gly Gln Pro Gln Glu Asn Tyr Lys Asn Thr
                165                 170                 175

cca cct acg atg gac aca gat ggg agt tac ttc ctc tac agc aag ctc      576
Pro Pro Thr Met Asp Thr Asp Gly Ser Tyr Phe Leu Tyr Ser Lys Leu
            180                 185                 190

aat gtg aag aag gaa aaa tgg cag cag gga aac acg ttc acg tgt tct      624
Asn Val Lys Lys Glu Lys Trp Gln Gln Gly Asn Thr Phe Thr Cys Ser
        195                 200                 205

gtg ctg cat gaa ggc ctg cac aac cac cat act gag aag agt ctc tcc      672
Val Leu His Glu Gly Leu His Asn His His Thr Glu Lys Ser Leu Ser
    210                 215                 220

cac tct ccg ggt aaa tga                                              690
His Ser Pro Gly Lys
225


<210> SEQ ID NO 12
<211> LENGTH: 229
<212> TYPE: PRT
<213> ORGANISM: Rattus rattus

<400> SEQUENCE: 12

Val Pro Arg Asn Cys Gly Gly Asp Cys Lys Pro Cys Ile Cys Thr Gly
 1               5                  10                  15

Ser Glu Val Ser Ser Val Phe Ile Phe Pro Pro Lys Pro Lys Asp Val
            20                  25                  30
```

-continued

```
Leu Thr Ile Thr Leu Thr Pro Lys Val Thr Cys Val Val Val Asp Ile
        35                  40                  45

Ser Gln Asp Asp Pro Glu Val His Phe Ser Trp Phe Val Asp Asp Val
    50                  55                  60

Glu Val His Thr Ala Gln Thr Arg Pro Pro Glu Glu Gln Phe Asn Ser
65                  70                  75                  80

Thr Phe Arg Ser Val Ser Glu Leu Pro Ile Leu His Gln Asp Trp Leu
                85                  90                  95

Asn Gly Arg Thr Phe Arg Cys Lys Val Thr Ser Ala Ala Phe Pro Ser
            100                 105                 110

Pro Ile Glu Lys Thr Ile Ser Lys Pro Glu Gly Arg Thr Gln Val Pro
        115                 120                 125

His Val Tyr Thr Met Ser Pro Thr Lys Glu Glu Met Thr Gln Asn Glu
    130                 135                 140

Val Ser Ile Thr Cys Met Val Lys Gly Phe Tyr Pro Pro Asp Ile Tyr
145                 150                 155                 160

Val Glu Trp Gln Met Asn Gly Gln Pro Gln Glu Asn Tyr Lys Asn Thr
                165                 170                 175

Pro Pro Thr Met Asp Thr Asp Gly Ser Tyr Phe Leu Tyr Ser Lys Leu
            180                 185                 190

Asn Val Lys Lys Glu Lys Trp Gln Gln Gly Asn Thr Phe Thr Cys Ser
        195                 200                 205

Val Leu His Glu Gly Leu His Asn His His Thr Glu Lys Ser Leu Ser
    210                 215                 220

His Ser Pro Gly Lys
225


<210> SEQ ID NO 13
<211> LENGTH: 1464
<212> TYPE: DNA
<213> ORGANISM: Rattus rattus
<220> FEATURE:
<221> NAME/KEY: CDS
<222> LOCATION: (1)...(1461)

<400> SEQUENCE: 13

atg gcg ccc gcc gcc ctc tgg gtc gcg ctg gtc gtc gaa ctg cag ctg       48
Met Ala Pro Ala Ala Leu Trp Val Ala Leu Val Val Glu Leu Gln Leu
 1               5                  10                  15

tgg gcc acc ggg cac aca gtg ccc gcc aag gtt gtc ttg aca ccc tac       96
Trp Ala Thr Gly His Thr Val Pro Ala Lys Val Val Leu Thr Pro Tyr
             20                  25                  30

aag cca gaa cct ggg aac cag tgc cag atc tca cag gag tac tat gac      144
Lys Pro Glu Pro Gly Asn Gln Cys Gln Ile Ser Gln Glu Tyr Tyr Asp
         35                  40                  45

aag aag gct cag atg tgc tgt gct aag tgt ccc cct ggc cag tat gca      192
Lys Lys Ala Gln Met Cys Cys Ala Lys Cys Pro Pro Gly Gln Tyr Ala
     50                  55                  60

aaa cac ttc tgc aac aag act tca gac acc gtg tgt gcg gac tgt gcg      240
Lys His Phe Cys Asn Lys Thr Ser Asp Thr Val Cys Ala Asp Cys Ala
 65                  70                  75                  80

gca ggc atg ttt acc cag gtc tgg aac cat ctg cat aca tgc ctg agc      288
Ala Gly Met Phe Thr Gln Val Trp Asn His Leu His Thr Cys Leu Ser
                 85                  90                  95

tgc agt tct tcc tgt agt gat gac cag gtg gag acc cac aac tgc act      336
Cys Ser Ser Ser Cys Ser Asp Asp Gln Val Glu Thr His Asn Cys Thr
            100                 105                 110
```

-continued

```
aaa aaa cag aac cga gtg tgt gct tgc aac gct gac agt tac tgt gcc       384
Lys Lys Gln Asn Arg Val Cys Ala Cys Asn Ala Asp Ser Tyr Cys Ala
        115                 120                 125

ttg aaa ttg cat tct ggg aac tgt cga cag tgc atg aag ctg agc aag       432
Leu Lys Leu His Ser Gly Asn Cys Arg Gln Cys Met Lys Leu Ser Lys
    130                 135                 140

tgt ggc cct ggc ttc gga gtg gcc cgt tca aga acc tca aat gga aac       480
Cys Gly Pro Gly Phe Gly Val Ala Arg Ser Arg Thr Ser Asn Gly Asn
145                 150                 155                 160

gtg ata tgc agt gcc tgt gcc cca ggg acg ttc tct gac acc aca tca       528
Val Ile Cys Ser Ala Cys Ala Pro Gly Thr Phe Ser Asp Thr Thr Ser
                165                 170                 175

tcc aca gat gtg tgc agg ccc cac ggc att tgt agc atc ctg gct att       576
Ser Thr Asp Val Cys Arg Pro His Gly Ile Cys Ser Ile Leu Ala Ile
            180                 185                 190

cct gga aat gca agc acg gat gca gtc tgt gca tcc gag tcc cca act       624
Pro Gly Asn Ala Ser Thr Asp Ala Val Cys Ala Ser Glu Ser Pro Thr
        195                 200                 205

cca agc gct gtt cca agg aca atc tac gta tct cag cca gag ccc aca       672
Pro Ser Ala Val Pro Arg Thr Ile Tyr Val Ser Gln Pro Glu Pro Thr
    210                 215                 220

aga tcc cag ccc atg gat caa gag cca ggg cct agc caa act cca cac       720
Arg Ser Gln Pro Met Asp Gln Glu Pro Gly Pro Ser Gln Thr Pro His
225                 230                 235                 240

atc cct gtg tcc ttg ggt tca acc ccc atc att gaa cca agc atc acg       768
Ile Pro Val Ser Leu Gly Ser Thr Pro Ile Ile Glu Pro Ser Ile Thr
                245                 250                 255

ggt ggg gta ccc aga aac tgt gga ggt gat tgc aag cct tgt ata tgt       816
Gly Gly Val Pro Arg Asn Cys Gly Gly Asp Cys Lys Pro Cys Ile Cys
            260                 265                 270

aca ggc tca gaa gta tca tct gtc ttc atc ttc ccc cca aag ccc aaa       864
Thr Gly Ser Glu Val Ser Ser Val Phe Ile Phe Pro Pro Lys Pro Lys
        275                 280                 285

gat gtg ctc acc atc act ctg act cct aag gtc acg tgt gtt gtg gta       912
Asp Val Leu Thr Ile Thr Leu Thr Pro Lys Val Thr Cys Val Val Val
    290                 295                 300

gac att agc cag gac gat ccc gag gtc cat ttc agc tgg ttt gta gat       960
Asp Ile Ser Gln Asp Asp Pro Glu Val His Phe Ser Trp Phe Val Asp
305                 310                 315                 320

gac gtg gaa gtc cac aca gct cag act cga cca cca gag gag cag ttc      1008
Asp Val Glu Val His Thr Ala Gln Thr Arg Pro Pro Glu Glu Gln Phe
                325                 330                 335

aac agc act ttc cgc tca gtc agt gaa ctc ccc atc ctg cac cag gac      1056
Asn Ser Thr Phe Arg Ser Val Ser Glu Leu Pro Ile Leu His Gln Asp
            340                 345                 350

tgg ctc aat ggc agg acg ttc aga tgc aag gtc acc agt gca gct ttc      1104
Trp Leu Asn Gly Arg Thr Phe Arg Cys Lys Val Thr Ser Ala Ala Phe
        355                 360                 365

cca tcc ccc atc gag aaa acc atc tcc aaa ccc gaa ggc aga aca caa      1152
Pro Ser Pro Ile Glu Lys Thr Ile Ser Lys Pro Glu Gly Arg Thr Gln
    370                 375                 380

gtt ccg cat gta tac acc atg tca cct acc aag gaa gag atg acc cag      1200
Val Pro His Val Tyr Thr Met Ser Pro Thr Lys Glu Glu Met Thr Gln
385                 390                 395                 400

aat gaa gtc agt atc acc tgc atg gta aaa ggc ttc tat ccc cca gac      1248
Asn Glu Val Ser Ile Thr Cys Met Val Lys Gly Phe Tyr Pro Pro Asp
                405                 410                 415

att tat gtg gag tgg cag atg aac ggg cag cca cag gaa aac tac aag      1296
Ile Tyr Val Glu Trp Gln Met Asn Gly Gln Pro Gln Glu Asn Tyr Lys
            420                 425                 430
```

-continued

```
aac act cca cct acg atg gac aca gat ggg agt tac ttc ctc tac agc     1344
Asn Thr Pro Pro Thr Met Asp Thr Asp Gly Ser Tyr Phe Leu Tyr Ser
        435                 440                 445

aag ctc aat gtg aag aag gaa aaa tgg cag cag gga aac acg ttc acg     1392
Lys Leu Asn Val Lys Lys Glu Lys Trp Gln Gln Gly Asn Thr Phe Thr
    450                 455                 460

tgt tct gtg ctg cat gaa ggc ctg cac aac cac cat act gag aag agt     1440
Cys Ser Val Leu His Glu Gly Leu His Asn His His Thr Glu Lys Ser
465                 470                 475                 480

ctc tcc cac tct ccg ggt aaa tga                                     1464
Leu Ser His Ser Pro Gly Lys
                485


<210> SEQ ID NO 14
<211> LENGTH: 487
<212> TYPE: PRT
<213> ORGANISM: Rattus rattus

<400> SEQUENCE: 14

Met Ala Pro Ala Ala Leu Trp Val Ala Leu Val Val Glu Leu Gln Leu
 1               5                  10                  15

Trp Ala Thr Gly His Thr Val Pro Ala Lys Val Val Leu Thr Pro Tyr
            20                  25                  30

Lys Pro Glu Pro Gly Asn Gln Cys Gln Ile Ser Gln Glu Tyr Tyr Asp
        35                  40                  45

Lys Lys Ala Gln Met Cys Cys Ala Lys Cys Pro Pro Gly Gln Tyr Ala
    50                  55                  60

Lys His Phe Cys Asn Lys Thr Ser Asp Thr Val Cys Ala Asp Cys Ala
65                  70                  75                  80

Ala Gly Met Phe Thr Gln Val Trp Asn His Leu His Thr Cys Leu Ser
                85                  90                  95

Cys Ser Ser Ser Cys Ser Asp Asp Gln Val Glu Thr His Asn Cys Thr
            100                 105                 110

Lys Lys Gln Asn Arg Val Cys Ala Cys Asn Ala Asp Ser Tyr Cys Ala
        115                 120                 125

Leu Lys Leu His Ser Gly Asn Cys Arg Gln Cys Met Lys Leu Ser Lys
    130                 135                 140

Cys Gly Pro Gly Phe Gly Val Ala Arg Ser Arg Thr Ser Asn Gly Asn
145                 150                 155                 160

Val Ile Cys Ser Ala Cys Ala Pro Gly Thr Phe Ser Asp Thr Thr Ser
                165                 170                 175

Ser Thr Asp Val Cys Arg Pro His Gly Ile Cys Ser Ile Leu Ala Ile
            180                 185                 190

Pro Gly Asn Ala Ser Thr Asp Ala Val Cys Ala Ser Glu Ser Pro Thr
        195                 200                 205

Pro Ser Ala Val Pro Arg Thr Ile Tyr Val Ser Gln Pro Glu Pro Thr
    210                 215                 220

Arg Ser Gln Pro Met Asp Gln Glu Pro Gly Pro Ser Gln Thr Pro His
225                 230                 235                 240

Ile Pro Val Ser Leu Gly Ser Thr Pro Ile Ile Glu Pro Ser Ile Thr
                245                 250                 255

Gly Gly Val Pro Arg Asn Cys Gly Gly Asp Cys Lys Pro Cys Ile Cys
            260                 265                 270

Thr Gly Ser Glu Val Ser Ser Val Phe Ile Phe Pro Pro Lys Pro Lys
        275                 280                 285
```

-continued

```
Asp Val Leu Thr Ile Thr Leu Thr Pro Lys Val Thr Cys Val Val Val
    290                 295                 300

Asp Ile Ser Gln Asp Asp Pro Glu Val His Phe Ser Trp Phe Val Asp
305                 310                 315                 320

Asp Val Glu Val His Thr Ala Gln Thr Arg Pro Pro Glu Glu Gln Phe
                325                 330                 335

Asn Ser Thr Phe Arg Ser Val Ser Glu Leu Pro Ile Leu His Gln Asp
            340                 345                 350

Trp Leu Asn Gly Arg Thr Phe Arg Cys Lys Val Thr Ser Ala Ala Phe
        355                 360                 365

Pro Ser Pro Ile Glu Lys Thr Ile Ser Lys Pro Glu Gly Arg Thr Gln
    370                 375                 380

Val Pro His Val Tyr Thr Met Ser Pro Thr Lys Glu Glu Met Thr Gln
385                 390                 395                 400

Asn Glu Val Ser Ile Thr Cys Met Val Lys Gly Phe Tyr Pro Pro Asp
                405                 410                 415

Ile Tyr Val Glu Trp Gln Met Asn Gly Gln Pro Gln Glu Asn Tyr Lys
            420                 425                 430

Asn Thr Pro Pro Thr Met Asp Thr Asp Gly Ser Tyr Phe Leu Tyr Ser
        435                 440                 445

Lys Leu Asn Val Lys Lys Glu Lys Trp Gln Gln Gly Asn Thr Phe Thr
    450                 455                 460

Cys Ser Val Leu His Glu Gly Leu His Asn His His Thr Glu Lys Ser
465                 470                 475                 480

Leu Ser His Ser Pro Gly Lys
                485


<210> SEQ ID NO 15
<211> LENGTH: 26
<212> TYPE: DNA
<213> ORGANISM: Rattus rattus

<400> SEQUENCE: 15

ctaacgacgt taacgatgca ggtgac                                            26


<210> SEQ ID NO 16
<211> LENGTH: 27
<212> TYPE: DNA
<213> ORGANISM: Rattus rattus

<400> SEQUENCE: 16

cggaattcgt gcccagaaac tgtggag                                           27


<210> SEQ ID NO 17
<211> LENGTH: 27
<212> TYPE: DNA
<213> ORGANISM: Rattus rattus

<400> SEQUENCE: 17

gctctagatc atttacccgg agagtgg                                           27


<210> SEQ ID NO 18
<211> LENGTH: 33
<212> TYPE: DNA
<213> ORGANISM: Rattus rattus

<400> SEQUENCE: 18

cataagggcc cgcaagagcg ggagctaccg ccg                                    33
```

-continued

```
<210> SEQ ID NO 19
<211> LENGTH: 30
<212> TYPE: DNA
<213> ORGANISM: Rattus rattus

<400> SEQUENCE: 19

ggtaccccac ccgtgatgct tggttcaatg                                   30


<210> SEQ ID NO 20
<211> LENGTH: 29
<212> TYPE: DNA
<213> ORGANISM: Rattus rattus

<400> SEQUENCE: 20

gggtacccag aaactgtgga ggtgattgc                                    29
```

METHODS AND COMPOSITION FOR LOWERING THE LEVEL OF TUMOR NECROSIS FACTOR (TNF) IN TNF-ASSOCIATED DISORDERS

CROSS-REFERENCE TO RELATED APPLICATIONS

This application claims the priority benefit of U.S. provisional patent application serial No. 60/150,688, filed May 28, 1999, which is incorporated by reference in its entirety.

STATEMENT OF RIGHTS TO INVENTIONS MADE UNDER FEDERALLY SPONSORED RESEARCH (Not Applicable).

FIELD OF INVENTION

This invention relates to the use of adeno-associated virus (AAV) vectors to lower levels of tumor necrosis factor (TNF). More specifically, the invention relates to AAV vectors encoding a TNF antagonist and methods of using the AAV vectors to reduce the levels of TNF in an individual.

BACKGROUND

Tumor necrosis factor-α (TNFα) and tumor necrosis factor-β (TNFβ) are homologous multifunctional cytokines; the great similarities in structural and functional characteristics of which have resulted in their collective description as tumor necrosis factor or "TNF." Activities generally ascribed to TNF include: release of other cytokines including IL-1, IL-6, GM-CSF, and IL-10, induction of chemokines, increase in adhesion molecules, growth of blood vessels, release of tissue destructive enzymes and activation of T cells. See, for example, Feldmann et al., 1997, *Adv. Immunol.,* 64:283–350, Nawroth et al., 1986, *J. Exp. Med.,* 163:1363–1375; Moser et al., 1989, *J. Clin. Invest.,* 83:444–455; Shingu et al., 1993, *Clin. Exp. Immunol.* 94:145–149; MacNaul et al., 1992, *Matrix Suppl.,* 1:198–199; and Ahmadzadeh et al., 1990, *Clin. Exp. Rheumatol.* 8:387–391. All of these activities can serve to enhance an inflammatory response.

TNF initiates its biological effect through its interaction with specific, cell surface receptors on TNF-responsive cells. There are two distinct forms of the cell surface tumor necrosis factor receptor (TNFR), designated p75 (or Type II) and p55 (or Type I) (Smith et al., 1990, *Science* 248:1019–1023; Loetscher et al., 1990, *Cell* 61:351–359). TNFR Type I and TNFR Type II each bind to both TNFα and TNFβ. Soluble, truncated versions of the TNFRs with a ligand-binding domain are present in body fluids and joints (Engelmann et al., 1989, *J. Biol. Chem.* 264:11974–11980; Roux-Lombard et al., 1993, *Arthritis Rheum.* 36:485–489).

A number of disorders are associated with elevated levels of TNF, many of them of significant medical importance. Among such TNF-associated disorders are congestive heart failure, inflammatory bowel diseases (including Crohn's disease), arthritis and asthma.

TNF appears to effect the heart and endothelium in congestive heart failure and has been implicated in the initiation of an apoptotic process in cardiac myocytes. The role for TNF in this disease is also supported by a temporal association between TNF activation and a transition from asymptomatic to symptomatic congestive heart failure (Ceconi et al., 1998, *Prog. Cardiovasc. Dis.* 41:25–30).

Inflammatory bowel diseases, such as Crohn's disease and ulcerative colitis, are associated with increased expression of TNF (Evans et al., 1997, *Aliment. Pharmacol. Ther.* 11:1031–1035). Treatment of such disorders have included the widespread use of immunosuppressive agents, such as azathioprine, methotrexate, cyclosporine and glucocorticosteroids (Rutgeerts, 1998, *Digestion* 59:453–469).

Arthritis is a common crippling condition for which there are no cures and few effective therapies. Approximately one in seven people in the United States are affected by one or more forms of arthritis. Most forms of arthritis are characterized by chronic inflammation of joints resulting from infection, mechanical injury, or immunological disturbance. Rheumatoid arthritis (RA) is a chronic inflammatory disease primarily manifest in the joints by swelling, pain, stiffness, and tissue destruction (Harris, 1990, *N. Engl. J. Med,* 323:994–996). Systemic manifestations can include elevations in serum levels of acute phase proteins, fever, mild anemia, thrombocytosis, and granulocytosis. In affected joints, there is a synovitis characterized by hyperplasia and inflammation of the synovium with an inflammatory exudate into the joint cavity, leading to erosion of cartilage and bone.

Although rheumatoid arthritis is not directly and imminently life threatening, recent data suggest that RA results in significantly shorter lifespan, and puts an enormous toll on the both the health system, the overall economy due to lost productivity, as well as quality of life resulting from restricted mobility and activities (Schiff, 1997, *Am. J. Med.,* 102(1A):11S–15S).

Current commonly employed therapeutics for treatment of RA fall primarily in three categories: non-steroidal anti-inflammatory drugs (NSAIDs), disease-modifying anti-rheumatic drugs (DMARDs), and immunosuppressives. NSAIDs are a large group of drugs often used as first line therapy for rheumatoid arthritis. The compounds act primarily through blockade of cyclooxygenase which catalyzes conversion of arachidonic acid to prostaglandins and thromboxanes. As a class, DMARDs, including agents such as gold, sulfasalazine, hydroxychloroquine, and D-penicillamine, are slow acting, quite toxic and there is little evidence that any of these compounds have mitigating effects on the underlying disease. NSAIDs can relieve some of the signs of inflammation and pain associated with arthritis; however, they appear to be ineffective against the immune system and in blocking progression of joint destruction and disease. Immunosuppressive agents, such as corticosteroids and methotrexate, are commonly used in the treatment of RA for suppressing the immune system and thus having an anti-inflammatory effect. However, these agents engender serious systemic toxicity which limits their use and effectiveness.

Although it is widely accepted that RA is an immune-based inflammatory disease, the antigen(s) which trigger the disease remain unknown. This has led to a large number of approaches to therapy under pre-clinical or clinical investigation which involve attempts to modulate the immune response system as a whole. Examples of several general efforts in this direction are highlighted below.

The mechanism of action of NSAIDs has been linked to blocking of cyclooxygenase, an enzyme with both an inducible and a constitutive form. As the inducible form of cyclooxygenase appears to be elevated in inflammatory disease, investigation into compounds selective for the inducible form are underway. In addition, attempts to devise vaccines to treat ongoing arthritis have been made with the use of peptide vaccines directed toward MHC class II or T cell receptor proteins. Generally, it has been proven difficult to demonstrate efficacy of vaccines administered to ongoing disease.

Much of the tissue destruction in RA appears to be due to various metalloproteinases. This group of proteases are believed to be central to the degradation of collagen II and proteoglycan seen in arthritis. A number of inhibitors of various of these enzymes are under pre-clinical or clinical investigation.

A number of broadly immunosuppressive drugs are in clinical testing for use in rheumatoid arthritis, including cyclosporine A and mycophenolate mofetil. As a wide range of cytokines are found in arthritic joints, anti-arthritis therapies have targeted cytokine pathways including those of IL-1, IL-2, IL-4, IL-10, IL-11, TGFβ, and TNFα, as well as, chemokine pathways (Feldmann et al., 1997). In particular, proinflammatory pathways of IL-1 have been targeted both by attack of IL-1 directly and via the naturally occurring interleukin-1 receptor antagonist molecule.

Methods of administering drug therapy for RA have included, and have been proposed to include, systemic or local delivery of a therapeutic drug and, in the case of proposed gene therapies, of a therapeutic gene. To date, such treatments have fallen short of delivering effective, safe therapy for arthritis for a variety of reasons, including: systemic side effects of many drugs, rapid clearance of therapeutic molecules from injected joints and/or circulation, inefficiency in DNA integration and expression from the genome, limited target cell population associated with some viral delivery vectors, transient gene expression associated with viral vectors which do not readily integrate and induction of an immune response associated with the gene delivery virus.

Use of TNF antagonists, such as soluble TNFRs and anti-TNF antibodies, has shown that a blockade of TNF can reverse effects attributed to TNF including decreases in IL-1, GM-CSF, IL-6, IL-8, adhesion molecules and tissue destruction (Feldmann et al., 1997). Such pleiotropic effects apparently due to the blockade of TNF alone suggests that TNF may lie near the top of the cascade of cytokine mediated events. Elevated levels of TNF-α are found in the synovial fluid of RA patients (Camussi and Lupia, 1998, *Drugs* 55:613–620).

The effect of TNF blockade utilizing a hamster anti-mouse TNF antibody was tested in a model of collagen type II arthritis in DBA/1 mice (Williams et al., 1992, *Proc. Natl. Acad. Sci. USA,* 89:9784–9788). Treatment initiated after the onset of disease resulted in improvement in footpad swelling, clinical score, and histopathology of joint destruction. Other studies have obtained similar results using either antibodies (Thorbecke et al., 1992, *Proc. Natl. Acad. Sci. USA,* 89:7375–7379) or TNFR constructs (Husby et al., 1988, *J. Autoimmun.* 1:363–71; Tetta et al., 1990, *Ann. Rheum. Dis.* 49:665–667; Wooley et al., 1993, *J. Immunol.* 151:6602–6607; Piguet et al., 1992, *Immunology* 77:510–514).

Similar results have also been obtained in other animal models of ongoing arthritis. In the rabbit, anti-TNFα antibody was shown to have an anti-arthritic effect on antigen induced arthritis (Lewthwaite et al., 1995, *Ann. Rheum. Dis.* 54:366–374). In the rat, anti-TNF therapy has been demonstrated to be effective in adjuvant (Mycobacterium) arthritis (Issekutz et al., 1994, *Clin. Exp. Immunol.* 97:26–32), in streptococcal cell wall induced arthritis (Schimmer et al., 1997, *J. Immunol.* 159:4103–4108) and in collagen induced arthritis (Le et al., 1997, *Arthritis Rheum.* 40:1662–1669).

In the studies described above, the TNF blockade was achieved by systemic delivery of the blocking agent. In a rat collagen arthritis model, delivery of a TNFR gene using an adenoviral vector resulted in transient production of serum levels of TNFR (up to 8 days) and a significant decrease in disease progression when the adenovirus was given to animals undergoing active arthritis (Le et al., 1997). Attempts to deliver the gene directly to the joint were unsuccessful, however, and resulted in an inflammatory reaction to the adenovirus.

A monoclonal antibody directed against TNFα (infliximab, REMICADE, Centocor), administered with and without methotrexate, has demonstrated clinical efficacy in the treatment of RA (Elliott et al., 1993, *Arthritis Rheum.* 36:1681–1690; Elliott et al., 1994, *Lancet* 344:1105–1110). These data demonstrate significant reductions in Paulus 20% and 50% criteria at 4, 12 and 26 weeks. This treatment is administered intravenously and the anti-TNF monoclonal antibody disappears from circulation over a period of two months. The duration of efficacy appears to decrease with repeated doses. The patient can generate antibodies against the anti-TNF antibodies which limit the effectiveness and duration of this therapy (Kavanaugh et al., 1998, *Rheum. Dis. Clin. North Am.* 24:593–614). Administration of methotrexate in combination with infliximab helps prevent the development of anti-infliximab antibodies (Maini et al., 1998, *Arthritis Rheum.* 41:1552–1563). Infliximab has also demonstrated clinical efficacy in the treatment of the inflammatory bowel disorder Crohn's disease (Baert et al., 1999, *Gastroenterology* 116:22–28).

Clinical trials of a recombinant version of the soluble human TNFR (p75) linked to the Fc portion of human IgG1 (sTNFR(p75):Fc, ENBREL, Immunex) have shown that its administration resulted in significant and rapid reductions in RA disease activity (Moreland et al., 1997, *N. Eng. J. Med.,* 337:141–147). In addition, preliminary safety data from an ongoing pediatric clinical trial for sTNFR(p75):Fc indicates that this drug is generally well-tolerated by patients with juvenile rheumatoid arthritis (JRA) (Garrison et al, 1998, Am. College of Rheumatology meeting, Nov. 9, 1998, abstract 584).

As noted above, ENBREL is a dimeric fusion protein consisting of the extracellular ligand-binding portion of the human 75 kilodalton (p75) TNFR linked to the Fc portion of human IgG1. The Fc component of ENBREL contains the CH2 domain, the CH3 domain and hinge region, but not the CH1 domain of IgG1. ENBREL is produced in a Chinese hamster ovary (CHO) mammalian cell expression system. It consists of 934 amino acids and has an apparent molecular weight of approximately 150 kilodaltons (Smith et al., 1990, *Science* 248:1019–1023; Mohler et al., 1993, *J. Immunol.* 151:1548–1561; U.S. Pat. No. 5,395,760 (Immunex Corporation, Seattle, Wash.); U.S. Pat. No. 5,605,690 (Immunex Corporation, Seattle, Wash.).

Approved by the Food and Drug administration (FDA) (Nov. 2, 1998), ENBREL is currently indicated for reduction in signs and symptoms of moderately to severely active rheumatoid arthritis in patients who have had an inadequate response to one or more disease-modifying antirheumatic drugs (DMARDs). ENBREL can be used in combination with methotrexate in patients who do not respond adequately to methotrexate alone. ENBREL is also indicated for reduction in signs and symptoms of moderately to severely active polyarticular-course juvenile rheumatoid arthritis in patients who have had an inadequate response to one or more DMARDs (May 28, 1999). ENBREL is given to RA patients at 25 mg twice weekly as a subcutaneous injection.

Currently, treatments using the sTNFR(p75):Fc (ENBREL, Immunex) preparations, including those described above, are administered subcutaneously twice weekly, which is costly, unpleasant and inconvenient for the patient. “Important Drug Warning” on World Wide Web at fda.gov/medwatch/safety/1999/enbrel.htm; “New Warning For Arthritis Drug, ENBREL” on World Wide Web at fda.gov/bbs/topics/ANSWERS/ANS00954.html; “ENBREL Injections Difficult for Some Patients” at dailynews.yahoo.com/h/nm/20000516/hl/arthritis_drugs_1.html. Further, relief afforded by this treatment is not sustained. Symptoms associated with an arthritic condition are reduced during treatment with sTNFR(p75):Fc but return upon discontinuation of this therapy, generally within one month. Complications have arisen, including local reactions at the site of injection. Moreover, long-term systemic exposure to this TNF-α antagonist can impose a risk for increased viral and bacterial infections and possibly cancer. Since this product was first introduced, serious infections, some involving death, have been reported in patients using ENBREL. “Product Information” on World Wide Web at enbrel.com/patient/html/patpi.htm; “Proven Tolerability” on World Wide Web at enbrel.com/patient/html/patsafety.htm.

Additional relevant references include: U.S. Pat. Nos. 5,858,775; 5,858,355; 5,858,351; 5,846,528; 5,843,742; 5,792,751; 5,786,211; 5,780,447; 5,766,585; 5,633,145; International Patent publications WO 95/16353; WO 94/20517; WO 92/11359; Schwarz, 1998, Keystone Symp., January 23–29, abstract 412; Song et al. (1998) *J. Clin. Invest.* 101:2615–2621; Ghivizzani et al., 1998, *Proc. Natl. Acad. Sci. USA* 95:4613–4618; Kang et al., 1997, *Biochemical Society Transactions* 25:533–537; Robbins et al., 1997, *Drug News & Perspect.* 10:283–292; Firestein et al., 1997, *N. Eng. J. Med.* 337:195–197; Muller-Ladner et al., 1997, *J. Immunol.* 158:3492–3498; and Pelletier et al., 1997, *Arthritis Rheum.* 40:1012–1019.

There is a need for new, effective forms of treatment for TNF-associated disorders such as RA, particularly treatments that can provide sustained, controlled therapy. The present invention provides compositions and methods for effective and continuous treatment of inflammatory processes of arthritis and other TNF-associated disorders.

All publications and references cited herein are hereby incorporated by reference in their entirety.

SUMMARY OF THE INVENTION

The present invention is directed to compositions and methods for reducing TNF levels and/or treatment of TNF-associated disorders of a mammal. The compositions generally comprise a recombinant adeno-associated virus (rAAV) vector that contains a polynucleotide encoding a TNF antagonist. The methods generally employ an rAAV vector to deliver a polynucleotide encoding a TNF antagonist to the mammal, which in turn reduces the levels of TNF and results in palliation of a number of TNF-associated disorders, such as arthritis (including RA), Crohn's disease, asthma and congestive heart failure. Lowering TNF may in turn reduce levels of other disease causing or contributing agents, such as other inflammatory cytokines. Lowering the levels of soluble TNF in joints exhibiting RA can in turn palliate TNF-associated conditions, such as arthritis, and can reduce an inflammatory response in the joints.

A preferred polynucleotide for the invention in the rAAV vectors described herein is one encoding a tumor necrosis factor receptor (TNFR). Since TNFR is capable of binding to soluble TNF, the introduction of TNFR tends to reduce the levels of TNF in circulation and/or the affected tissues, such as the joint. In some embodiments, the invention provides an rAAV vector comprising a polynucleotide encoding a p75 TNFR polypeptide. In other embodiments, the rAAV vectors of the invention comprise a polynucleotide encoding an Fc (constant domain of an immunoglobulin molecule):p75 fusion polypeptide. In other embodiments, the rAAV vectors of the invention comprise a polynucleotide encoding a fusion polypeptide in which the extracellular domain of TNFR is fused to Fc.

In some embodiments, the rAAV vectors of the invention further comprise a polynucleotide encoding an IL-1 antagonist, such as an IL-1 receptor type II polypeptide.

In another aspect, the invention provides methods for reducing TNF levels in a mammal, which comprise administering (i.e., delivering) any of the rAAV vectors described herein to the mammal in an amount sufficient to reduce TNF levels. In some embodiments, the delivery of an rAAV vector is in an arthritic joint. In some embodiments, these methods further comprise administering a TNF antagonist.

In another aspect, the invention provides methods for reducing an inflammatory response in a mammal, which comprise administering (i.e., delivering) any of the rAAV vectors described herein to the mammal in an amount sufficient to reduce the inflammatory response. In some embodiments, these methods further comprise administering a TNF antagonist.

In another aspect, the invention provides methods for palliating a TNF-associated disoreder, such as an arthritic condition occurring in a mammal, which comprise administering (i.e., delivering) any of the rAAV vectors described herein to the mammal in an amount sufficent to palliate the disorder (such as arthritic condition). In some embodiments, these methods further comprise administering a TNF antagonist.

BRIEF DESCRIPTION OF THE FIGURES

FIG. 1 depicts the amino acid sequence of a TNFR:Fc fusion polypeptide (SEQ ID NO:1) from U.S. Pat. No. 5,605,690.

FIGS. 2A and 2B depicts the polynucleotide and amino acid sequences of a TNFR:Fc fusion polypeptide from U.S. Pat. No. 5,605,690.

FIG. 3 depicts the amino acid and polynucleotide sequences of a human IL-1R type II (SEQ ID NO: 4, 5) from GenBank U74649.

FIG. 4 depicts the nucleotide and amino acid sequences of rat TNFR (p80) extracellular domain (ECD) (SEQ ID NO: 6, 7).

FIGS. 5A and 5B depicts the amino acid sequence alignment of rat TNFR (p80) ECD, murine TNFR (p80) ECD and human TNFR (p75) ECD.

FIG. 7 depicts the nucleotide and amino acid sequences of rat IgG1Fc (SEQ ID NO: 11, 12).

FIGS. 8A, 8B and 8C depicts the nucleotide and amino acid sequences of rat TNFR:Fc fusion construct.

DETAILED DESCRIPTION

Figure 6:
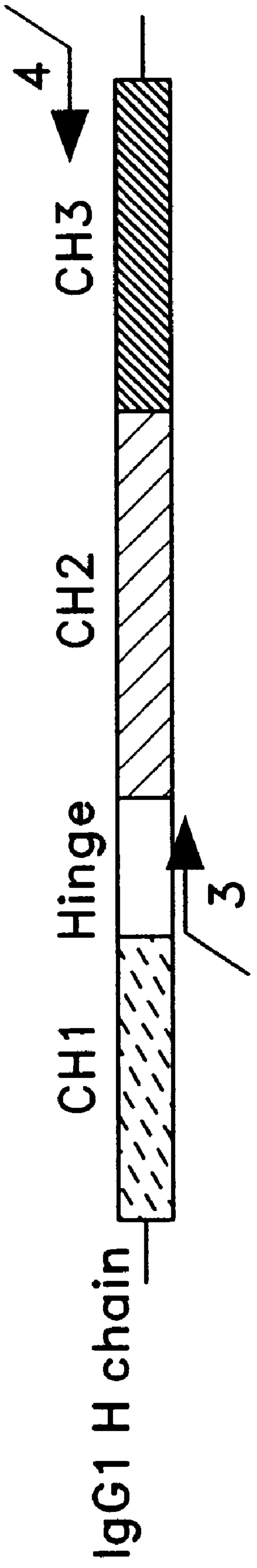
FIG. 6 depicts a diagram of the rat IgG1 heavy chain cDNA and the relative location of the PCR primers used to amplify the Fc portion of the IgG1 cDNA.

We have discovered compositions and methods for reducing levels of TNF in a tissue, a particular anatomical site and/or the circulation of an individual and methods for lowering TNF levels and for palliating TNF-associated disorders. Included are methods for reducing inflammatory response in a subject by reducing levels of TNF activity.

The invention described herein provides materials and methods for use in the delivery to and expression of a polynucleotide encoding a TNF antagonist in a mammal. The polynucleotide encoding a TNF antagonist is delivered to the mammal through a recombinant adeno-associated virus (rAAV) vector, a vector which integrates into the genome of the host cell. Introduction of rAAV DNA into cells generally leads to long-term persistence and expression of DNA without disturbing the normal metabolism of the cell. Thus, the invention provides a continuous source of and ongoing administration of the TNF antagonist to the mammal. This is a distinct and significant advantage over previously described treatment modalities (i.e., exogenous administration of therapeutic agents), which confer only transient benefits.

Definitions

As used in the specification and claims, the singular form "a", "an" and "the" include plural references unless the context clearly dictates otherwise. For example, the term "a cell" includes a plurality of cells, including mixtures thereof.

A "TNF antagonist" as used herein refers to a polypeptide that binds TNF and inhibits and/or hinders TNF activity as reflected in TNF binding to a TNF-receptor including any of the following: (a) TNFR, preferably endogenous (i.e., native to the individual or host), cell membrane bound TNFR; (b) the extracellular domain(s) of TNFR; and/or (c) the TNF binding domains of TNFR (which may be a portion of the extracellular domain). TNF antagonists include, but are not limited to, TNF receptors (or appropriate portions thereof, as described herein) and anti-TNF antibodies. As used herein, the "biological activity" of a TNF antagonist is to bind to TNF and inhibit and/or hinder TNF from binding to any of the following: (a) TNFR, preferably endogenous, cell membrane bound TNFR; (b) the extracellular domain(s) of TNFR; and (c) the TNF binding domains of TNFR (which may be a portion of the extracellular domain). A TNF antagonist can be shown to exhibit biological activity using assays known in the art to measure TNF activity and its inhibition, an example of which is provided herein.

"TNF-associated disorders" are those disorders or diseases that are associated with, result from, and/or occur in response to, elevated levels of TNF. Such disorders may be associated with episodic or chronic elevated levels of TNF activity and/or with local or systemic increases in TNF activity. Such disorders include, but are not limited to, inflammatory diseases, such as arthritis and inflammatory bowel disease, and congestive heart failure.

As used herein, the terms "TNF receptor polypeptide" and "TNFR polypeptide" refer to polypeptides derived from TNFR (from any species) which are capable of binding TNF. Two distinct cell-surface TNFRs have described: Type II TNFR (or p75 TNFR or TNFRII) and Type I TNFR (or p55 TNFR or TNFRI). The mature full-length human p75 TNFR is a glycoprotein having a molecular weight of about 75–80 kilodaltons (kD). The mature full-length human p55 TNFR is a glycoprotein having a molecular weight of about 55–60 kD. The preferred TNFR polypeptides of this invention are derived from TNFR Type I and/or TNFR type II.

TNFR polypeptides, such as "TNFR", "TNFR:Fc" and the like, when discussed in the context of the present invention and compositions therefor, refer to the respective intact polypeptide (such as, TNFR intact), or any fragment or derivative thereof (such as, an amino acid sequence derivative), that exhibits the desired biological activity (i.e., binding to TNF). A "TNFR polynucleotide" is any polynucleotide which encodes a TNFR polypeptide (such as a TNFR:Fc polypeptide).

As used herein, an "extracellular domain" of TNFR refers to a portion of TNFR that is found between the amino-terminus of TNFR and the amino-terminal end of the TNFR transmembrane region. The extracellular domain of TNFR binds TNF.

A "IL-1 antagonist" as used herein refers to a polypeptide that binds interleukin I (IL-1) and inhibits and/or hinders IL-1 activity as reflected in IL-1 binding to an IL-1 receptor including any of the following: (a) IL-1 receptor (IL-1R), preferably endogenous (i.e., native to the individual or host), cell membrane bound IL-1R (b) the extracellular domain(s) of IL-1R; and/or (c) the IL-1 binding domains of IL-1R (which may be a portion of the extracellular domain). IL-1 antagonists include, but are not limited to, IL-1 receptors (or appropriate portions thereof, as described herein) and anti-IL-1 antibodies. As used herein, the "biological activity" of an IL-1 antagonist is to bind to IL-1 and inhibit and/or hinder IL-1 from binding to any of the following: (a) IL-1R, preferably endogenous, cell membrane bound IL-1R; (b) the extracellular domain(s) of IL-1R; and/or (c) the IL-1 binding domains of IL-1R (which may be a portion of the extracellular domain). An IL-1 antagonist can be shown to exhibit biological activity using assays known in the art, including IL-1 inhibition assays, which are described herein as well as in the art.

As used herein, the term "IL-1 receptor polypeptide" refers to polypeptides derived from IL-1 receptor (from any species) which are capable of binding IL-1. IL-1R polypeptides, when discussed in the context of the present invention and compositions therefor, refer to the respective intact polypeptide (such as intact IL-1R), or any fragment or derivative thereof (such as, an amino acid sequence derivative), that exhibits the desired biological activity (i.e., binding to IL-1). A "IL-1R polynucleotide" is any polynucleotide which encodes a IL-1R polypeptide.

As used herein, an "extracellular domain" of IL-1R refers to a portion of IL-1R that is found between the amino-terminus of IL-1R and the amino-terminal end of the IL-1R transmembrane region. The extracellular domain of IL-1R binds IL-1.

The terms "polypeptide", "peptide" and "protein" are used interchangeably herein to refer to polymers of amino acids of any length. The terms also encompass an amino acid polymer that has been modified; for example, disulfide bond formation, glycosylation, lipidation, or conjugation with a labeling component.

A "chimeric polypeptide" or "fusion polypeptide" is a polypeptide comprising regions in a different position than occurs in nature. The regions may normally exist in separate proteins and are brought together in the chimeric or fusion polypeptide, or they may normally exist in the same protein but are placed in a new arrangement in the chimeric or fusion polypeptide. A chimeric or fusion polypeptide may also arise from polymeric forms, whether linear or branched, of TNFR polypeptide(s).

The terms "polynucleotide" and "nucleic acid", used interchangeably herein, refer to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "chimeric polynucleotide" or "fusion polynucleotide" is a polynucleotide comprising regions in a different position than occurs in nature. The regions may normally exist in separate genes and are brought together in the chimeric or fusion polynucleotide, or they may normally exist in the same gene but are placed in a new arrangement in the chimeric or fusion polynucleotide.

"AAV" is an abbreviation for adeno-associated virus, and may be used to refer to the virus itself or derivatives thereof. The term covers all subtypes and both naturally occurring and recombinant forms, except where required otherwise.

An "rAAV vector" as used herein refers to an AAV vector comprising a polynucleotide sequence not of AAV origin (i.e., a polynucleotide heterologous to AAV), typically a sequence of interest for the genetic transformation of a cell. The heterologous polynucleotide is flanked by at least one, preferably two, AAV inverted terminal repeat sequences (ITRs). As described herein, an rAAV vector can be in any of a number of forms, including, but not limited to, plasmids, linear artificial chromosomes, complexed with lipids, encapsulated within liposomes and, most preferably, encapsidated in a viral particle, particularly an AAV.

An "rAAV virus" or "rAAV viral particle" refers to a viral particle composed of at least one AAV capsid protein (preferably by all of the capsid proteins of a wild-type AAV) and an encapsidated rAAV.

"Packaging" refers to a series of intracellular events that result in the assembly and encapsidation of an AAV particle or rAAV particle.

AAV "rep" and "cap" genes refer to polynucleotide sequences encoding replication and encapsidation proteins of adeno-associated virus. They have been found in all AAV serotypes examined, and are described below and in the art. AAV rep and cap are referred to herein as AAV "packaging genes".

A "helper virus" for AAV refers to a virus that allows AAV to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

An "infectious" virus or viral particle is one that comprises a polynucleotide component which it is capable of delivering into a cell for which the viral species is trophic. The term does not necessarily imply any replication capacity of the virus. Assays for counting infectious viral particles are described in the art.

A "replication-competent" virus (e.g., a replication-competent AAV, sometimes abbreviated as "RCA") refers to a phenotypically wild-type virus that is infectious, and is also capable of being replicated in an infected cell (i.e., in the presence of a helper virus or helper virus functions). In the case of AAV, replication competence generally requires the presence of functional AAV packaging genes. Preferred rAAV vectors as described herein are replication-incompetent in mammalian cells (especially in human cells) by virtue of the lack of one or more AAV packaging genes. Preferably, such rAAV vectors lack any AAV packaging gene sequences in order to minimize the possibility that RCA are generated by recombination between AAV packaging genes and an rAAV vector.

A "gene" refers to a polynucleotide containing at least one open reading frame that is capable of encoding a particular protein after being transcribed and translated.

"Recombinant", as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Preferably, the genetic element is introduced into a chromosome or mini-chromosome in the cell; but any alteration that changes the phenotype and/or genotype of the cell and its progeny is included in this term.

A cell is said to be "stably" altered, transduced, or transformed with a genetic sequence if the sequence is available to perform its function during extended culture of the cell in vitro. In preferred examples, such a cell is "inheritably" altered in that a genetic alteration is introduced which is also inheritable by progeny of the altered cell.

"Stable integration" of a polynucleotide into a cell means that the polynucleotide has been integrated into a replicon that tends to be stably maintained in the cell. Although episomes such as plasmids can sometimes be maintained for many generations, genetic material carried episomally is generally more susceptible to loss than chromosomally-integrated material. However, maintenance of a polynucleotide can often be effected by incorporating a selectable marker into or adjacent to a polynucleotide, and then maintaining cells carrying the polynucleotide under selective pressure. In some cases, sequences cannot be effectively maintained stably unless they have become integrated into a chromosome; and, therefore, selection for retention of a sequence comprising a selectable marker can result in the selection of cells in which the marker has become stably-integrated into a chromosome. Antibiotic resistance genes can be conveniently employed as such selectable markers, as is well known in the art. Typically, stably-integrated polynucleotides would be expected to be maintained on average for at least about twenty generations, preferably at least about one hundred generations, still more preferably they would be maintained permanently. The chromatin structure of eukaryotic chromosomes can also influence the level of expression of an integrated polynucleotide. Having the genes carried on stably-maintained episomes can be particularly useful where it is desired to have multiple stably-maintained copies of a particular gene. The selection of stable cell lines having properties that are particularly desirable in the context of the present invention are described and illustrated below.

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred.

A preparation of rAAV is said to be "substantially free" of helper virus if the ratio of infectious rAAV particles to infectious helper virus particles is at least about $10^2$:1; preferably at least about $10^4$:1, more preferably at least about $10^6$:1; still more preferably at least about $10^8$:1. Preparations are also preferably free of equivalent amounts of helper virus proteins (i. e., proteins as would be present as a result of such a level of helper virus if the helper virus particle impurities noted above were present in disrupted form). Viral and/or cellular protein contamination can generally be observed as the presence of Coomassie staining bands on SDS gels (e.g. the appearance of bands other than those corresponding to the AAV capsid proteins VP1, VP2 and VP3).

A "host cell" includes an individual cell or cell culture which can be or has been a recipient for vector(s) or for incorporation of polynucleotides and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide (s) of this invention.

"Transformation" or "transfection" refers to the insertion of an exogenous polynucleotide into a host cell, irrespective of the method used for the insertion, for example, lipofection, transduction, infection or electroporation. The exogenous polynucleotide may be maintained as a non-integrated vector, for example, a plasmid, or alternatively, may be integrated into the host cell genome.

An "individual" or "subject" refers to vertebrates, particularly members of a mammalian species, and includes, but is not limited to, domestic animals, sports animals, rodents and primates, including humans.

An "effective amount" is an amount sufficient to effect beneficial or desired clinical results. An effective amount can be administered in one or more administrations. For purposes of this invention, an "effective amount" is an amount that achieves any of the following: reduction of TNF levels; reduction of an inflammatory response; and/or palliation, amelioration, stabilization, reversal, slowing or delay in the progression of the disease state.

As used herein, "in conjunction with" refers to administration of one treatment modality in addition to another treatment modality, such as adminstration of a TNF antagonist to a subject in addition to the delivery of an rAAV to the same subject, or administration of two different rAAV vectors to the same subject. As such, "in conjunction with" refers to administration of one treatment modality before, during or after delivery of the other treatment modality to the subject.

An "arthritic condition" is a term well-understood in the art refers to a state characterized by inflammation of a joint or joints.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. For example, treatment of an individual may be undertaken to decrease or limit the pathology associated with elevated levels of TNF, including, but not limited to, an inherited or induced genetic deficiency, infection by a viral, bacterial, or parasitic organism, a neoplastic or aplastic condition, or an immune system dysfunction such as autoimmunity. Treatment may be performed either prophylactically or therapeutically; that is, either prior or subsequent to the initiation of a pathologic event or contact with an etiologic agent.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

"Palliating" a disease means that the extent and/or undesirable clinical manifestations of a disease state are lessened and/or time course of the progression is slowed or lengthened, as compared to not administering rAAV vectors of the present invention.

General Techniques

The practice of the present invention will employ, unless otherwise indicated, conventional techniques of molecular biology, virology, animal cell culture and biochemistry which are within the skill of the art. Such techniques are explained fully in the literature. See, for example, "Molecular Cloning: A Laboratory Manual", Second Edition (Sambrook, Fritsch & Maniatis, 1989); "Animal Cell Culture" (R. I. Freshney, ed., 1987); "Gene Transfer Vectors for Mammalian Cells" (J. M. Miller & M. P. Calos, eds., 1987); "Current Protocols in Molecular Biology" (F. M. Ausubel et al., eds., 1987); "Current Protocols in Protein Science" (John E Coligan, et al. eds. Wiley and Sons, 1995); and "Protein Purification: Principles and Practice" (Robert K. Scopes, Springer-Verlag, 1994).

rAAV Vectors for Delivery of TNF Antagonist

This invention provides recombinant AAV (rAAV) vectors for reducing levels of TNF in a subject. This reduction may occur anywhere in the body, such as in a tissue(s), a particular anatomical site and/or circulation. Generally, these rAAV vectors comprise a polynucleotide encoding a TNF antagonist. Preferably the TNF antagonist is a TNFR, or a TNFR polypeptide (including biologically active derivative(s) thereof). In the present invention, a preferred TNFR is derived from the p75 TNFR.

An rAAV vector of this invention comprises a heterologous (i.e. non-AAV) polynucleotide of interest in place of the AAV rep and/or cap genes that normally make up the bulk of the AAV genome. As in the wild-type AAV genome, however, the heterologous polynucleotide is preferably flanked by at least one, more preferably two, AAV inverted terminal repeats (ITRs). Variations in which an rAAV construct is flanked by a only a single (typically modified) ITR have been described in the art and can be employed in connection with the present invention.

TNF Antagonists

In the present invention, a TNF antagonist is supplied to an individual, preferably a mammal, most preferably a human, as an expressed product of a polynucleotide which encodes a TNF antagonist. The polynucleotide encoding the TNF antagonist is delivered to the mammal in the form of an rAAV vector. As defined, such a TNF antagonist may be any polypeptide which binds to TNF including, but not limited to, a TNFR polypeptide and an anti-TNF antibody.

The TNF antagonist is secreted by the cell that receives the rAAV vector; preferably the TNF antagonist is soluble (i.e., not attached to the cell). For example, soluble TNF antagonists are devoid of a transmembrane region and are secreted from the cell. Techniques to identify and remove polynucleotide sequences which encode transmembrane domains are known in the art.

Preferably, the TNF antagonist is a TNFR polypeptide. TNFR polypeptide may be an intact TNFR (preferably from the same species that receives the rAAV) or a suitable fragment of TNFR. U.S. Pat. No. 5,605,690 provides examples of TNFR polypeptides, including soluble TNFR polypeptides, appropriate for use in the present invention. Preferably, the TNFR polypeptide comprises an extracelluar domain of TNFR. More preferably, the TNFR polypeptide is a fusion polypeptide comprising an extracellular domain of TNFR linked to a constant domain of an immunoglobulin molecule; still more preferably, the TNFR polypeptide is a fusion polypeptide comprising an extracellular domain of the p75 TNFR linked to a constant domain of an IgG1 molecule. Preferably when administration to humans is contemplated, an Ig used for fusion proteins is human, preferably human IgG1.

Monovalent and multivalent forms of TNFR polypeptides may be used in the present invention. Multivalent forms of TNFR polypeptides possess more than one TNF binding site. Multivalent forms of TNFR polypeptides may be encoded in an rAAV vector, for example, through the repeated ligation of polynucleotides encoding TNF binding domains, each repeat being separated by a linker region. Preferably, the TNFR of the present invention is a bivalent, or dimeric, form of TNFR. For example, as described in U.S.

Pat. No. 5,605,690 and in Mohler et al., 1993, *J. Immunol.,* 151:1548–1561, a chimeric antibody polypeptide with TNFR extracellular domains substituted for the variable domains of either or both of the immunoglobulin heavy or light chains would provide a TNFR polypeptide for the present invention. Generally, when such a chimeric TNFR:antibody polypeptide is produced by cells, it forms a bivalent molecule through disulfide linkages between the immunoglobulin domains. Such a chimeric TNFR:antibody polypeptide is referred to as TNFR:Fc.

The TNFR polypeptide construct sTNFR(p75):Fc is a preferred embodiment of a TNF antagonist of the present invention. The polypeptide sequence of sTNFR(p75):Fc is depicted in FIG. 1. The coding sequence for this TNF antagonist is found in plasmid pCAVDHFRhuTNFRFc as described in U.S. Pat. No. 5,605,690. Any polynucleotide which encodes this sTNFR(p75):Fc polypeptide is suitable for use in the present invention. A polynucleotide sequence encoding sTNFR(p75):Fc is depicted in FIGS. 2A and 2B.

In the present invention, additional TNFR polypeptide sequences include, but are not limited to, those indicated in FIGS. 2 and 3 of U.S. Pat. No. 5,395,760.

Polynucleotides which encode TNFR polypeptides can be generated using methods known in the art from TNFR polynucleotide sequences known in the art. In the present invention, preferable polynucleotide sequences which encode TNFR polypeptides include, but are not limited to, TNFR polynucleotide sequences found in U.S. Pat. Nos. 5,395,760 and 5,605,690 and GenBank entries M32315 (human TNFR) and M59378 (murine TNFRI). Suitable polynucleotides for use in the present invention can be synthesized using standard synthesis and recombinant methods.

Methods to assess TNF antagonist activity are known in the art and exemplified herein. For example, TNF antagonist activity may be assessed with a cell-based competitive binding assay. In such an assay, radiolabelled TNF is mixed with serially diluted TNF antagonist and cells expressing cell membrane bound TNFR. Portions of the suspension are centrifuged to separate free and bound TNF and the amount of radioactivity in the free and bound fractions determined. TNF antagonist activity is assessed by inhibition of TNF binding to the cells in the presence of the TNF antagonist.

As another example, TNF antagonists may be analyzed for the ability to neutralize TNF activity in vitro in a bioassay using cells susceptible to the cytotoxic activity of TNF as target cells, such as L929 cells (see, for example, Example 3). In such an assay, target cells, cultured with TNF, are treated with varying amounts of TNF antagonist and subsequently are examined for cytolysis. TNF antagonist activity is assessed by a decrease in TNF-induced target cell cytolysis in the presence of the TNF antagonist.

The invention also provides rAAV vectors comprising a polynucleotide encoding an interleukin 1 (IL-1) antagonist. The cytokine IL-1 has been implicated as a pivotal mediator in both the early and late disease stages of RA (Joosten et al., 1996, *Arthritis Rheum.* 39:797–809). In RA, IL-1 appears to be involved in infiltration of inflammatory cells and cartilage destruction in the affected joint. A clinical trial with an IL-1 antagonist in patients with RA indicated that blocking IL-1 activity may result in amelioration of RA symptoms (Campion et al., 1996, *Arthritis Rheum.* 39:1092–1101; Bresnihan et al., 1996, *Arthritis Rheum.* 39:S73). In a murine arthritis model, a combined anti-TNFα/anti-IL-1 treatment led to both diminished inflammation and to diminished joint cartilage damage (Kuiper et al., 1998, *Cytokine* 10:690–702).

As IL-1 and TNF appear to mediate different aspects of RA, the present invention provides rAAV vectors comprising a polynucleotide encoding a TNF antagonist (such as sTNFR(p75):Fc) and an IL-1 antagonist (or, the rAAV vector comprises a polynucleotide which encodes a TNF antagonist and an IL-1 antagonist). The present invention also provides rAAV vectors comprising a polynucleotide encoding an IL-1 antagonist. Preferably, the IL-1 antagonist is an IL-1 receptor (IL-1R), or an IL-1R polypeptide (including biologically active derivatives(s) thereof), that exhibits the desired biological activity (i.e., binding to IL-1). Preferably, the IL-1R is derived from IL-1R type II. In the present invention, preferable IL-1R polypeptide sequences include, but are not limited to, that depicted in FIG. 3 and those found in IL-1R GenBank entry U74649 and U.S. Pat. No. 5,350,683. Any polynucleotide which encodes an IL-1R polypeptide is suitable for use in the present invention. A polynucleotide sequence encoding a preferred IL-1R polypeptide is depicted in FIG. 3. Suitable polynucleotides for use in the present invention can be synthesized using standard synthesis and recombinant methods.

Methods to assess IL-1 antagonist activity are known in the art. For example, IL-1 antagonist activity may be assessed with a cell-based competitive binding assay as described herein for TNF antagonists. As another example, IL-1 antagonist activity may be assessed for the ability to neutralize IL-1 activity in vitro in a bioassay for IL-1. In such an assay, a cell line (for example, EL-4 NOB-1) is used that produces interleukin 2 (IL-2) in response to treatment with IL-1. This IL-1 responsive cell line is used in combination with a IL-2 sensitive cell line (for example, CTLL-2). Proliferation of the IL-2 sensitive cell line is dependent on the IL-1 responsive cell line producing IL-2 and thus, is used as a measure of Il-1 stimulation of the IL-1 responsive cell line. IL-1 antagonist activity would be assessed by its ability to neutralize IL-1 activity in such a IL-1 bioassay (Gearing et al., 1991, *J. Immunol. Methods* 99:7–11; Kuiper et al., 1998).

In preferred embodiments, the vector(s) of the invention are encapsidated into an rAAV virus particle. Accordingly, the invention includes an rAAV virus particle (recombinant because it contains a recombinant polynucleotide) comprising any of the vectors described herein. Methods of producing such particles are described below.

The present invention also provides compositions containing any of the rAAV vectors (and/or rAAV virus particles comprising the rAAV vectors) described herein. These compositions are especially useful for administration to individuals who may benefit from a reduction in the level of TNF.

Generally, the compositions of the invention for use in reducing TNF levels comprise an effective amount of an rAAV vector encoding a TNF antagonist, preferably in a pharmaceutically acceptable excipient. As is well known in the art, pharmaceutically acceptable excipients are relatively inert substances that facilitate administration of a pharmacologically effective substance and can be supplied as liquid solutions or suspensions, as emulsions, or as solid forms suitable for dissolution or suspension in liquid prior to use. For example, an excipient can give form or consistency, or act as a diluent. Suitable excipients include but are not limited to stabilizing agents, wetting and emulsifying agents, salts for varying osmolarity, encapsulating agents, and buffers. Excipients as well as formulations for parenteral and nonparenteral drug delivery are set forth in *Remington's Pharmaceutical Sciences* 19th Ed. Mack Publishing (1995).

Generally, these rAAV compositions are formulated for administration by injection (e.g., intra-articularly, intravenously, intramuscularly, etc.). Accordingly, these compositions are preferably combined with pharmaceutically acceptable vehicles such as saline, Ringer's balanced salt solution (pH 7.4), dextrose solution, and the like. Although not required, pharmaceutical compositions may optionally be supplied in unit dosage form suitable for administration of a precise amount.

The invention also includes any of the above vectors (or compositions comprising the vectors) for use in treatment of TNF-associated disorders, such as inflammatory conditions (including arthritis). The invention also includes any of the above vectors (or compositions comprising the vectors) for use in reducing TNF levels in an individual. The invention further provides use of any of the above vectors (or compositions comprising the vectors) in the manufacture of a medicament for treatment of TNF-associated disorders, such as inflammatory condiitons (including arthritis). The invention also provides use of any of the above vectors (or compositions comprising the vectors) in the manufacture of a medicament for reducing TNF activity levels in an individual.

Host Cells Comprising an rAAV of the Invention

The present invention also provides host cells comprising rAAV vectors described herein. Among eukaryotic host cells are yeast, insect, avian, plant and mammalian cells. Preferably, the host cells are mammalian. For example, host cells include, but are not limited to, HeLa and 293 cells, both of human origin and both readily avaliable.

The development of host cells able to express the rAAV vector sequence provides an established source of the material that is expressed at a reliable level. Methods and compositions for introducing the rAAV vector into the host cell and then for determining whether a host cell contains the rAAV vector are discussed in a later section, have been described art and are widely available.

Included in these embodiments, and discussed in a later section are so called "producer cells" used as a basis for producing packaged rAAV vectors.

Preparation of the rAAV of the Invention

The rAAV vectors of this invention may be prepared using standard methods in the art. Adeno-associated viruses of any serotype are suitable, since the various serotypes are functionally and structurally related, even at the genetic level (see, e.g., Blacklow, pp. 165–174 of "Parvoviruses and Human Disease" J. R. Pattison, ed. (1988); and Rose, Comprehensive Virology 3:1, 1974). All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed. For a general review of AAV biology and genetics, see, e.g., Carter, "Handbook of Parvoviruses", Vol. I, pp. 169–228 (1989), and Berns, "Virology", pp. 1743–1764, Raven Press, (1990). General principles of rAAV vector construction are known in the art. See, e.g., Carter, 1992, *Current Opinion in Biotechnology,* 3:533–539; and Muzyczka, 1992, *Curr. Top. Microbiol. Immunol.,* 158:97–129.

As described above, the rAAV vectors of this invention comprise a heterologous polynucleotide that encodes a TNF antagonist. The rAAV vectors may also encode additional polypeptides, such as an IL-1 receptor type II. Alternatively, the rAAV vectors may comprise a heterologous polynucleotide that encodes an IL-1 antagonist, such as an IL-1R. Such a heterologous polynucleotide will generally be of sufficient length to provide the encoding sequence and desired function. For encapisdation within AAV2 particles, the heterologous polynucleotide will preferably be less than about 5 kb although other serotypes and/or modifications may be employed to allow larger sequences to packaged into the AAV viral particles. For example, a preferred polynucleotide encodes a TNFR:Fc as represented in SEQ ID NO: 1, is about 1.5 kb in length.

Since transcription of the heterologous polynucleotide is desired in the intended target cell, it can be operably linked to its own or to a heterologous promoter and/or enhancer, depending for example on the desired level and/or specificity of transcription within the target cell, as is known in the art. Various types of promoters and enhancers are suitable for use in this context. For example, Feldhaus (U.S. patent application Ser. No. 09/171,759, filed Oct. 20, 1998) describes a modified ITR comprising a promoter to regulate expression from an rAAV. Constitutive promoters provide an ongoing level of gene transcription, and are preferred when it is desired that the therapeutic polynucleotide be expressed on an ongoing basis. Inducible or regulatable promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific, that is, they exhibit their activity only in certain cell types, presumably due to gene regulatory elements found uniquely in those cells. Such tissue-specific promoters and enhancers are known in the art. By way of illustration, an example of tissue-specific promoters includes various myosin promoters for expression in muscle. Another example of tissue-specific promoters and enhancers are of regulatory elements for cell and/or tissue types that are in a joint.

Preferred inducible or regulated promoters and/or enhancers include those that are physiologically responsive, such as those that are responsive to inflammatory signals and/or conditions. For example, use of promoters and/or enhancers that are activated in response to mediators that drive inflammatory flares, including, but not limited to, those from proinflammatory cytokine genes (e.g., TRF$\alpha$, IL-1$\beta$ and IFN$\gamma$). would result in the expression of a TNF antagonist during the period of inflammatory flare (Varley et al., 1998, *Mol. Med. Today* 4:445–451). The TNF$\alpha$ promoter region is approximately 1.2 kb, and the sequence has been reported by Takashiba et al., 1993, *Gene,* 131:307–308.

Further illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Additional inducible promoters include heavy metal ion inducible promoters (such as the mouse mammary tumor virus (mMTV) promoter or various growth hormone promoters), and the promoters from T7 phage which are active in the presence of T7 RNA polymerase. A large variety of other promoters are known and generally available in the art, and the sequences for many such promoters are available in sequence databases such as the GenBank database.

As translation is also desired in the intended target cell, the heterologous polynucleotide encoding a TNF antagonist will preferably also comprise control elements that facilitate translation (such as a ribosome binding site or "RBS" and a polyadenylation signal). Accordingly, the heterologous polynucleotide will generally comprise at least one coding region operatively linked to a suitable promoter, and can also comprise, for example, an operatively linked enhancer, ribosome binding site and poly-A signal. The heterologous polynucleotide can comprise one encoding region, or more than one encoding region under the control of the same or different promoters. The entire unit, containing a combination of control elements and encoding region, is often referred to as an expression cassette.

A heterologous polynucleotide encoding a TNF antagonist is integrated by recombinant techniques into or preferably in place of the AAV genomic coding region (i.e., in place of the AAV rep and cap genes), but is generally flanked on either side by AAV ITRs. This means that an ITR appears both upstream and downstream from the coding sequence, either in direct juxtaposition, preferably (although not necessarily) without any intervening sequence of AAV origin in order to reduce the likelihood of recombination that might regenerate a replication-competent AAV ("RCA") genome. Recent evidence suggests that a single ITR can be sufficient to carry out the functions normally associated with configurations comprising two ITRs (U.S. Pat. No. 5,478745), and vector constructs with only one ITR can thus be employed in conjunction with the packaging and production methods described herein. The resultant rAAV vector is referred to as being "defective" in AAV functions when specific AAV coding sequences are deleted from the vector.

Given the relative encapsidation size limits of various AAV genomes, insertion of a large heterologous polynucleotide into the genome necessitates removal of a portion of the AAV genome, in particular, one or more of the packaging genes may be removed. Removal of one or more AAV genes is in any case desirable, to reduce the likelihood of generating RCA. Accordingly, encoding or promoter sequences for rep, cap, or both, are preferably removed, since the functions provided by these genes can be provided in trans.

The rAAV vectors are provided in a variety of forms, such as in the form of bacterial plasmids, AAV particles, liposomes or any combination thereof. In other embodiments, the rAAV vector sequence is provided in the eukaryotic cells transfected with the rAAV vector.

If the rAAV is to be used in the form of a packaged rAAV particle, there are at least three desirable features of an rAAV virus preparation for use in gene transfer. First, it is preferred that the rAAV virus should be generated at titers sufficiently high to transduce an effective proportion of cells in the target tissue. High number of rAAV viral particles are typically required for gene transfer in vivo. For example, some treatments may require in excess of $10^8$ particles. Second, it is preferred that the rAAV virus preparations should be essentially free of replication-competent AAV (i.e., phenotypically wild-type AAV which can be replicated in the presence of helper virus or helper virus functions). Third, it is preferred that the rAAV virus preparation as a whole be essentially free of other viruses (such as a helper virus used in AAV production) as well as helper virus and cellular proteins, and other components such as lipids and carbohydrates, so as to minimize or eliminate any risk of generating an immune response in the context of gene transfer. This latter point is especially significant in the context of AAV because AAV is a "helper-dependent" virus that requires co-infection with a helper virus (typically adenovirus) or other provision of helper virus functions in order to be effectively replicated and packaged during the process of AAV production; and, moreover, as described above, adenovirus has been observed to generate a host immune response in the context of gene transfer applications (see, e.g., Le et al., 1997; Byrnes et al., 1995, *Neuroscience,* 66:1015; McCoy et al., 1995, *Human Gene Therapy,* 6:1553; and Barr et al., 1995, *Gene Therapy,* 2:15 1).

If an rAAV vector is to be packaged in an AAV particle, in order to replicate and package the rAAV vector, the missing functions are complemented with a packaging gene, or a plurality thereof, which together encode the necessary functions for the various missing rep and/or cap gene products. The packaging genes or gene cassettes are preferably not flanked by AAV ITRs and preferably do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of the homologous sequences and with their level of shared identity. The level of homology that will pose a concern in a given system can be determined theoretically and confirmed experimentally, as is known in the art. Generally, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al. in U.S. patent application Ser. No. 08/769,728, filed Dec. 18, 1996 (now provisional application No. 60/041,609).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., U.S. Pat. No. 5,837,484; Burstein et al., WO 98/27207; and Johnson et al., U.S. Pat. No. 5,658,785). The AAV cap gene, providing the encapsidation proteins as described above, can be provided together with an AAV rep gene or separately (see, e.g., the above-referenced applications and patents as well as Allen et al. (WO 96/17947). Other combinations are possible.

As is described in the art, and illustrated in the references cited above and in Examples below, genetic material can be introduced into cells (such as mammalian "producer" cells for the production of rAAV) using any of a variety of means to transform or transduce such cells. By way of illustration, such techniques include, but are not limited to, transfection with bacterial plasmids, infection with viral vectors, electroporation, calcium phosphate precipitation, and introduction using any of a variety of lipid-based compositions (a process often referred to as "lipofection"). Methods and compositions for performing these techniques have been described in the art and are widely available.

Selection of suitably altered cells may be conducted by any technique in the art. For example, the polynucleotide sequences used to alter the cell may be introduced simultaneously with or operably linked to one or more detectable or selectable markers as is known in the art. By way of illustration, one can employ a drug resistance gene as a selectable marker. Drug resistant cells can then be picked and grown, and then tested for expression of the desired sequence (i.e., a product of the heterologous polynucleotide). Testing for acquisition, localization and/or maintenance of an introduced polynucleotide can be performed using DNA hybridization-based techniques (such as Southern blotting and other procedures as known in the art). Testing for expression can be readily performed by Northern analysis of RNA extracted from the genetically altered cells, or by indirect immunofluorescence for the corresponding gene product. Testing and confirmation of packaging capabilities and efficiencies can be obtained by introducing to the cell the remaining functional components of AAV and a helper virus, to test for production of AAV particles. Where a cell is inheritably altered with a plurality of polynucleotide constructs, it is generally more convenient (though not essential) to introduce them to the cell separately, and validate each step seriatim. References describing such techniques include those cited herein.

In one approach to packaging rAAV vectors in an AAV particle, the rAAV vector sequence (i.e., the sequence flanked by AAV ITRs), and the AAV packaging genes to be provided in trans, are introduced into the host cell in separate bacterial plasmids. Examples of this approach are described in Ratschin et al., 1984, *Mol. Cell. Biol.,* 4:2072; Hermonat et al., 1984, *Proc. Natl. Acad. Sci. USA,* 81:6466; Tratschin et al., 1985, *Mol. Cell. Biol.,* 5:3251; McLaughlin et al., 1988, *J. Virol.,* 62:1963; Lebkowski et al., 1988, *Mol. Cell. Biol.,* 7:349; Samulski et al., 1989, *J. Virol.,* 63:3822–3828; and Flotte et al., 1992, *Am. J. Respir. Cell. Mol. Biol.,* 7:349.

A second approach is to provide either the rAAV vector sequence, or the AAV packaging genes, in the form of an episomal plasmid in a mammalian cell used for AAV replication. See, for example, U.S. Pat. No. 5,173,414.

A third approach is to provide either the rAAV vector sequence or the AAV packaging genes, or both, stably integrated into the genome of the mammalian cell used for replication, as exemplified in Example 2 below.

One exemplary technique of this third approach is outlined in international patent application WO 95/13365 (Targeted Genetics Corporation and Johns Hopkins University) and corresponding U.S. Pat. No. 5,658,776 (by Flotte et al.). This example uses a mammalian cell with at least one intact copy of a stably integrated rAAV vector, wherein the vector comprises an AAV ITR and a transcription promoter operably linked to a target polynucleotide, but wherein the expression of rep is limiting in the cell. In a preferred embodiment, an AAV packaging plasmid comprising the rep gene operably linked to a heterologous promoter is introduced into the cell, and then the cell is incubated under conditions that allow replication and packaging of the rAAV vector sequence into particles.

Another approach is outlined in Trempe et al., U.S. Pat. No. 5,837,484. This example uses a stable mammalian cell line with an AAV rep gene operably linked to a heterologous promoter so as to be capable of expressing functional kep protein. In various preferred embodiments, the AAV cap gene can be provided stably as well or can be introduced transiently (e.g. on a plasmid). An rAAV vector can also be introduced stably or transiently.

Another approach is outlined in patent application WO 96/17947 (Targeted Genetics Corporation). This example uses a mammalian cell which comprises a stably integrated AAV cap gene, and a stably integrated AAV rep gene operably linked to a helper virus-inducible heterologous promoter. A plasmid comprising the rAAV vector sequence is also introduced into the cells (either stably or transiently). The packaging of rAAV vector into particles is then initiated by introduction of the helper virus.

Methods for achieving high titers of rAAV virus preparations that are substantially free of contaminating virus and/or viral or cellular proteins are outlined by Atkinson et al. in WO 99/11764. Techniques described therein can be employed for the large-scale production of rAAV viral particle preparations. Other methods for preparing rAAV described in WO 00/14205, WO 99/20773, and WO 99/20779.

These various examples address the issue of producing rAAV viral particles at sufficiently high titer, minimizing recombination between rAAV vector and sequences encoding packaging components, reducing or avoiding the potential difficulties associated with the expression of the AAV rep gene in mammalian cell line (since the Rep proteins can not only limit their own expression but can also affect cellular metabolism) and producing rAAV virus preparations that are substantially free of contaminating virus and/or viral or cellular protein.

Packaging of an AAV vector into viral particles relies on the presence of a suitable helper virus for AAV or the provision of helper virus functions. Helper viruses capable of supporting AAV replication are exemplified by adenovirus, but include other viruses such as herpes viruses (including, but not limited to, HSV1, cytomegalovirus and HHV-6) and pox virus (particularly vaccinia). Any such virus may be used.

Frequently, the helper virus will be an adenovirus of a type and subgroup that can infect the intended host cell. Human adenovirus of subgroup C, particularly serotypes 1, 2, 4, 6, and 7, are commonly used. Serotype 5 is generally preferred.

The features and growth patterns of adenovirus are known in the art. See, for example, Horowitz, "Adenoviridae and their replication", pp 771–816 in "Fundamental Virology", Fields et al., eds. The packaged adenovirus genome is a linear DNA molecule, linked through adenovirus ITRs at the left- and right-hand termini through a terminal protein complex to form a circle. Control and encoding regions for early, intermediate, and late components overlap within the genome. Early region genes are implicated in replication of the adenovirus genome, and are grouped depending on their location into the E1, E2, E3, and E4 regions.

Although not essential, in principle it is desirable that the helper virus strain be defective for replication in the subject ultimately to receive the genetic therapy. Thus, any residual helper virus present in an rAAV virus preparation will be replication-incompetent. Adenoviruses from which the E1A or both the E1A and the E3 region have been removed are not infectious for most human cells. They can be replicated in a permissive cell line (e.g., the human 293 cell line) which is capable of complementing the missing activity. Regions of adenovirus that appear to be associated with helper function, as well as regions that do not, have been identified and described in the art (see, e.g., P. Colosi et al., WO97/17458, and references cited therein).

For example, as described in Atkinson et al. (WO 99/11764), a "conditionally-sensitive" helper virus can also be employed to provide helper virus activity. Such a helper virus strain must minimally have the property of being able to support AAV replication in a host cell under at least one set of conditions where it itself does not undergo efficient genomic replication. Where helper virus activity is supplied as intact virus particles, it is also generally necessary that the virus be capable of replication in a host cell under a second set of conditions. The first set of conditions will differ from the second set of conditions by a readily controllable feature, such as the presence or absence of a required cofactor (such as a cation), the presence or absence of an inhibitory drug, or a shift in an environmental condition such as temperature. Most conveniently, the difference between the two conditions is temperature, and such a conditionally-sensitive virus is thus referred to as a temperature-sensitive helper virus.

Helper virus may be prepared in any cell that is permissive for viral replication. For adenovirus, preferred cells include 293 cells and HeLa cells. It is preferable to employ culture techniques that permit an increase in seeding density. 293 cells and HeLa cell variants are available that have been adapted to suspension culture. HeLa is preferable for reasons of cell growth, viability and morphology in suspension. These cells can be grown at sufficient density ($2\times10^6$ per ml) to make up for the lower replication rate of the temperature-sensitive adenovirus strain. Once established, cells are infected with the virus and cultured at the permissive temperature for a sufficient period; generally 3–7 days and typically about 5 days.

Examples of methods useful for helper virus preparation, isolation and concentration can be found in Atkinson et al. (WO 99/11764).

Several criteria influence selection of cells for use in producing rAAV particles as described herein. As an initial matter, the cell must be permissive for replication and packaging of the rAAV vector when using the selected helper virus. However, since most mammalian cells can be productively infected by AAV, and many can also be infected by helper viruses such as adenovirus, it is clear that a large variety of mammalian cells and cell lines effectively satisfy these criteria. Among these, the more preferred cells and cell lines are those that can be easily grown in culture so as to facilitate large-scale production of rAAV virus preparations. Again, however, many such cells effectively satisfy this criterion. Where large-scale production is desired, the choice of production method will also influence the selection of the host cell. For example, as described in more detail in Atkinson et al. (WO 99/11764) and in the art, some production techniques and culture vessels or chambers are designed for growth of adherent or attached cells, whereas others are designed for growth of cells in suspension. In the latter case, the host cell would thus preferably be adapted or adaptable to growth in suspension. However, even in the case of cells and cell lines that are regarded as adherent or anchorage-dependent, it is possible to derive suspension-adapted variants of an anchorage-dependent parental line by serially selecting for cells capable of growth in suspension. See, for example, Atkinson et al. (WO 99/11764).

Ultimately, the helper virus, the rAAV vector sequence, and all AAV sequences needed for replication and packaging must be present in the same cell. Where one or more AAV packaging genes are provided separately from the vector, a host cell is provided that comprises: (i) one or more AAV packaging genes, wherein each said AAV packaging gene encodes an AAV replication or encapsidation protein; (ii) a heterologous polynucleotide introduced into said host cell using an rAAV vector, wherein said rAAV vector comprises said heterologous polynucleotide flanked by at least one AAV ITR and is deficient in said AAV packaging gene(s); and (iii) a helper virus or sequences encoding the requisite helper virus functions. It should be noted, however, that one or more of these elements may be combined on a single replicon.

The helper virus is preferably introduced into the cell culture at a level sufficient to infect most of the cells in culture, but can otherwise be kept to a minimum in order to limit the amount of helper virus present in the resulting preparation. A multiplicity of infection or "MOI" of 1–100 may be used, but an MOI of 5–10 is typically adequate.

Similarly, if the rAAV vector and/or packaging genes are transiently introduced into the packaging cell (as opposed to being stably introduced), they are preferably introduced at a level sufficient to genetically alter most of the cells in culture. Amounts generally required are of the order of 10 $\mu$g per $10^6$ cells, if supplied as a bacterial plasmid; or $10^8$ particles per $10^5$ cells, if supplied as an AAV particle. Determination of an optimal amount is an exercise of routine titration that is within the ordinary skill of the artisan.

These elements can be introduced into the cell, either simultaneously, or sequentially in any order. Where the cell is inheritably altered by any of the elements, the cell can be selected and allowed to proliferate before introducing the next element.

In one preferred example, the helper virus is introduced last into the cell to rescue and package a resident rAAV vector. The cell will generally already be supplemented to the extent necessary with AAV packaging genes. Preferably, either the rAAV vector or the packaging genes, and more preferably both are stably integrated into the cell. It is readily appreciated that other combinations are possible. Such combinations are included within the scope of the invention.

Once the host cell is provided with the requisite elements, the cell is cultured under conditions that are permissive for the replication AAV, to allow replication and packaging of the rAAV vector. Culture time is preferably adjusted to correspond to peak production levels, and is typically 3–6 days. rAAV particles are then collected, and isolated from the cells used to prepare them.

Optionally, rAAV virus preparations can be further processed to enrich for rAAV particles, deplete helper virus particles, or otherwise render them suitable for administration to a subject. See Atkinson et al. for exemplary techniques (WO 99/11764). Purification techniques can include isopynic gradient centrifugation, and chromatographic techniques. Reduction of infectious helper virus activity can include inactivation by heat treatment or by pH treatment as is known in the art. Other processes can include concentration, filtration, diafiltration, or mixing with a suitable buffer or pharmaceutical excipient. Preparations can be divided into unit dose and multi dose aliquots for distribution, which will retain the essential characteristics of the batch, such as the homogeneity of antigenic and genetic content, and the relative proportion of contaminating helper virus.

Various methods for the determination of the infectious titer of a viral preparation are known in the art. For example, one method for titer determination is a high-throughput titering assay as provided by Atkinson et al. (WO 99/11764). Virus titers determined by this rapid and quantitative method closely correspond to the titers determined by more classical techniques. In addition, however, this high-throughput method allows for the concurrent processing and analysis of many viral replication reactions and thus has many others uses, including for example the screening of cell lines permissive or non-permissive for viral replication and infectivity.

Methods of Using rAAV of the Invention

The invention also provides methods in which administration of rAAV vectors described herein is used to reduce levels of TNF in a subject. Such methods may be particularly beneficial to individuals with a TNF-associated disorder. Disorders suitable for these methods are those associated with elevated levels of TNF and include, but are not limited to, arthritis (including RA), psoriatic arthritis, inflammatory bowel diseases (including Crohn's disease and ulcerative colitis), asthma and congestive heart failure.

The level of TNF may be circulating levels of TNF and/or levels of TNF in a tissue and/or at a particular anatomical site. It is understood that TNF levels are reduced when compared to TNF levels of a subject prior to receiving rAAV encoding a TNF antagonist or when compared to TNF levels of an individual that does not receive rAAV encoding a TNF antagonist. It is understood that TNF levels refers to levels of free (uncomplexed or unbound) or active TNF. Methods to detect TNF levels are described below.

In one embodiment, methods provided herein for reducing levels of TNF include administration (delivery) of rAAV vectors (or compositions comprising the vectors) described herein. In another embodiment, rAAV vectors are administered in conjunction with administration of a TNF antagonist, such as TNFR or anti-TNF antibody. The TNF antagonist, preferably in composition with physiologically acceptable carriers, exicipients or diluents, may be administered by suitable techniques including, but not limited to, intra-articular, intraperitoneal or subcutaneous routes by bolus injection, continuous infusion or sustained release from implants. As discussed below, the TNF antagonist may also be administered directly to the connective tissue, particularly the joint.

The invention also provides methods in which administration of rAAV vectors described herein (or compositions comprising an rAAV vector(s)) is used to reduce an inflammatory response in a subject. Preferably, an inflammatory response is reduced in a connective tissue, including, but not limited to, synovium, cartilage, ligament and tendon. A preferred anatomical site for reduction of an inflammatory response is an affected joint in a subject with arthritis, such as RA. It is understood that an inflammatory response is reduced when compared to an inflammatory response in a subject prior to receiving rAAV encoding a TNF antagonist or when compared to an inflammatory response in an individual that does not receive rAAV encoding TNF antagonist.

The invention also provides methods in which administration of rAAV vectors described herein (or compositions comprising an rAAV vector(s)) is used to palliate a TNF-associated disorder, including inflammatory diseases such as arthritis (i.e., an arthritic condition) occuring in a subject. Preferably, an arthritic condition is palliated in a joint, preferably connective tissue which includes, but is not limited to, synovium, cartilage, ligament and tendon. It is understood that an arthritic condition is palliated when compared to an arthritic condition in a subject prior to receiving rAAV encoding a TNF antagonist or when compared to an arthritic condition in an individual that does not receive rAAV encoding TNF antagonist.

In a preferred embodiment, the rAAV vector (or compositions comprising an rAAV vector(s)) is delivered to an arthritic joint of a mammal thus providing a source of the TNF antagonist at the site of inflammation. Even more preferably, the rAAV vector comprises a polynucleotide encoding sTNFR(p75):Fc.

In another preferred embodiment, the rAAV vector(s) (or compositions comprising an rAAV vector(s)) is delivered to an arthritic joint of a mammal providing a source of the TNF antagonist and a source of IL-1 antagonist at the site of inflammation. Preferably, the rAAV vector comprises a polynucleotide encoding sTNFR(p75):Fc and a polynucleotide encoding IL-1R.

In another preferred embodiment, a source of the TNF antagonist and a source of IL-1 antagonist are delivered to an arthritic joint of a mammal at the site of inflammation through the administration of at least two different rAAV vectors (or compositions comprising at least two different rAAV vectors). Preferably, one of the rAAV vectors comprises a polynucleotide encoding a TNFR and another one of the rAAV vectors comprises a polynucleotide encoding an IL-1R. In these two different rAAV vectors, the heterologous polynucleotides may be operably linked to transcriptional promoters and/or enhancers which are active under similar conditions or to transcriptional promoters and/or enhancers which are active under different conditions, e.g., independently regulated. In various refinements of administration, the two different rAAV vectors (i.e., one comprising a polynucleotide encoding a TNFR and one comprising a polynucleotide encoding IL-1R) may be administered to the mammal at the same time or at different times, at the same or at different frequencies and/or in the same or at differing amounts.

For any of the above methods, it is understood that one or more rAAV vectors may be administered. For example, as discussed above, a vector may be administered that encodes a TNF antagonist, such as TNF receptor (most preferably sTNFR(p75):Fc). Alternatively, an additional vector may be administered that encodes an IL-1 antagonist, such as an IL-1 receptor polypeptide. Alternatively, a single vector encoding both a TNF antagonist and an IL-1 antagonist may be administered. This single vector may have the coding sequences under control of the same or different transcriptional regulatory elements. If more than one vector is used, it is understood that they may be administered at the same or at different times and/or frequencies.

Further, it is understood that, for any of the above methods, in preferred embodiments, the individual receiving rAAV vector(s) will have cells which contain the rAAV vector (after administration), and most preferably will have cells in which the rAAV vector(s) is integrated into the cellular genome. Stable integration of rAAV is a distinct advantage, as it allows more persistent expression than episomal vectors. Accordingly, in preferred embodiments, cells (i.e., at least one cell) in the individual will comprise stably integrated rAAV. Stated alternatively, for any of the above methods, administration of rAAV(s) results in integration of the rAAV(s) into cellular genomes (although, as is understood by those in the art, not all rAAV vectors need be integrated). Methods of determining and/or distinguishing integrated vs. non-integrated forms, such as Southern detection methods, are well known in art.

Administration of rAAV vectors (preferably packaged as AAV particles) may be through any of a number of routes. A preferred mode of administration is through intramuscular delivery. Intramuscular delivery of the rAAV vectors can reduce TNF levels both in tissue and inter-tissue spaces near the site of injection and also in circulation. Another preferred mode of administration of the rAAV compositions is through intravenous delivery. Another preferred mode of administration of rAAV compositions of the invention is through injection of the composition(s) directly to the tissue or anatomical site. A preferred mode of such an administration is by intra-articular injection of the composition. Preferably, the rAAV composition is delivered to the synovium of the affected joint; more preferably, to synovial cells lining the joint space. Administration to the joint can be single or repeated administrations. Repeated administration would be at suitable intervals, such as about any of the following: once a month, once every 6 weeks, once every two months, once every three months, once every four months, once every five months, once very six months. Repeated administrations may also occur at varying intervals.

Another preferred mode of administration of rAAV compositions of the invention is through naso-pharyngeal and pulmonary routes of administration including, but not limited to, by-inhalation, transbronchial and transalveolar routes. The invention includes rAAV compositions suitable for by-inhalation administration including, but not limited to, various types of aerosols for inhalations, as well as powder forms for delivery systems. Devices suitable for by-inhalation administration of rAAV compositions include, but are not limited to, atomizers and vaporizers.

An effective amount of rAAV (preferably in the form of AAV particles) is administered, depending on the objectives of treatment. An effective amount may be given in single or divided doses. Where a low percentage of transduction can achieve a therapeutic effect, then the objective of treatment is generally to meet or exceed this level of transduction. In some instances, this level of transduction can be achieved by transduction of only about 1 to 5% of the target cells, but is more typically about 20% of the cells of the desired tissue type, usually at least about 50%, preferably at least about 80%, more preferably at least about 95%, and even more preferably at least about 99% of the cells of the desired tissue type.

As an guide, the number of rAAV particles administered per injection will generally be between about $1\times10^6$ and about $1\times10^{14}$ particles, preferably, between about $1\times10^7$ and $1\times10^{13}$ particles, more preferably about $1\times10^9$ and $1\times10^{12}$ particles and even more preferably about $1\times10^{11}$ particles.

The number of rAAV particles administered per joint by intra-articular injection, for example, will generally be at least about $1\times10^8$, and is more typically about $5\times10^8$, about $1\times10^{10}$, and on some occasions about $1\times10^{11}$ particles, including both DNAse resistant and DNAse susceptible particles. In terms of DNAse resistant particles, the dose will generally be between about $1\times10^6$ and about $1\times10^{14}$ particles, more generally between about $1\times10^8$ and about $1\times10^{12}$ particles.

The number of rAAV particles administered per intramuscular injection and per intravenous administration, for example, will generally be at least about $1\times10^{10}$, and is more typically about any of the following: $5\times10^{10}$, $1\times10^{11}$, $5\times10^{11}$, $1\times10^{12}$, $5\times10^{12}$ and on some occasions about $1\times10^{13}$ particles, including both DNAse resistant and DNAse susceptible particles. In terms of DNAse resistant particles, the dose will generally be between about $1\times10^6$ and about $1\times10^{14}$ particles, more generally between about $1\times10^{10}$ and $1\times10^{13}$ particles.

The effectiveness of rAAV delivery can be monitored by several criteria. For example, samples removed by biopsy or surgical excision may be analyzed by in situ hybridization, PCR amplification using vector-specific probes and/or RNAse protection to detect rAAV DNA and/or rAAV mRNA. Also, for example, harvested tissue, joint fluid and/or serum samples can be monitored for the presence of TNF antagonist encoded by the rAAV with immunoassays, including, but not limited to, immunoblotting, immunoprecipitation, immunohistology and/or immunofluorescent cell counting, or with function-based bioassays dependent on TNF antagonist-mediated inhibition of TNF activity. For example, when the rAAV encoded TNF antagonist is a TNFR polypeptide, the presence of the encoded TNFR in harvested samples can be monitored with a TNFR immunoassay or a function-based bioassay dependent on TNFR-mediated inhibition of TNF killing of mouse L929 cells. Examples of such assays are known in the art and described herein.

The invention also provides methods in which administration of rAAV vectors described herein use ex vivo strategies for delivery of polynucleotides to the mammal. Such methods and techniques are known in the art. See, for example, U.S. Pat. No. 5,399,346. Generally, cells are transduced by the rAAV vectors in vitro and then the transduced cells are introduced into the mammal, for example, into an arthritic joint. Suitable cells are known to those skilled in the art and include autologous cells, such as stem cells.

The effectiveness of the methods provided herein may, for example, be monitored by assessment of the relative levels of TNF in harvested tissue, joint fluid and/or serum subsequent to delivery of the rAAV vectors described herein. Assays for assessing TNF levels are known in the art and include, but are not limited to, immunoassays for TNF, including, but not limited to, immunoblot and/or immunoprecipitation assays, and cytotoxicity assays with cells sensitive to the cytotoxic activity of TNF. See, for example, Khabar et al., 1995, *Immunol. Lett.* 46:107–110.

The treated subject may also be monitored for clinical features which accompany the TNF-associated disorder. For example, subjects may be monitored for reduction is symptoms associated with inflammation. For example, after treatment of RA in a subject using methods of the present invention, the subject may be assessed for improvements in a number of clinical parameters including, but not limited to, joint swelling, joint tenderness, morning stiffness, pain, erythrocyte sedimentation rate, and c-reactive protein.

The selection of a particular composition, dosage regimen (i.e., dose, timing and repetition) and route of administration will depend on a number of different factors, including, but not limited to, the subject's medical history and features of the condition and the subject being treated. The assessment of such features and the design of an appropriate therapeutic regimen is ultimately the responsibility of the prescribing physician. The particular dosage regimen may be determined empirically.

The foregoing description provides, inter alia, compositions and methods for reducing the levels of TNF in a mammal. It is understood that variations may be applied to these methods by those of skill in this art without departing from the spirit of this invention.

The examples presented below are provided as a further guide to a practitioner of ordinary skill in the art, and are not meant to be limiting in any way.

EXAMPLES

Example 1

Rat (p80) TNFR:FC Fusion Constructs and Expression of Same

Cloning the Rat (p80) TNFR Extracellular Domain (ECD)

cDNA encoding the extracellular domain (EDC) of the rat p80 TNFR (Type II) was isolated from MARATHON- READY rat spleen cDNA (Clontech) using 5' RACE PCR (Clontech) with a gene-specific PCR primer (5'-CTAACGACGTTAACGATGCAGGTGAC-3') (SEQ ID NO: 15) (Frohman et al., 1988, *Proc. Natl. Acad. Sci. USA* 85:8998–9002). This primer was selected from the 259 bp sequence of the cytoplasmic region of the rat TNFR (p80) gene (Bader et al., 1996, *J. Immunol.* 157:3089–3096). Five separate 5' RACE PCR reactions were performed. The products from each PCR reaction were ligated into pCR 2.1 plasmid (Invitrogen Corporation) followed by transformation into TOP10F' competent cells, using the TOPO TA Cloning® Kit (Invitrogen Corporation). A representative panel of clones were completely sequenced and a full consensus sequence of the rat TNFR (p80) ECD was generated. The cDNA sequence and the amino acid sequence are depicted in FIG. 1. DNA and protein sequence alignments were carried out using the murine p80 TNFR and the human p75 TNFR as reference sequences. FIGS. 2A and 2B depicts a protein alignment of the rat p80 TNFR ECD, the murine p80 TNFR ECD and the human p75 TNFR ECD. The rat TNFR (p80) ECD plasmid was denoted pCRrTNFR.ECD.

Cloning the Rat IgG1 Fc Region

Rat spleen poly(A) RNA was reverse transcribed with Oligo $d(T)_{16}$ as a primer and the IgG1 Fc cDNA (encompassing the hinge, CH2 and CH3 domains) was subsequently amplified using the GeneAmp⊞ RNA PCR Kit (Perkin Elmer) (FIG. 3). PCR primers were designed based on the rat IgG1 sequence (GenBank RAT IGG1Z, Accesion # M28670) (Bruggemann, 1988, *Gene* 74:473–82). The forward,(hinge region) primer: 5'-cggaattcGTGCCCAGAAACTGTGGAG-3' (SEQ ID NO: 16) included an EcoRI site (lower case). The reverse (CH3 region) primer: 5'-gctctagaTCATTTACCCGGAGAGTGG-3' (SEQ ID NO: 17) included an XbaI site. The PCR product was ligated to pCR 2.1 plasmid DNA followed by transformation into TOP10F' competent cells, using the TOPO TA Cloning® Kit (Invitrogen Corporation). A panel of clones were analyzed by restriction enzyme and sequence analyses. The cDNA sequence of the rat IgG1Fc and the corresponding amino acid sequence is depicted in FIG. 4. One clone was used for further manipulations (see below) and was denoted pCRrIgG1Fc.

Generation of Rat (p80) TNFR-Fc Fusion Construct and Expression Vector

To facilitate the fusion of the rat TNFR ECD with the IgG1Fc region (at the hinge region), PCR was used to engineer a NotI restriction site at the 5' end and a KpnI restriction site at the 3' end of the TNFR ECD. For the PCR reactions, plasmid pCRrTNFR.ECD was used as a template, the forward primer (p80-5 NotI) was 5'-CATAAGGGCCCGCAAGAGCGG GAGCTACCGCCG-3' (SEQ ID NO: 18) and the reverse primer (p80-3 KpnI) was 5'-GGTACCCCACCCGTGATGCTTGGTTCAATG-3' (SEQ ID NO: 19). Similarly, PCR was used to engineer a KpnI restriction site at the 5' end of the IgG1Fc (at the hinge region). For this, pCRrIgG1Fc was used as a template, the forward primer (5r IgG1 Fc) was 5'-GGGTACCCAGAAACTGTGGAGGTGATTGC-3' (SEQ ID NO: 20) and the reverse primer (HBRATG1/3') was 5'-GCTCTAGATCATTTACCCGGAGAGTGG-3' (SEQ ID NO: 17).

The site of the sequence fusion was modeled after the human (p75)TNFR:Fc fusion protein (Mohler et al., 1993, *J. Immunol.* 151:1548–1561). The TNFR ECD and IgG1Fc PCR products were ligated via their KpnI restriction sites and subcloned into pCR 2.1. A panel of clones were analyzed by restriction enzyme and sequence analyses. One plasmid with the fusion polynucleotide (pCRrTNFR-Fc) was used for further manipulations. The nucleotide sequence of the rat TNFR:Fc fusion polynucleotide and the encoded amino acid sequence are depicted in FIGS. 5A and 5B.

To construct a mammalian expression vector, the plasmid pCRrTNFR-Fc was digested with NotI restriction enzyme and a 1.6 kb DNA fragment containing the rTNFR-Fc fusion gene was isolated and purified. The mammalian expression plasmid pCMVβ (Clontech) was digested with NotI to remove the β-galactosidase gene and the 3.6 kb plasmid DNA backbone fragment was isolated and purified. The 1.6 kb rTNFR-Fc gene fragment was ligated to the 3.6 kb plasmid backbone and the resulting expression plasmid was designated pCMVrTNFR-Fc (diagrammed in FIG. 6).

Analysis of Expression from pCMVrTNFR-Fc

The expression plasmid pCMVrTNFR-Fc (10 μg) was transfected into 293A cells using LIPOFECTAMINE (Life Technologies). A mock-transfection was included as a negative control. At 48 hours post-transfection, cells were harvested and total cellular RNA was extracted using the Rneasy Mini Kit (Qiagen). RNA samples (10 μg) were subjected to northern blot analysis using a rat TNFR-specific $^{32}P$-labeled probe. A 1.6 kb band corresponding to the rat TNFR-Fc RNA was present only in the RNA sample from pCMVrTNFR-Fc-transfected cells (FIG. 7).

To assess protein expression from the rat TNFR-Fc expression vector, 293 cells in 60 mm dishes were transfected with 10 μg of either pCMVrTNFR-Fc or a control plasmid (pCMVGFP) using LIPOFECTAMINE (Life Technologies). A mock-transfection was also included. At 48 hours post-transfection, cells were washed with PBS and fixed for 10 min in methanol/acetone at room temperature. The cells were then washed with PBS, incubated with blocking buffer for 1 hour at room temperature, washed again with PBS and then incubated with alkaline phosphatase-conjugated anti-rat IgG1 (diluted 1:5000 in PBS) for 1 hour at 37° C. The cells were washed with PBS and were incubated with the alkaline phosphatase detection system 1-STEP NBT/BCIP plus Suppressor (PIERCE) for 2 to 4 hours at room temperature.

Example 2

Generation of rAAV Vectors and Producer Cell Lines rAAV Vectors

The principles of rAAV vector construction follow from the genetics of the virus. Generally, the AAV rep and cap genes are deleted and the cis-acting ITR sequences are retained in the construction of an rAAV vector. Rep and cap functions can be provided by a variety approaches including, but not limited to, those based on transient transfections (see, for example, Samulski et al., 1989; Flotte et al., 1995, *Gene Ther.* 2:29–37) and those based on stable cell lines (see, for example, Clark et al., 1995, *Hum. Gene Ther.* 6:1329–1341; Tamayose et al., 1996, *Hum. Gene Ther.* 7:507–513) to allow for rAAV virus generation.

Construction of the AAV Vector Plasmid pAAVCMVrTNFR-Fc

The expression plasmid pCMVrTNFR-Fc DNA was digested with NotI and XbaI restriction enzymes and the 1.6 kb DNA fragment containing the rat TNFR-Fc fusion gene was isolated and purified. An rAAV vector plasmid, pAAVflagLUC, was digested with NotI and XbaI restriction enzymes to remove the flagLUC DNA fragment and the rAAV vector backbone was isolated and purified. The 1.6 kb rat TNFR-Fc gene fragment was then subcloned into the NotI and XbaI restriction sites of the rAAV vector plasmid. The diagram in FIGS. 8A, 8B and 8C depicts the resulting rAAV vector in which the rat TNFR-Fc fusion polynucleotide is located between, and operably linked to, the human immediate early CMV enhancer promoter and a synthetic polyA addition signal. The transcription unit containing the TNFR-Fc fusion gene is enclosed between the AAV-2 ITRs. This rAAV vector plasmid was denoted pAAVCMVrTNFR-Fc.

Generation of a Stable Producer Cell Line for AAVCMVrTNFR-Fc

Generally, rAAV producer cell lines are generated by transfection of cells with vector plasmid, followed by selection with antibiotics (typically G418, hygromycin, or histidinol) and cloning of individual colonies. Colonies are first screened for vector replication. Clones showing high level replication of vector following adenovirus infection are then tested for production of infectious vector.

Plasmid pAAVCMVrTNFR-Fc (30 μg) was transfected into the Hela C12 packaging cell line by electroporation (Potter et al., 1984, *Proc. Natl. Acad. Sci. USA* 79:7161–7165). The C12 cell line contains the AAV2 rep and cap genes that are transcriptionally quiescent until induction upon infection with adenovirus helper (Clark et al., 1995; Clark et al., 1996, *Gene Therapy* 3:1124–1132). Twenty four hours post-transfection, the cells were trypsinized and replated in 100 mm plates at densities ranging from $5\times10^3$ to $5\times10^4$ cells per plate. The cells were subjected to selection in DMEM containing 10% fetal bovine serum and 300 μg/ml hygromycin B. Drug-resistant cell clones were isolated, expanded and their ability to produce infectious AAVCMVrTNFR-Fc vectors was tested and compared in an infectivity assay as described in Atkinson et al., 1998, *Nucleic Acid Res.* 26:2821–2823. One such producer cell clone (C12-55) was further used for production of AAVCMVrTNFR-Fc vector. Production, purification and titration were carried out essentially as described herein and as generally described in Atkinson et al. (WO 99/11764).

Example 3

Rat TNFR-FC as a TNF Antagonist

Expression of Rat TNFR-Fc Activity after Transfection with pCMVrTNFR-Fc

Cells were transfected with the rat TNFR-Fc expression vector to determine (1) whether rat TNFR-Fc would be secreted from cells and (2) whether rat TNFR-Fc had the ability to neutralize TNF-α activity.

293 cells ($2\times10^6$) in T-75 flasks were transfected with either 10 μg of pCMVrTNFR-Fc or pCMVGFP using LIPOFECTAMINE (Life Technologies, Inc.). After 48 hours, the medium was collected and tested in a TNF-α inhibition bioassay as follows. Mouse fibrosarcoma WEHI-13var cells (ATCC, CRL-2148) were seeded in 96-well microplate at $4\times10^4$ cells per well in 100 μl RPMI 1640 medium containing 10% fetal bovine serum. After overnight incubation, actinomycin D (1 μg/ml) and recombinant rat TNF-α (0.75 ng/ml; BioSource International, PRC 3014) were added to each well in a total volume of 100 μl. Samples of medium from the transfected 293 cells were added to the first row of wells and serially diluted 2-fold, in triplicate. The cells were incubated overnight at 37° C. supplemented with 5% $CO_2$. The next day, 50 μl of XTT labeling mixture (Cell proliferation kit, Boehringer Mannheim, #1-465-015) was added to each well, and the cells were incubated at 37° C. for 4 hours. Finally, the plate was placed in Spectra MAX 250 plate reader (Molecular Devices) and the absorbance at 490 nm was recorded using Delta Soft analysis software. The absorbance measured directly correlates to the cell number and thus, to cell proliferation in the assay. If not inhibited, TNF-α induces cell death in this assay.

Figure 9:
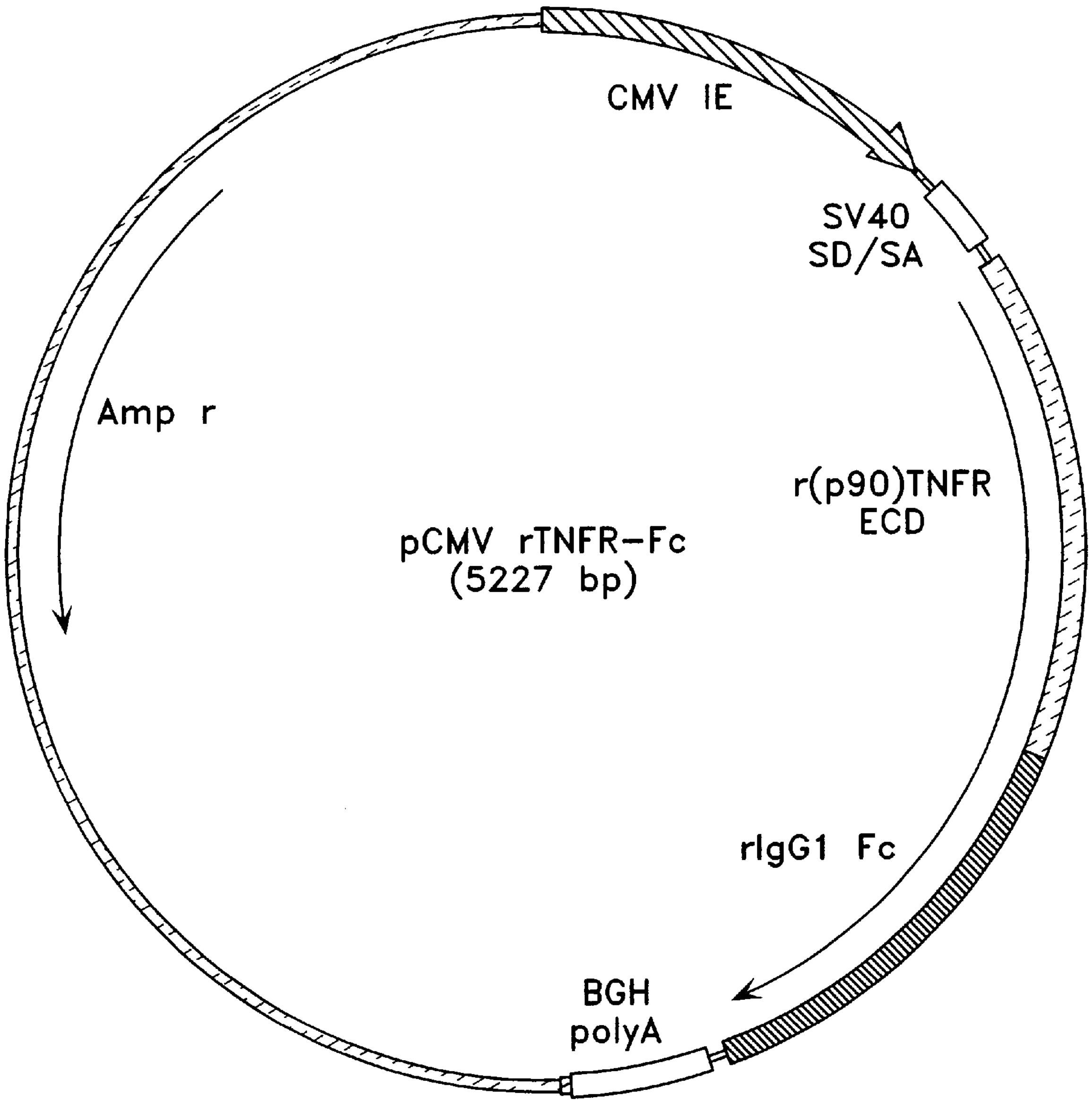
FIG. 9 depicts a diagram of the pCMVrTNFR-Fc expression plasmid, including the rat TNFR(p80)ECD-IgG1Fc fusion polynucleotide and operatively linked control elements.

Results from such a TNF inhibition bioassay are depicted in FIG. 9 and demonstrate that pCMVrTNFR-Fc-transfected 293 cells expressed and secreted the rat TNFR-Fc fusion protein into the medium and that this TNFR-Fc protein inhibited killing of WEHI- 13var cells by TNF-α in a dose-dependent manner. Medium from pCMVGFP-transfected 293 cells appeared to have no effect on TNF-α activity.

Rat TNFR-Fc Activity After Transduction with AAVCMVrTNFR-Fc

Cells were infected with the rAAV virus particles to determine whether transduced cells could express and secrete rat TNFR-Fc. The rat TNFR-Fc produced from the transduced cells was also tested for the ability to act as a TNF antagonist.

Figure 10:
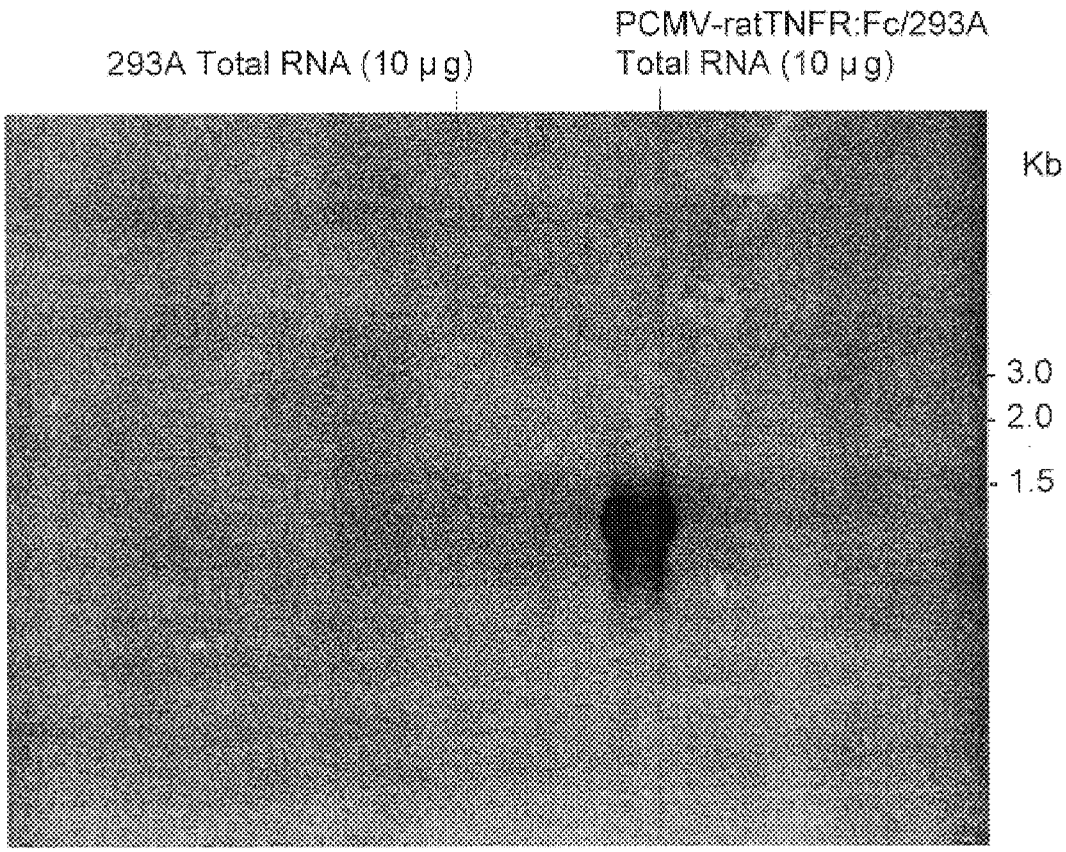
FIG. 10 depicts a northern analysis of RNA from cells tranfected with the pCMVrTNFR-Fc expression plasmid.

293 cells in a 24-well plate were mock-infected, infected with a LacZ gene-containing AAV vector (Clark et al., 1995; Clark et al., 1996) or with AAVCMVrTNFR-Fc at $10^4$ particles per cell. The infected cells were maintained in DMEM containing 10% fetal bovine serum (1 ml per well). Forty eight hours post-infection, the media was collected and samples ranging from 0.3125 μl to 20 μl were analyzed in a TNF-α inhibition assay, as described above. 293 cells transduced with AAVCMVrTNFR-Fc, but not cells transduced with the LacZ gene-containing vector (D6) nor mock-infected cells, expressed and secreted a TNFR-Fc polypeptide with TNF-α neutralizing activity (FIG. 10).

Figure 11:
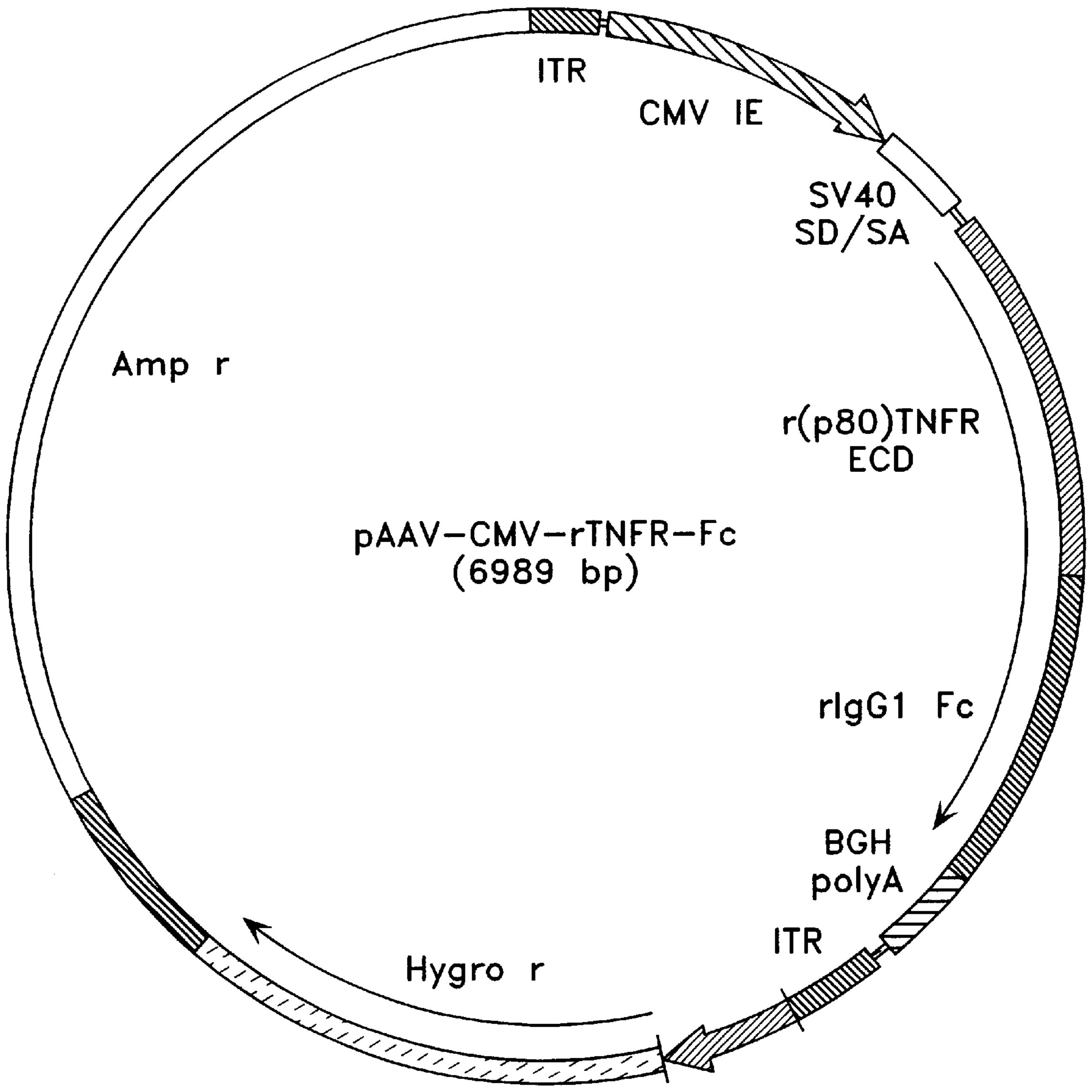
FIG. 11 depicts a diagram of the rAAV vector plasmid pAAVCMVrTNFRFc, including the rat TNFR(p80)ECD- IgG1Fc fusion polynucleotide, operatively linked control elements, including AAV ITRs.
Figure 12:
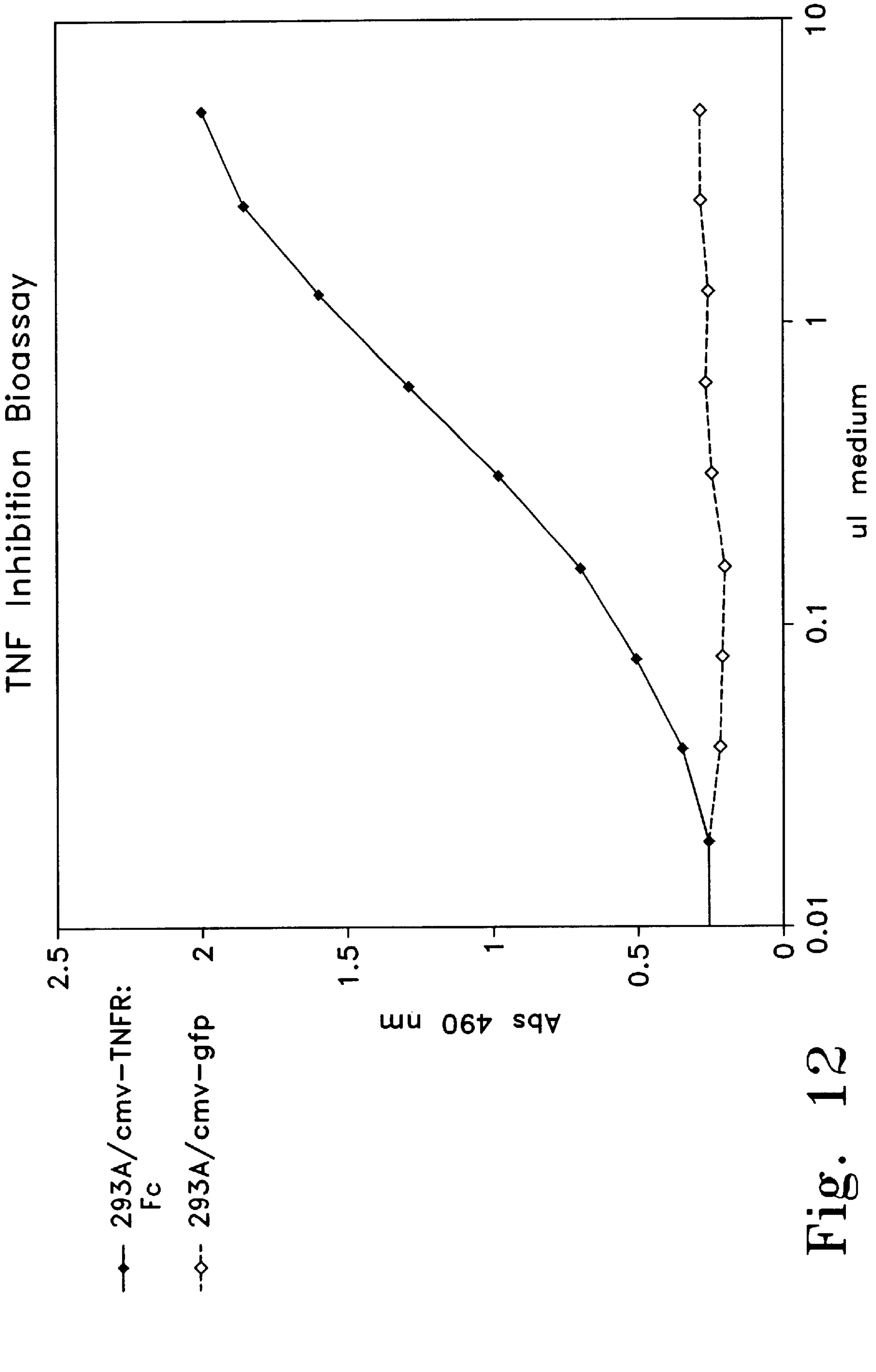
FIG. 12 is a graph depicting the results of TNF inhibition bioassays using media collected from cells transfected with pCMVrTNFR-Fc (-◆-) and from cells transfected with pCMVGFP (-◇-).

In another experiment, 293 cells were either mock-infected or infected with AAVCMVrTNFR-Fc vector at $10^2$, $5\times10^2$, $10^3$, $5\times10^3$ and $10^4$ particles per cell. At 48 hours post-infection, the media were collected and subjected to a TNF-α inhibition assay as described above. The rat TNFR-Fc protein was secreted from transduced cells in a dose-dependent manner (FIG. 11). Time-course analysis of TNFR-Fc protein expression after transduction of 293 cells with AAVCMVrTNFR-Fc at $10^3$ particles per cell showed a steady increase in secretion of a TNFR-Fc protein with TNF-α antagonist activity over 120 hours (FIG. 12).

Example 4 rAAV Vector Delivery to Joints

AAV vectors have been shown to mediate efficient and persistent gene delivery to a variety of tissue targets in vivo. These targets have included airway epithelium, vasculature, muscle, liver, and central nervous system. See, for example, Flotte et al., 1993, *Proc. Natl. Acad. Sci. USA* 90:10613–10617; Lynch, et al., 1997, Circ. Res. 80:497–505; Kessler et al., 1996, *Proc. Natl. Acad Sci. USA* 93:14082–14087; Xiao et al., 1996, *J. Virol.* 70:8098–8108; Koeberl et al., 1997, *Proc. Natl. Acad. Sci. USA* 94:1426–1431; Snyder et al., 1997, *Nat. Genet.* 16:270–276; and Kaplitt et al., 1994, *Nat. Genet.* 8:148–154. In several cases, expression of a reporter transgene delivered with an rAAV vector has been documented for greater than one year. Animal studies with the AAV vector system have in general shown little or no pathogenicity or immunogenicity, in contrast to other viral vector systems.

In a pilot study, 5 normal rats were injected in the hind paw joints with $10^{11}$ n DNase resistant particles (DRP) of an rAAV containing the LacZ gene, rAAV-LacZ. Detection of incorporation of the rAAV vector into the genome would be monitored by the production of the LacZ encoded polypeptide, β-galactosidase. The rats were observed for 30 days for indications of inflammation such as joint redness, swelling and pain. No indication of inflammation was seen in these animals in contrast to rats injected with *M. tuberculosis* in incomplete Freund's adjuvant which developed overt inflammation as indicated by joint swelling, redness, tenderness.

The animals were sacrificed at day 30, the joints examined and joint tissue scraped for assessment of gene expression by luminescence readout of β-galactosidase activity. No gross inflammation was seen, the joints appeared identical to uninjected joints, in contrast with adjuvant injected rats which exhibited marked cellularity. Luminescence measurement showed $52 \times 10^4$ RLU in the rAAV injected joint while the background level was $3.5 \times 10^4$ RLU. Despite the high background of endogenous β-galactosidase found in joint tissue, the results of this experiment indicate that rAAV vectors are capable of successfully transducing cells found in the joint.

In summary, preliminary experiments in normal rats suggest that rAAV vectors mediates the transduction of cells found in proximity to the joint space following intra-articular injection of vector.

Example 5 rAAV Vector Delivery to Joints in a Rodent Model of Arthritis

A study was conducted using rAAV vector gene transfer in the streptococcus cell wall model of arthritis. The rat model used in these studies is an art-accepted and FDA-accepted model for studying arthritis and is used for evaluating anti-cytokine therapies.

In this study, rats treated with intraperitoneal injection of Group A streptococcus cell wall to induce arthritis were also co-administered an intra-articular injection of $8.6 \times 10^9$ DRP of rAAV-LacZ vector. Animals were sacrificed on day 5 following vector administration. Rats that received the streptococcal cell wall preparation developed arthritis irrespective of rAAV-LacZ vector administration.

Figure 13:
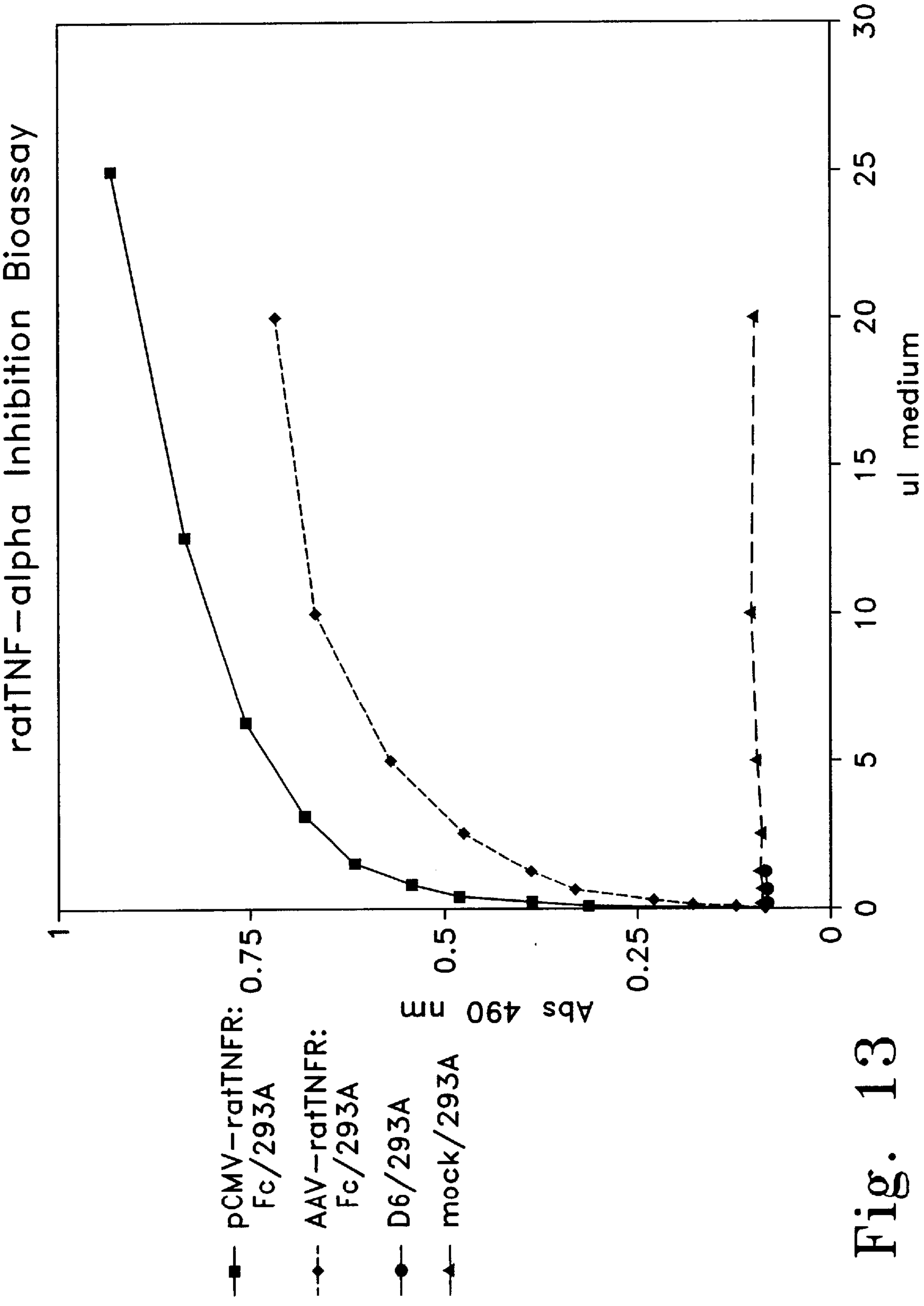
FIG. 13 is a graph depicting results of TNF inhibition bioassays using media from cells transduced with AAVCMVrTNFRFc particles (◆), from cells transduced with AAV-lacZ particles (●), from mock infected cells (▲) and from cells transfected with pCMVrTNFR-Fc (■).
Figure 14:
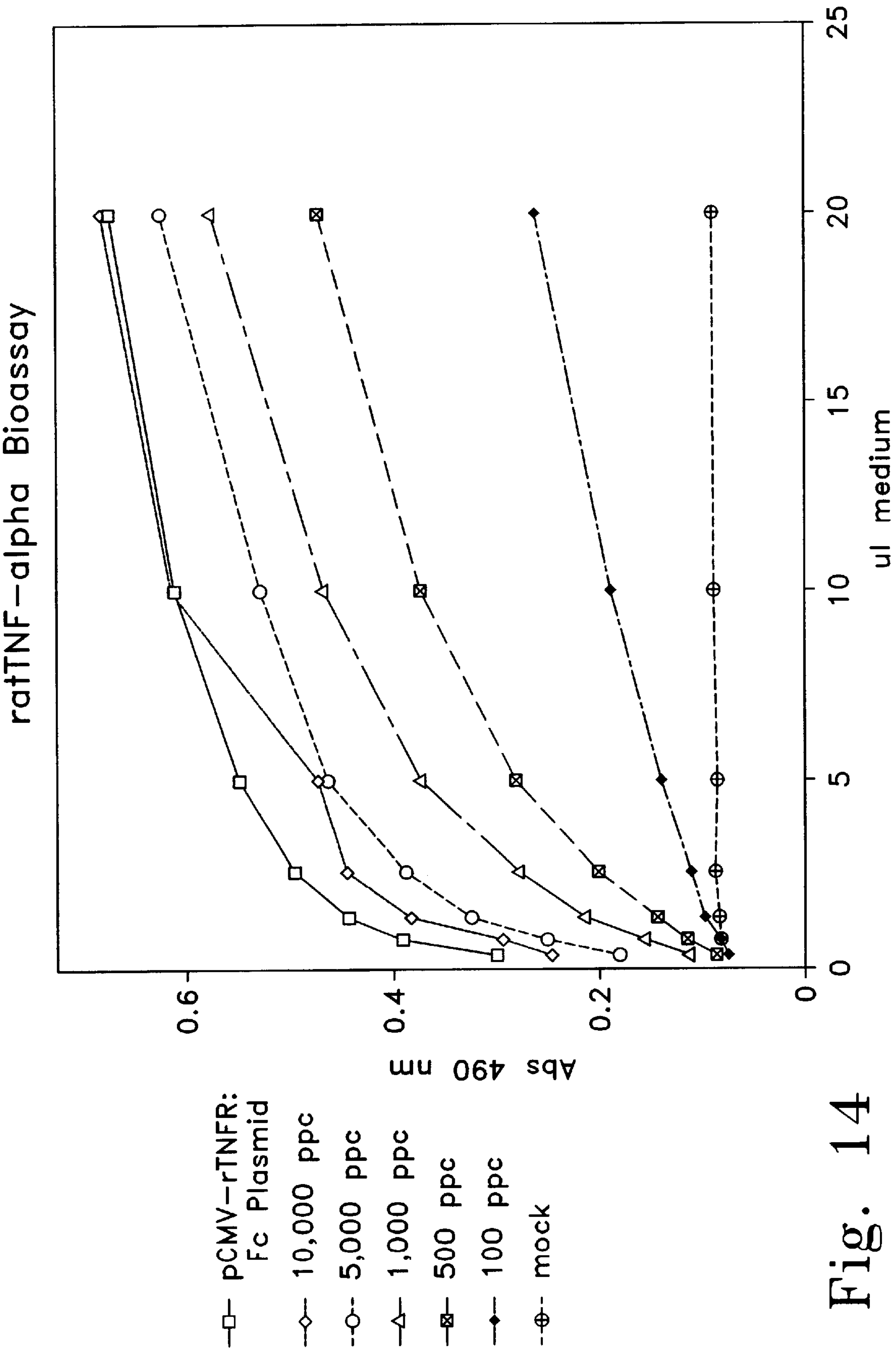
FIG. 14 is a graph depicting results of TNF inhibition bioassays using media from cells transduced with AAVCMVrTNFRFc particles at 100 (◆), 500 (⊞), 1000 (Δ) 5000 (○), or 10,000 (◇) particles per cell, as well as with media from mock infected cells (⊕) and from cells transfected with pCMVrTNFR-Fc (□).
Figure 15:
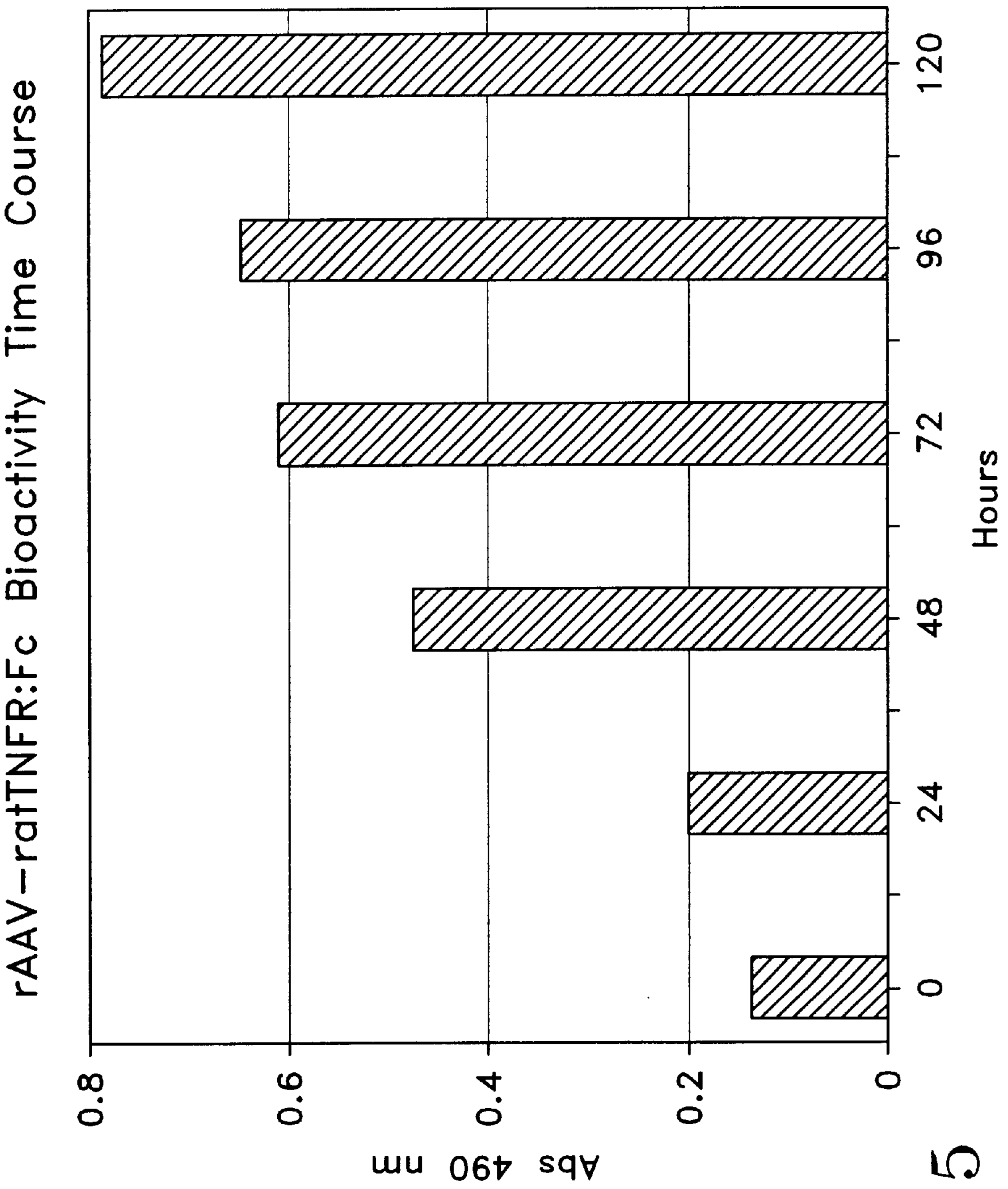
FIG. 15 is a graph depicting a time course analysis of TNFR-Fc polypeptide expression after transduction of cells with AAVCMVrTNFRFc at 1000 particles per cell. The expression of TNFR-Fc was determined with TNF inhibition bioassays.
Figure 16:
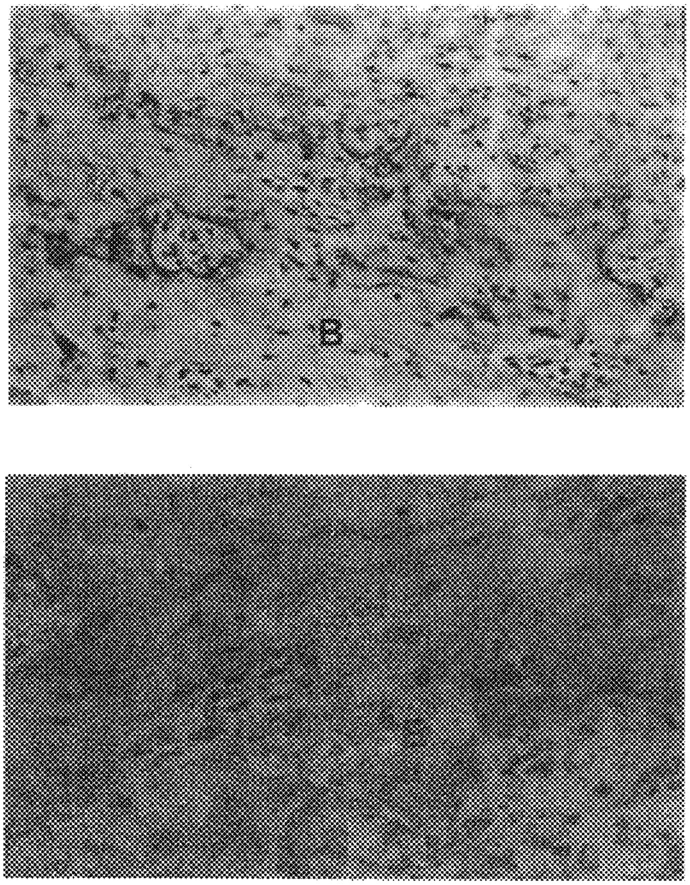
FIG. 16 is a photograph of joint tissue treated with rAAV-LacZ and histochemically stained for β-galactosidase activity.
Figure 17:
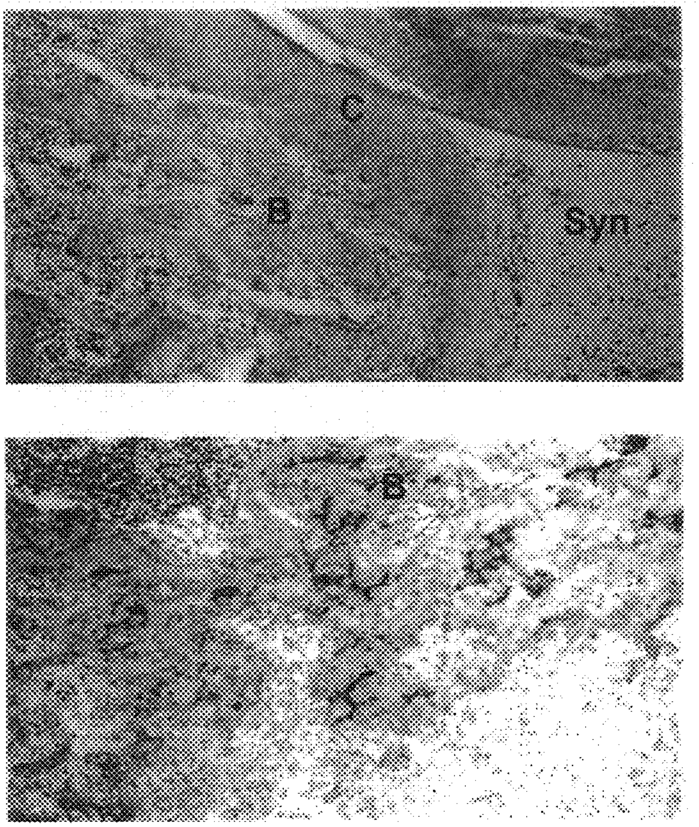
FIG. 17 is a photograph of arthritic joint tissue treated with rAAV-LacZ and histochemically stained for β-galactosidase activity.
Figure 18:
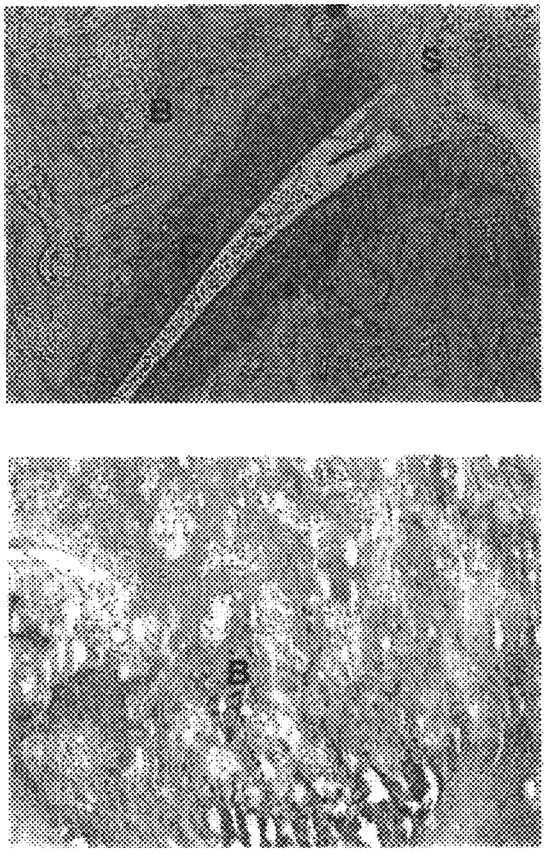
FIG. 18 is a photograph of arthritic joint tissue treated with PBS and histochemically stained for β-galactosidase activity.

Histochemical staining for β-galactosidase activity resulted in the presence of β-galactosidase activity (blue reaction product) in rAAV-LacZ treated (FIGS. 13 and 14) but not control treated (FIG. 15) joints. Very dark blue-black cells were seen in synovium of rAAV-LacZ treated animals and lighter blue cells were localized to the bone stroma underlying the joint space. At this time point, neither the cartilage nor cancellous bone appeared to be transduced by the vector.

In summary, preliminary experiments in a rat model of arthritis suggest that rAAV vectors mediates the transduction of cells found in proximity to the joint space following intra-articular injection of vector.

Example 6 rAAV-ratTNFR:FC Vector Gene Therapy in Rodent Model of Arthritis

Vectors. Recombinant AAV-ratTNFR:Fc (see above examples) and AAV-EGFP vectors were produced from their corresponding stable HeLa C12 producer cell lines, C12/AAV-ratTNFR:Fc and C12/AAV-EGFP, respectively. AAV-EGFP encodes the red-shifted enhanced green fluorescent protein (EGFP) form the bioluminescent jellyfish *Aequorea victoria* (Heim et al., 1995, *Nature* 373:663–664; Cormack et al., 1996, *Gene* 173:33–38). This gene cassette includes a CMV immediate-early (IE) enhancer/promoter and a bovine growth hormone (BGH) polyadenylation (poly A) signal. It was included in the experiments as vector control (unrelated gene). Cells were grown in cell factories and vectors were produced from lysates prepared 3 days after infection with helper Ad5 (moi 10). Cell lysates were microfluidized through an 18 gauge orfice at 10,000 PSI. The vector was then banded by CsCl gradient centrifugation, dialyzed and further purified through a PI column. Finally, the purified vector bulk was dialyzed against Ringer's buffer saline solution (RBSS) plus 4% Glycerol, sterile filtered, aliquated and stored at $-80°$ C. DNase I-Resistant Particle (DRP) titers were determined by slot blot analyses and were $7.6 \times 10^{11}$ DRP/mL and $2.8 \times 10^{12}$ DRP/mL for AAV-ratTNFR:Fc and AAV-EGFP vectors, respectively. Clark et al., 1995, *Human Gene Therapy* 6:1329–1341. Infectious titers were determined by infectious center assays and were $1 \times 10^{10}$ i.u/mL and $5.2 \times 10^9$ i.u./mL for AAV-ratTNFR:Fc and AAV-EGFP vectors, respectively. Yakobson et al., 1987, *J. Virol.* 61:972–981; Zolotukhin et al., 1999, *Gene therapy* 6:973–985.

SCW-induced arthritis model. In this experimental model of arthritis, the disease was initiated by a single intraperitoneal (i.p.) injection of group A SCW peptidoglycan-polysaccharide (PG-APS) (30 μ/gr body weight) (Lee Laboratories Inc., Grayson, Ga.) into 4-week old (100 gr) genetically susceptible female Lewis rats (Charles River Breeding Laboratories, Wilmington, Mass.) (Cromartie, et al., 1977, *J. Exp. Med* 146:1585–1602). Typically, this model exhibits a peripheral and symmetrical, biphasic polyarthritis with cycles of exacerbated recurrence and remission and is clinically and histologically similar to RA (Cromartie, et al., 1977). An acute inflammation of the rear ankles developed within 24–48 hours, which persisted for 4–5 days, and then partially resolved. This acute, neutrophil-predominant, inflammatory response was then followed by a spontaneously reactivating chronic inflammation at approximately day 15, which developed into a chronic, progressive, erosive synovitis. In addition to polyarthritis, this PG-APS model induced chronic granulomatous inflammation of the liver and spleen. The severity of arthritis (articular index, AI) was determined by scoring each ankle based on the degree of swelling, erythema, and distortion on a scale of 0–4 and summing the scores for all limbs.

Intra-muscular and intra-articular injections. Rats were anaesthetized with Isoflurane (5% with $O_2$ for induction and 3% for maintenance). Twenty microliters of either AAV-ratTNFR or AAV-EGFP vectors ($2 \times 10^{10}$ DRP) or an equivalent volume of RBSS plus 4% Glycerol (vehicle) were injected into the rear ankle joint using a 30-gauge needle adapted to a Hamilton syringe. Intra-muscular injections of either vehicle or recombinant AAV vectors ($1.2 \times 10^{11}$ DRP in 150 μL) were carried out using a 25-gauge needle.

TNFR:Fc bioassay. Blood samples (300 μL) were collected from tail-vein before (pre-bleed), and 5 (acute phase), 11 (remission) and 33 (chronic phase) days after SCW-injection. Serum samples (50 μL) were assayed for bioactive rat TNFR:Fc Fusion protein in a standard TNF-α bioassay adapted for inhibition studies (Khabar et al., 1995, *Immunol. Lett.* 46:107–110). In this assay, inhibition of TNF-α (750 pg/mL)-mediated killing of sensitive WEHI-13VAR cells by soluble rat TNFR:Fc is determined by increased absorbance at OD490 nm.

Summary

We evaluated AAV-ratTNFR:Fc vector gene therapy in an experimental rat model of arthritis. The streptococcal cell wall (SCW)-induced arthritis model in Lewis rats was employed to evaluate the effect of AAV-ratTNFR:Fc vector administration on the severity of arthritis on both the ipsilateral and the contralateral joints.

Intra-peritoneal injection of SCW followed by a single intra-articular administration of $2\times10^{10}$ DNase I-resistant particles (DRP) of AAV-ratTNFR:Fc vector to both rear ankle joints resulted in significant reduction of hind paw swelling as measured by arthritis index (Al) scores. Moreover, intra-peritoneal injection of SCW followed by administration of AAV-ratTNFR:Fc vector to a single joint also resulted in significant reduction of paw swelling in the contralateral joint. A single intra-muscular administration of $1.2\times10^{11}$ DRP of AAV-ratTNFR:Fc vector resulted in a similar effect. As expected, intra-peritoneal injection of SCW followed by intra-articular or intra-muscular administration of an AAV vector encoding an unrelated gene expression cassette (AAV-EGFP) did not exacerbate joint inflammation but also did not result in any therapeutic effect. Bioactive rat TNFR:Fc protein was readily detectable at day 33 in serum samples of rats injected intra-muscularly with AAV-ratTNFR:Fc vector. In contrast, serum bioactive rat TNFR:Fc protein levels in intra-articularly-injected rats were not significantly different from control rats (RBSS or AAV-EGFP-treated rats), suggesting that local administration of AAV-ratTNFR:Fc vector does not lead to significant systemic exposure of this TNF-α antagonist.

Results

The experiments described below were carried out using the group A SCW-induced arthritis model in rats. A total of 65 four-week old female Lewis rats were divided into 3 groups and treated as follows:

Group 1

N=8, Day 0: SCW (i.p.) and AAV-ratTNFR:Fc (intra-articular, both rear ankles; $2\times10^{10}$ DRP/joint)

N=8, Day 0: SCW (i.p.) and AAV-ratTNFR:Fc (intra-articular, one rear ankle joint; $2\times10^{10}$ DRP/joint)

N=4, Day 0: SCW (i.p.) and AAV-ratTNFR:Fc (intra-muscular; $1.2\times10^{11}$ DRP/muscle)

N=6, Day 0: SCW (i.p.) and AAV-EGFP (intra-articular, both rear ankles; $2\times10^{10}$ DRP/joint)

N=4, Day 0: SCW (i.p.) and AAV-EGFP (intra-muscular; $1.2\times10^{11}$ DRP/muscle)

Group 2

N=4, Day 0: SCW (i.p.) and RBSS (intra-articular, both rear ankles)

N=5, Day 0: SCW (i.p.)

Group 3

N=4, Day 0: AAV-ratTNFR:Fc (intra-articular, both rear ankles; $2\times10^{10}$ DRP/joint)

N=4, Day 0: AAV-ratTNFR:Fc (intra-muscular; $1.2\times10^{11}$ DRP/muscle)

N=4, Day 0: AAV-EGFP (intra-articular, both rear ankles; $2\times10^{10}$ DRP/joint)

N=4, Day 0: AAV-EGFP (intramuscular; $1.2\times10^{11}$ DRP/muscle)

N=3, Day 0: RBSS (intra-articular, both rear ankles)

Figure 19:
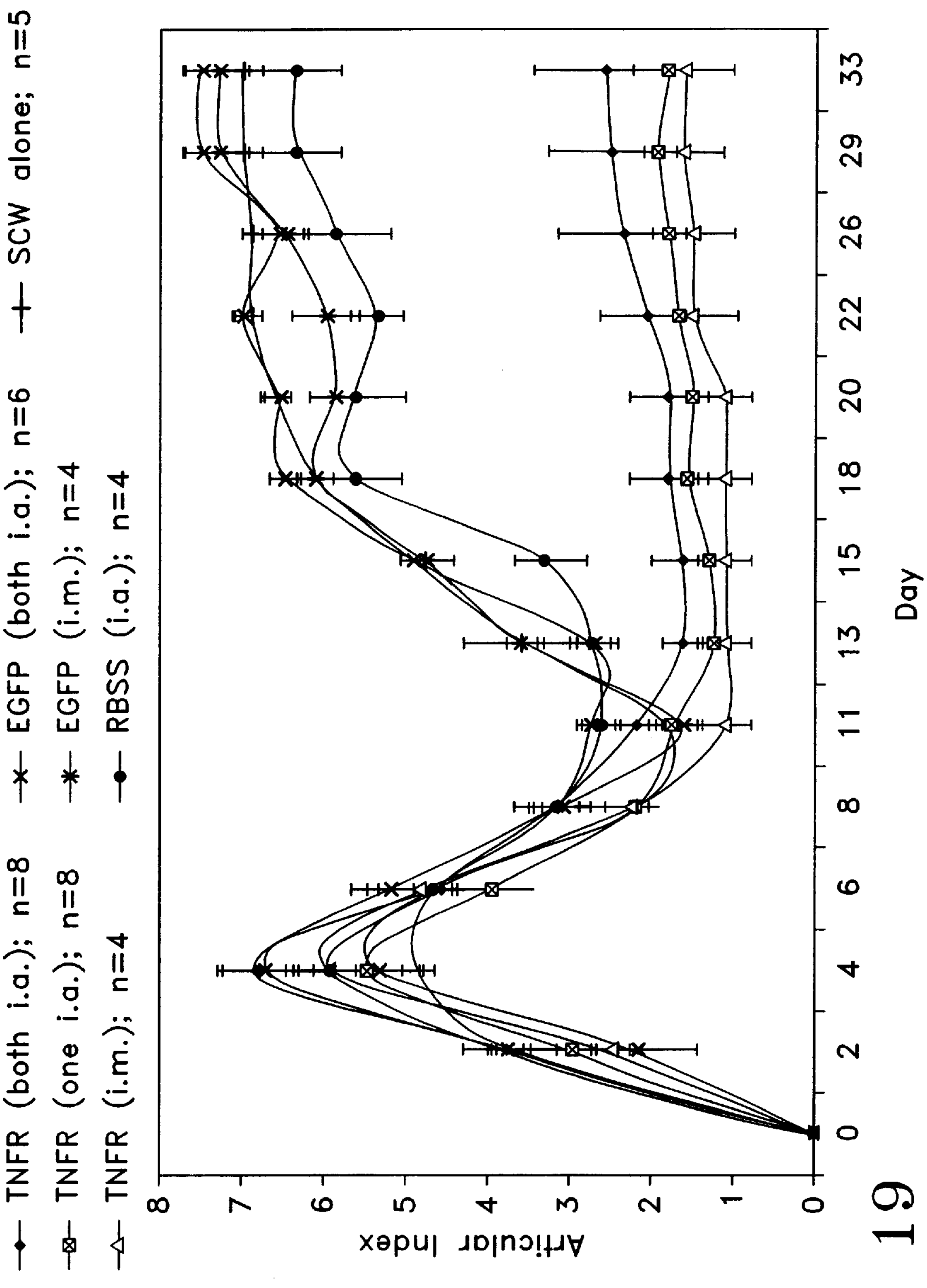
FIG. 19 is a graph depicting suppression of SCW-induced arthritis by rAAV-ratTNFR:Fc vector. Each point represents the mean +/− standard error from the mean (SEM) for each group of rats.
Figure 20:
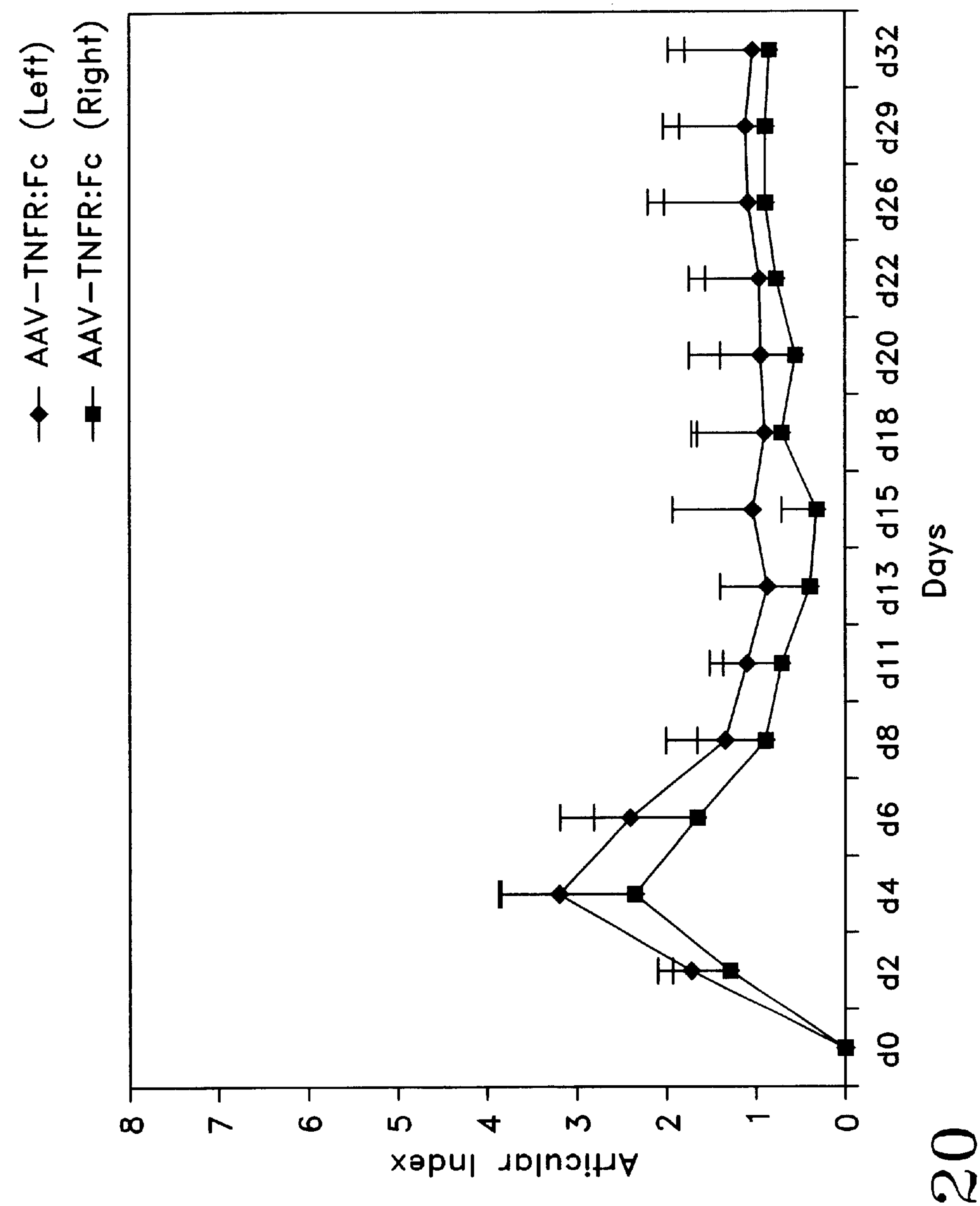
FIG. 20 is a graph depicting suppression of arthritis symptoms in the contralateral joint by AAV-ratTNFR:Fc vector. The Al scores for each rear ankle paw was separately recorded and plotted. Each point represents the mean +/− standard error from the mean (SEM) for each group of rats.
Figure 21:
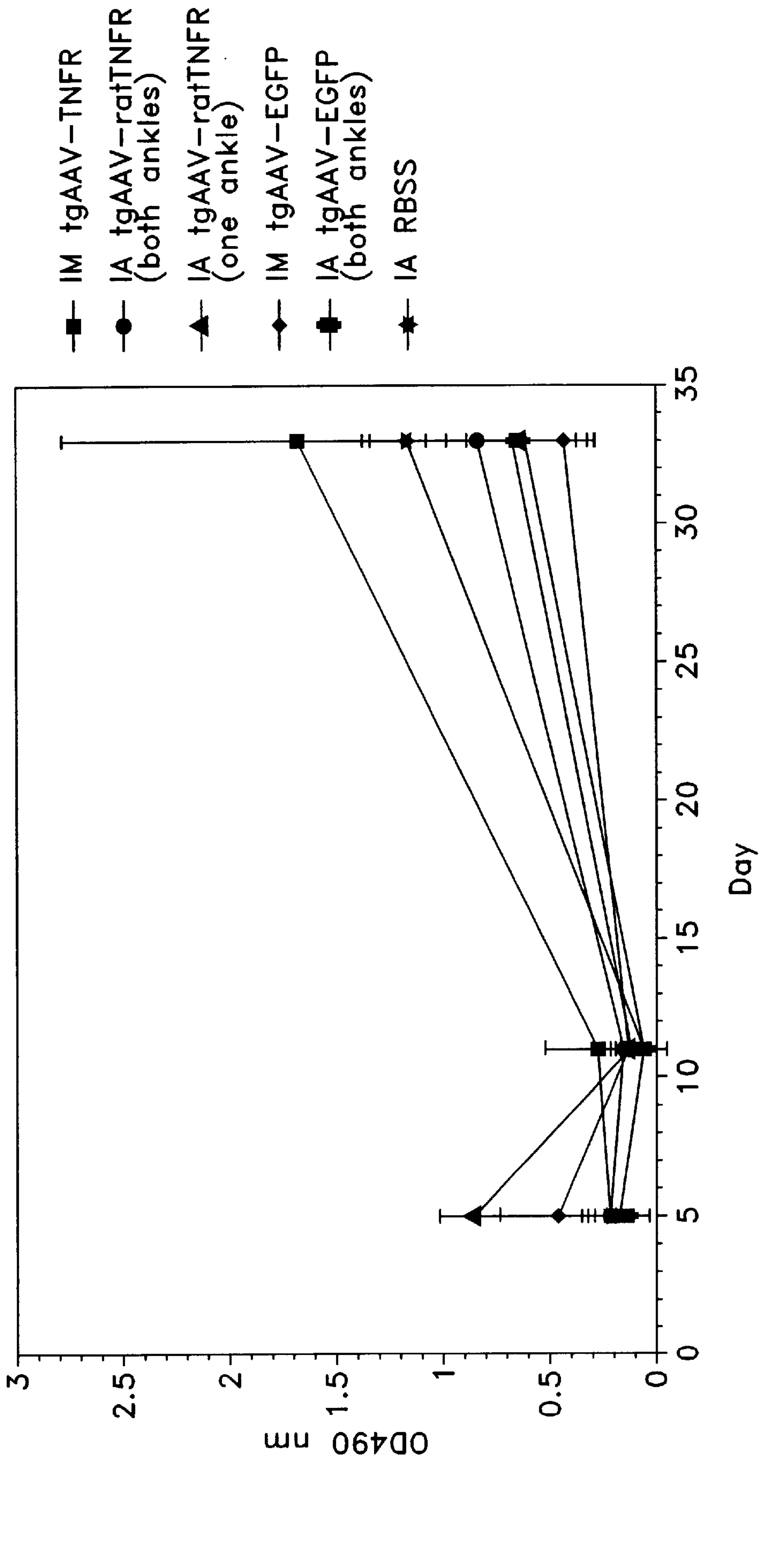
FIG. 21 is a graph depicting serum expression of bioactive rat TNFR:Fc protein in SCW-treated rats. Each point represents the mean +/− standard deviation (SD) for each group of rats.
Figure 22:
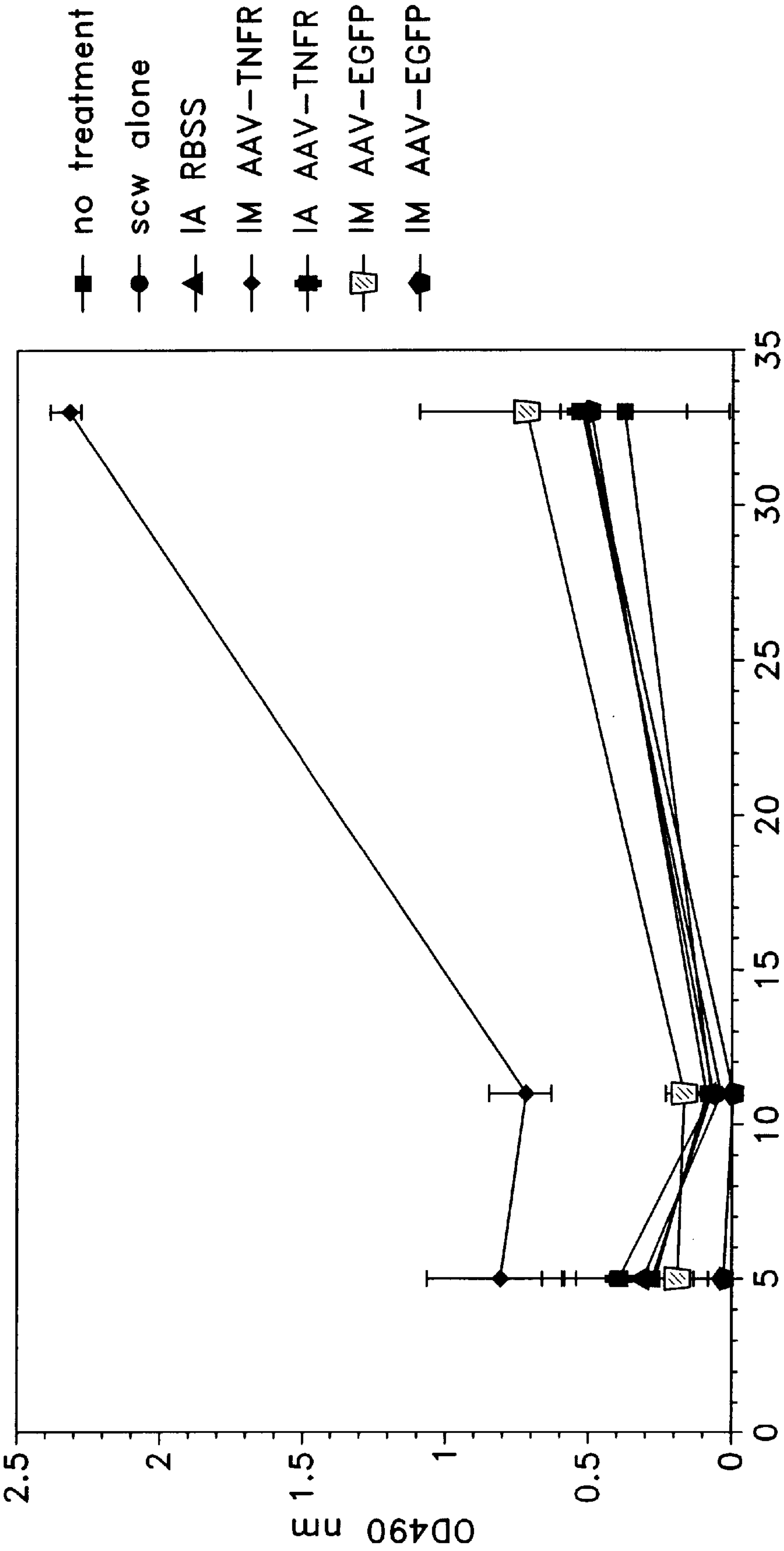
FIG. 22 is a graph depicting serum expression of bioactive rat TNFR:Fc protein in naive rats. Each point represents the mean +/− standard deviation (SD) for each group of rats.

Rats were inspected daily for disease onset and progression, and the severity of arthritis (AI) was recorded every 2 to 3 days. FIG. 19 shows that intra-peritoneal injection of arthritogenic dose (30 μg/gr body weight) of SCW on Day 0 either alone or in combination with intra-articular administration of RBSS into both rear ankle joints resulted in a typical acute inflammatory response that peaked on day 4 (mean AI=6) and then decreased to its minimum by day 11 (mean AI=2). Remission was followed by recurrence of joint swelling that plateaued by day 22 (mean AI=7) and remained chronic until the animals were sacrificed (day 35). As expected, intra-peritoneal injection of SCW followed by a single intra-articular administration of $2\times10^{10}$ DRP of AAV-ratTNFR:Fc vector to both rear ankle joints did not have a significant affect on joint swelling during the acute phase. In contrast, the effect of the latter treatments resulted in significant reduction of hind paw swelling during the chronic phase as measured by AI scores (mean AI=2). Interestingly, administration of AAV-ratTNFR:Fc vector to one joint produced significant and similar therapeutic effects on both the ipsilateral as well as the contralateral joint (see also FIG. 20). FIG. 20 shows that animals were injected intra-peritoneally with SCW (30 μg/gr body weight) on day 0 followed by a single administration of AAV-ratTNFR:Fc (total of $2\times10^{10}$ DRP) into the left rear ankle joint. The AI scores for each rear ankle paw was separately recorded. A single intra-muscular administration of $1.2\times10^{11}$ DRP of AAV-ratTNFR:Fc vector following intra-peritoneal injection of SCW resulted in a similar effect. Intra-peritoneal injection of SCW followed by intra-articular or intra-muscular administration of an AAV vector encoding the green fluorescent gene (AAV-EGFP) did not exacerbate joint inflammation but also did not result in any therapeutic effect. Finally, administration of either AAV-ratTNFR:Fc or AAV-EGFP to naive rat joints did not induce visible joint swelling. From this experiment we concluded that administration of AAV-ratTNFR:Fc but not AAV-EGFP vector either to the joint or to the muscle results in production of therapeutic levels of soluble bioactive rat TNFR:Fc protein that binds and significantly inhibit the inflammatory activity of TNF-α. Although administration of AAV-EGFP vector did not result in any therapeutic effect, it did not exacerbate the inflammatory process in the affected joints, and did not induce inflammation in the joints of naïve animals, indicating that recombinant AAV vector delivery locally to the joint is safe. One possible explanation for the noted contralateral effect is that expression of the rat TNFR:Fc gene in transduced joint tissue leads to secretion of this protein to the circulation which then gains access to uninjected inflamed joints. To test this hypothesis, serum samples from both na ïve and SCW-treated animals were assayed for bioactive rat TNFR:Fc protein in a TNF-α inhibition bioassay (Khabar et al., 1995) after administration of AAV-ratTNFR:Fc to the joint or to the muscle. FIGS. 21 and 22 show that bioactive rat TNFR:Fc protein was readily detectable by day 33 after intra-muscular administration of AAV-ratTNFR:Fc vector. In contrast, the circulating levels of bioactive rat TNFR:Fc protein from intra-articularly injected animals were low and non-significantly different from those of control animals (AAV-EGFP or RBSS-treated rats). We concluded that the contralateral effect is unlikely due to secretion and systemic distribution of the rat TNFR:Fc protein.

Discussion

We described here an in vivo study using an art-accepted model of arthritis aimed at evaluating recombinant AAV-mediated TNFR:Fc gene delivery for the treatment of inflammatory joint disease. We employed the SCW-induced arthritis model in rats to evaluate the therapeutic effect of local (intra-articular) and systemic (intra-muscular) administration of AAV-ratTNFR:Fc vector on the severity of arthritis.

Our results show that intra-articular administration of AAV-ratTNFR:Fc vector significantly reduced the severity of SCW-induced arthritis in the absence of detectable bioactive rat TNFR:Fc protein in the circulation. Intra-muscular administration of AAV-ratTNFR:Fc vector was also effective in reducing arthritis symptoms and as expected bioactive rat TNFR:Fc protein was readily detectable in the serum.

Administration of AAV-ratTNFR:Fc or AAV-EGFP to the joints of naive rats did not induce a detectable inflammatory response in the injected paws and intra-articular administration of AAV-EGFP vector to SCW-treated rats did not exacerbate the inflammatory joint disease, indicating that local intra-articular administration of recombinant AAV vectors is safe.

Interestingly, a single administration of this vector to one joint resulted in a similar therapeutic effect on both the ipsilateral and the uninjected contalateral joint. The phenomenon of a therapeutic contralateral effect was first reported by Ghivizzani et al. (1998, *Proc. Natl. Acad Sci. USA* 95:4613–4618) who noted that adenoviral delivery of soluble interleukin 1 receptor (IL-1sR) to one knee joint of rabbits with bilateral antigen-induced arthritis suppressed disease in both the ipsilateral as well as the contralateral uninjected knee. A similar phenomenon has been noted in this model using the viral interleukin 10 (vIL-10) gene (Lechman, 1999, MS Thesis, University of Pittsburgh). Moreover, adenoviral delivery of vIL-10 to the paws of mice with collagen-induced arthritis (CIA) (Whalen et al., 1999 , *J. Immunol.* 162:3625–32) and delivery of IkB to the ankle joints of rats with SCW-induced arthritis (Miagkov et al., 1998, *Proc. Natl. Acad Sci. USA* 95:13859–13864) also suppressed disease in non-injected joints on the same animal. One possible explanation for this contralateral effect is that expression of the rat TNFR:Fc gene in transduced joint tissue leads to secretion of this protein to the circulation which then gains access to uninjected inflamed joints. Our results indicate that the contralateral effect is unlikely due to secretion and systemic distribution of the rat TNFR:Fc protein. These results are also consistent with those of Ghivizzani et al. (1998) who ruled out the likelihood that the gene product or even the adenoviral vector travels to the other joints via systemic circulation or the lymphatics. Thus, our results are most likely consistent with a model that suggests that direct introduction of genes into an arthritic joint leads to the transduction of cells with the ability to traffic to other joints (Ghivizzani et al., 1998).

The circulating levels of bioactive rat TNFR:Fc protein in naive animals (injected intra-muscularly with AAV-ratTNFR:Fc vector) were significantly higher than in the corresponding SCW-treated animals. The possible explanation for this difference is that in SCW-treated animals, the levels of TNF-α are considerably higher than in naive animals as a result of the ongoing systemic inflammatory process. In these diseased animals, the TNF-α molecules are most likely being bound and neutralized by soluble TNFR:Fc protein molecules and cannot be detected in the bioassay.

Example 7 rAAV Vector for Co-Delivery of TNF Antagonist and IL-1 Antagonist

A polynucleotide encoding a TNFR:Fc polypeptide (as described herein) is cloned into an rAAV vector plasmid as described in Example 2 to generate an rAAVTNFR:Fc plasmid. A polynucleotide encoding an IL-1R, GenBank entry U74649, is cloned into the rAAVTNFR:Fc plasmid. Both the TNFR:Fc encoding sequence and the IL-1R encoding sequence are operably linked to transcriptional regulatory sequences and both are enclosed between the AAV ITRs. This rAAV vector plasmid is denoted pAAVTNFR:FcIL-1R.

rAAV producer cell lines are generated by transfection of cells with the pAAVTNFR:FcIL-1R plasmid as described in Example 2. rAAV vector particles are prepared as described herein. Expression of TNFR:Fc activity and of IL-1R activity after transduction of cells with rAAVTNFR:FcIL-1R viral particles is assessed using methods described herein. An IL-1 bioassay is described in Kuiper et al., 1998.

The effect of administration of rAAVTNFR:FcIL-1R viral particles is assessed in the context of a animal arthritis model. rAAV viral particles are administered by different routes including intra-articular, intramuscular and intravenous injections. Assessment of treatment includes determination of inflammation and cartilage destruction in the joints.

---

We claim:

1. A method for reducing tumor necrosis factor (TNF) levels in a mammal, comprising administering a recombinant adeno-associated virus (rAAV) vector to the mammal in an amount sufficient to reduce TNF levels in the mammal, wherein said rAAV vector comprises a polynucleotide encoding a fusion polypeptide comprising an extracellular domain of tumor necrosis factor receptor (TNFR) and a constant domain of an IgG1 molecule, and wherein said rAAV vector is administered by intramuscular injection or intravenous injection.

2. The method of claim 1, further comprising administering a TNF antagonist.

3. The method of claim 1, wherein said rAAV vector is administered by intramuscular injection.

4. The method of claim 1, wherein said rAAV vector is administered by intravenous injection.

5. A method for reducing an inflammatory response in a mammal, comprising administering a recombinant adeno-associated virus (rAAV) vector to the mammal in an amount sufficient to reduce the inflammatory response in the mammal, wherein said rAAV vector comprises a polynucleotide encoding a fusion polypeptide comprising an extracellular domain of tumor necrosis factor receptor (TNFR) and a constant domain of an IgG1 molecule, and wherein said rAAV vector is administered by intramuscular injection or intravenous injection.

6. The method of claim 5, further comprising administering a TNF antagonist.

7. The method of claim 5, wherein the inflammatory response occurs in a connective tissue.

8. The method of claim 5, wherein the inflammatory response occurs in a joint.

9. The method of claim 5, wherein said rAAV vector is administered by intramuscular injection.

10. The method of claim 5, wherein said rAAV vector is administered by intravenous injection.

11. The method of claim 9, wherein the TNF-associated disorder in an inflammatory disorder.

12. A method for palliating a TNF-associated disorder in a mammal, comprising administering a recombinant adeno-associated virus (rAAV) vector to the mammal in an amount sufficient to palliate the TNF-associated disorder condition, wherein said rAAV vector comprises a polynucleotide encoding a fusion polypeptide comprising an extracellular domain of tumor necrosis factor receptor (TNFR) and a constant domain of an IgG1 molecule, and wherein said rAAV vector is administered by intramuscular injection or intravenous injection.

13. The method of claim 11, further comprising administering a TNF antagonist.

14. The method of claim 12, wherein said rAAV vector is administered by intramuscular injection.

15. The method of claim 12, wherein the inflammatory disorder is an arthritic condition.

16. The method of claim 12, wherein said rAAV vector is administered by intravenous injection.

* * * * *

UNITED STATES PATENT AND TRADEMARK OFFICE

CERTIFICATE OF CORRECTION

PATENT NO. : 6,537,540 B1

DATED : March 25, 2003

INVENTOR(S) : Haim Burstein and Anthony M. Stepan

It is certified that error appears in the above-identified patent and that said Letters Patent is hereby corrected as shown below:

Column 70,
Line 29, please replace "claim 9" with -- claim 12 --.
Line 30, please replace "disorder in" with -- disorder is --.
Line 41, please replace "claim 11" with -- claim 12 --.
Line 45, please replace "claim 12" with -- claim 11 --.

Signed and Sealed this

Thirtieth Day of September, 2003

JAMES E. ROGAN

*Director of the United States Patent and Trademark Office*